(12) United States Patent
Decrulle et al.

(10) Patent No.: US 11,124,776 B2
(45) Date of Patent: Sep. 21, 2021

(54) PHARMACEUTICAL COMPOSITIONS COMPRISING BACTERIAL DELIVERY VEHICLES AND USES THEREOF

(71) Applicant: Eligo-Bioscience, Paris (FR)

(72) Inventors: Antoine Decrulle, Paris (FR); Xavier Duportet, Paris (FR); Igor Stzepourginski, Paris (FR)

(73) Assignee: Eligo-Bioscience

( * ) Notice: Subject to any disclaimer, the term of this patent is extended or adjusted under 35 U.S.C. 154(b) by 4 days.

(21) Appl. No.: 16/444,576

(22) Filed: Jun. 18, 2019

(65) Prior Publication Data
US 2019/0390175 A1 Dec. 26, 2019

(30) Foreign Application Priority Data

Jun. 20, 2018 (EP) .................................... 18305781

(51) Int. Cl.
| | | |
|---|---|---|
| C12N 7/00 | (2006.01) | |
| A61K 31/7088 | (2006.01) | |
| A61K 45/06 | (2006.01) | |
| C12N 15/11 | (2006.01) | |
| C12N 15/70 | (2006.01) | |
| A61K 38/46 | (2006.01) | |
| C12N 9/22 | (2006.01) | |
| A61K 39/108 | (2006.01) | |
| A61K 39/02 | (2006.01) | |
| A61K 39/00 | (2006.01) | |

(52) U.S. Cl.
CPC ............ C12N 7/00 (2013.01); A61K 31/7088 (2013.01); A61K 38/465 (2013.01); A61K 39/0258 (2013.01); A61K 45/06 (2013.01); C12N 9/22 (2013.01); C12N 15/11 (2013.01); C12N 15/70 (2013.01); *A61K 2039/525* (2013.01); *A61K 2039/53* (2013.01); *C12N 2310/20* (2017.05); *C12N 2795/10134* (2013.01); *C12N 2795/10143* (2013.01); *C12N 2795/10171* (2013.01); *C12N 2795/10334* (2013.01); *C12N 2795/10343* (2013.01); *C12N 2795/10371* (2013.01); *C12N 2800/80* (2013.01)

(58) Field of Classification Search
None
See application file for complete search history.

(56) References Cited

U.S. PATENT DOCUMENTS

| | | |
|---|---|---|
| 4,920,048 A | 4/1990 | Diderichsen |
| 5,691,185 A | 11/1997 | Dickely et al. |
| 6,291,245 B1 | 9/2001 | Kopetzki et al. |
| 6,413,768 B1 | 7/2002 | Galen |
| 6,752,994 B2 | 6/2004 | Jacobs, Jr. et al. |
| 2015/0064138 A1 | 3/2015 | Lu et al. |

FOREIGN PATENT DOCUMENTS

| | | | |
|---|---|---|---|
| WO | WO 2007/141540 | * | 12/2007 |
| WO | 2008157515 A1 | | 12/2008 |
| WO | 2014124226 A1 | | 8/2014 |

OTHER PUBLICATIONS

Ma et al., Scientific Reports, Feb. 2, 2018; 8:2326. (Year: 2018).*
Abudayyeh, O., et al. (2017) RNA targeting with CRISPR—Cas13. Nature 550, 280.
Beaber, et al., A new helper for improved monovalent display of Fab molecules, J Immunol Methods (2012) 376, 46-54.
Bikard, et al., 2014, Development of Sequence-specific antimicrobials based on programmable CRISPR-Cas nucleases, Nat Biotech 11, vol. 32.
Bikard et al., 2012, CRISPR Interference Can prevent Natural Transformation and Virulence Acquisition during In Vivo Bacterial Infection, Cell Host &Microbe 12, 177-186.
Cambray G et al, Measurement and Modeling of Intrinsic Transcription Terminators, (Nucl Acids Res, 2013, 41(9): 5139-5148).
Casjens, et al., Determining DNA Packaging Strategy by Analysis of the Termini of the Chromosomes in Tailed-Bacteriophage Virions, Methods Mol Biol. 502: 91-111 (2009).
Chen, et al., Characterization of 582 Natural and Synthetic Terminators and Quantification of their Design Constraints (2013), Nature Methods, 10: 659-664).
Chung, YB, et al., Bacteriophage T7 DNA Packaging, II. Analysis of the DNA Sequences Required for Packaging Using a Plasmid Transduction Assay, J Mol. Biol., 216:927-938 (1990).
Citorik, R et al, 2014, Sequence-specific antimicrobials using efficiently delivered RNA-guided nucleases, Nat Biotech 11,vol. 32, 1141-1145.
Collins, et al., (1978). Cosmids: A type of plasmid gene-cloning vector that is packageable in vitro in bacteriophage I heads. PNAS 75(9) : 4242-4246.
Cotter, et al., Bacteriocins—a viable alternative to antibiotics, Nature Reviews Microbiology 11: 95, 2013.

(Continued)

*Primary Examiner* — Nicole Kinsey White
(74) *Attorney, Agent, or Firm* — Carter, DeLuca & Farrell LLP

(57) ABSTRACT

The present invention relates to the delivery of a payload by bacterial delivery vehicle, i.e. the encapsulation and the delivery of a single plasmid by different bacterial virus particles. More specifically, the present invention concerns a pharmaceutical composition comprising a payload packaged in at least two different bacterial delivery vehicles and a method of production thereof.

17 Claims, 1 Drawing Sheet

Specification includes a Sequence Listing.

(56) References Cited

OTHER PUBLICATIONS

Cronan, J. Improved plasmid-based system for fully regulated off-to-on gene expression in *Escherichia coli*: Application to production of toxic proteins. Plasmid 69, 81-89 (2013).
Del Solar et al., Replication and Control of Circular Bacterial Plasmids, 1998 Microbio and Molec Biol. Rev 62:434-464.
Dickely, et al., Isolation of Lactococcus lactis nonsense suppressors and construction of a food-grade cloning vector (1995), Mol. Microbiol. 15:839-847).
Duenas et al., Novel helper phage design: intergenic region affects the assembly of bacteriophages and the size of antibody libraries, FEMS Microbiology Letters, 125 (1995) 317-322.
Engelberg-Kulka, et al., Addiction Modules and Programmed Cell Death and Antideath in Bacterial Cultures, Annu. Rev. Microbiol. 53 (1999) 43-70.
Fems, Novel helper phage design: intergenic region affects the assembly of bacteriophages and the size of antibody libraries, Microbiol Lett (1995) 125, 317-321.
Fiedler, et al., proBA complementation of an auxotrophic *E. coli* strain improves plasmid stability and expression yield during fermenter production of a recombinant antibody fragment (2001) Gene 274: 111-118).
Fonfara, I., et al. (2014). Phylogeny of Cas9 determines functional exchangeability of dual-RNA and Cas9 among orthologous type II CRISPR-Cas systems. Nucleic Acids Research 42, 2577-2590.
Garneau Jr, et al., PhageTerm: a tool for fast and accurate determination of phage termini and packaging mechanism using next-generation sequencing data, Scientific Reports 2017 7(1):8292.
Groenen, et al., Mapping of a Site for Packaging of Bacteriophage Mu DNA, Virology 144:520-522 (1985).
Gunther, et al. (1993). High efficiency, restriction-deficient in vitro packaging extracts for bacteriophage lambda DNA using a new *E. coli* lysogen. NAR 21(16) : 3903-3904.
Hashimoto, et al., DNA Sequences Necessary for Packaging Bacteriophage T3 DNA, Virology 187:788-795 (1992).
Henkel, et al., Toxins from Bacteria in EXS. 2010; 100: 1-29.
Hohn, DNA sequences necessary for packaging of bacteriophage DNA, Proc. Natl. Acad. Sci. USA, vol. 80, pp. 7456-7460 (1983).
Hohn, et al., (1977). Packaging recombinant DNA molecules into bacteriophage particles in vitro. PNAS 74(8): 3259-3263.
Jestin, et al., Improving the display of proteins on filamentous phage, Res. Microbiol, 152 (2001) 187-191.
Jiang et al., CRISPR-assisted editing of bacterial genomes, 2013, Nat Biotechnol 31, 233-239.
Kanhere, et al., A novel method for prokaryotic promoter prediction based on DNA stability, BMC Bioinformatics 2005, 6:1.
Koonin, E., et al. (2017). Diversity, classification and evolution of CRISPR-Cas systems. Curr Opin Microbiol 37, 67-78.
Kramer, et al., A novel helper phage that improves phage display selection efficiency by preventing the amplification of phages without recombinant protein, Nucleic Acids Research, ; (2003), vol. 31, No. 11 e59.
Krupovic, M., et al. (2015). Taxonomy of prokaryotic viruses: update from the ICTV bacterial and archaeal viruses subcommittee. Arch Virol 161, 1095-1099.
Kues, et al., Replication of Plasmids in Gram-Negative Bacteria, U Microbiol Rev 53:491-516 (1989).
Mead, et al., Chimeric Single-Stranded DNA Phage-Plasmid Cloning Vectors, Biotechnology 10, 85-102 (1988).
Miwa, et al., Identification of sequences necessary for packaging DNA into lambda phage heads, Gene 20:267-279 (1982).
Needleman, et al., A general method applicable to the search for similarities in the amino acid sequence of two proteins, Journal of Molecular Biology, 48, 443-453 (1970).
Nilssen, et al., DeltaPhage—a novel helper phage for high-valence pIX phagemid display, Nucleic Acids Research, (2012) vol. 40, No. 16 e120.
Petri, et al., Isolation of fragments with pac function for phage P22 from phage LP7 DNA and comparison of packaging gene 3 sequences, Gene 88:47-55 (1990).
Rakonjac, et al., Filamentous phage infection-mediated gene expression: construction and propagation of the gIII deletion mutant helper phage R408d3, Gene, (1997) 198, 99-103.
Rondot, et al., A helper phage to improve single-chain antibody presentation in phage display, Nature Publishing Group, (2001) 19, 75-78.
Russel et al., Genetic Analysis of the Filamentous Bacteriophage packaging Signal and of the Proteins That Interact with It, J Virol, 63:3284-3295 (1989).
Silver, et al., Bacterial Heavy Metal Resistance: New Surprises, Annu. Rev. Microbiol. 50 (1996) 753-789.
Soltes, et al., A new helper phage and phagemid vector system improves viral display of antibody Fab fragments and avoids propagation of insert-less virions, J Immunol Methods (2003) 274, 233-244.
Struhl, et al., Functional genetic expression of eukaryotic DNA in *Escherichia coli* (1976) PNAS USA 73; 1471-1475.
Wang, et al., Cloning of Genes that Suppress an *Escherichia coli* K-12 Alanine Auxotroph When Present in Multicopy Plasmids, Journal of Bacteriology, (1987), p. 5610-5614.
Wu, et al., The DNA site utilized by bacteriophage P22 for initiation of DNA packaging, Molec Microbiol 45:1631-1646 (2002).
European Search Report dated Feb. 27, 2019, corresponding to corresponding European Application No. 18305781.9; 16 total pages.
Westwater et al., "Development of a P1 Phagemid System for the Delivery of DNA into Gram-negative Bacteria," Journal of General Microbiology, vol. 148, No. 4, Apr. 1, 2002; pp. 943-950.
Krom et al., "Engineered Phagemids for Nonlytic, Targeted Antibacterial Therapies," Nano Letters, vol. 15, No. 7, Jul. 8, 2015; pp. 4808-4813.
Westwater et al, "Use of Genetically Engineered Phage to Deliver Antimicrobial Agents to Bacteria: An Alternative Therapy for Treatment of Bacterial Infections," Antimicrobial Agents and Chemotherapy, American Society for Microbiology, US, vol. 47, No. 4, Apr. 1, 2003; pp. 1301-1307.
Lu et al., "Engineered Bacteriophage Targeting Gene Networks as Adjuvants for Antibiotic Therapy," Proceedings of the National Academy of Sciences of the United States of America, National Academy of Sciences, US, vol. 106, No. 12, Mar. 24, 2009; pp. 4629-4634.
Pires et al., "Genetically Engineered Phages: a Review of Advances over the Last Decade," Microbiology and Molecular Biology Reviews, vol. 80, No. 3, Jun. 1, 2016; pp. 523-543.
Ziermann et al., "Characterization of the cos Sites of Bacteriophages P2 and P4," Gene, vol. 96, No. 1, Jan. 1, 1990; pp. 9-15.

* cited by examiner

|  | P1-phagemid (particles/μL) | Lambda-phagemid (particles/μL) | 186-phagemid (particles/μL) |
|---|---|---|---|
| production 1 | $7.2 \cdot 10^4$ | $1.8 \cdot 10^7$ | $7.7 \cdot 10^5$ |
| production 2 | $7.7 \cdot 10^4$ | $2.6 \cdot 10^7$ | $5.7 \cdot 10^5$ |
| production 3 | $8.8 \cdot 10^4$ | $3.2 \cdot 10^7$ | $9.9 \cdot 10^5$ |
| Mean | $7.9 \cdot 10^4$ | $2.53 \cdot 10^7$ | $7.77 \cdot 10^5$ |
| Standard deviation | $8.2 \cdot 10^3$ | $7.0 \cdot 10^6$ | $2.1 \cdot 10^5$ |

SEQUENCE LISTING

```
<160> NUMBER OF SEQ ID NOS: 6

<210> SEQ ID NO 1
<211> LENGTH: 791
<212> TYPE: DNA
<213> ORGANISM: Artificial Sequence
<220> FEATURE:
<223> OTHER INFORMATION: Synthetic:  P1 Pac

<400> SEQUENCE: 1
acctgggacg atcacaagaa gaattttgct cgcctggcgc gagatggtgg ttacaccatc      60
gcacagtatg ccgccgagtt taatcttaac cctaataccg cacgtcgtta tctccgtgcc     120
ttcaaagagg acaccaggac tacggacagc cgcaagccaa ataagccagt caggaagcca     180
ctaaaaagca tgatcattga tcactctaat gatcaacatg caggtgatca cattgcggct     240
gaaatagcgg aaaaacaaag agttaatgcc gttgtcagtg ccgcagtcga gaatgcgaag     300
cgccaaaata agcgcataaa tgatcgttca gatgatcatg acgtgatcac ccgcgcccac     360
cggaccttac gtgatcgcct ggaacgcgac accctgatg atgatggtga acgctttgag      420
ttcgaagttg gcgattacct gatagataac gttgaagcgc ggaaggccgc gcgcgctatg     480
ttgcgtcggt ccggggccga tgttctggaa accactcttc tggaaaagtc tctttctcat     540
ctccttatgc tggagaacgc cagggatacg tgtattcgcc tggtgcagga aatgcgcgat     600
cagcaaaaag acgatgatga aggtactccg cctgaatacc gtatcgcgag catgctaaac     660
agctgttccg cgcagataag cagcctgatc aacaccattt acagcatccg gaataactat     720
cgaaaagaaa gccgggaggc ggaaaagcac gctttatcta tggggcaagc tggcattgtt     780
aagctggcat a                                                          791

<210> SEQ ID NO 2
<211> LENGTH: 325
<212> TYPE: DNA
<213> ORGANISM: Artificial Sequence
<220> FEATURE:
<223> OTHER INFORMATION: Synthetic:  Cos P4

<400> SEQUENCE: 2
gcatgcgttt tcctgcctca ttttctgcaa accgcgccat tcccggcgcg gtctgagcgt      60
gtcagtgcaa ctgcattaaa accgccccgc aaagcgggcg ggcgaggcgg ggaaagcacc     120
gcgcgcaaac cgacaagtta gttaattatt tgtgtagtca aagtgccttc agtacatacc     180
tcgttaatac attggagcat aatgaagaaa atctatggcc tatggtccaa aactgtcttt     240
tttgatggca ctatcctgaa aaatatgcaa aaaatagatt gatgtaaggt ggttcttgtc     300
agtgtcgcaa gatccttaag aattc                                           325
```

<210> SEQ ID NO 3
<211> LENGTH: 224
<212> TYPE: DNA
<213> ORGANISM: Artificial Sequence
<220> FEATURE:
<223> OTHER INFORMATION: Synthetic: Cos lambda

<400> SEQUENCE: 3

```
ccaaaaagcc tcgctttcag cacctgtcgt ttcctttctt ttcagagggt attttaaata    60
aaaacattaa gttatgacga agaagaacgg aaacgcctta aaccggaaaa ttttcataaa   120
tagcgaaaac ccgcgaggtc gccgccccgt aacctgtcgg atcaccggaa aggacccgta   180
aagtgataat gattatcatc tacatatcac aacgtgcgta aagg                   224
```

<210> SEQ ID NO 4
<211> LENGTH: 84
<212> TYPE: DNA
<213> ORGANISM: Artificial Sequence
<220> FEATURE:
<223> OTHER INFORMATION: Synthetic: Cos P2

<400> SEQUENCE: 4

```
taaggtgcat taaaaccgcc ccgtgaagcg ggcgggcgag gcggggaaag cacggcgagg    60
cggggaaagc actgcgcgct gacg                                          84
```

<210> SEQ ID NO 5
<211> LENGTH: 140
<212> TYPE: DNA
<213> ORGANISM: Artificial Sequence
<220> FEATURE:
<223> OTHER INFORMATION: Synthetic: Cos 186

<400> SEQUENCE: 5

```
tgttttgcat gcgtcaggct tgcccgttct ggttgtgcgt cgccagagct ggcgcggctc    60
cagagtggtc atgcaactgc attaaaaccg acccataaag tgggcaggcg tggcggggaa   120
agcattgcgc gccagaggtg                                              140
```

<210> SEQ ID NO 6
<211> LENGTH: 1115
<212> TYPE: DNA
<213> ORGANISM: Artificial Sequence
<220> FEATURE:
<223> OTHER INFORMATION: Synthetic: T7 concatemer junction

<400> SEQUENCE: 6

```
agtccatgca gttggattcc gttaaggtcg agggtgaagt acttgctgac ttccttgagg    60
aacacatgat gcgtcctacg gttgctgcta cgcatatcat tgagatgtct gtgggaggag   120
ttgatgtgta ctctgaggac gatgagggtt acggtacgtc tttccattga gtggtgattta  180
tgcattagga ctgcataggg atgcactata gaccacggat ggtcagttct ttaagttact   240
gaaaagacac gataaattaa tacgactcac tataggaga ggaggacga aaggttacta    300
tatagatact gaatgaatac ttatagagtg cataaagtat gcataatggt gtacctagag   360
tgacctctaa gaatggtgat tatattgtat tagtatcacc ttaacttaag gaccaacata   420
aagggaggag actcatgttc cgcttattgt tgaacctact gcggcataga gtcacctacc   480
gatttcttgt ggtactttgt gctgcccttg gtacgcatc tcttactgga gacctcagtt    540
cactggagtc tgtcgtttgc tctatactca cttgtagcga ttagggtctt cctgaccgac   600
tgatggctca ccgagggatt cagcggtatg attgcatcac accacttcat ccctatagag   660
```

-continued

| | | | | | | |
|---|---|---|---|---|---|---|
| tcaagtccta | aggtataccc | ataaagagcc | tctaatggtc | tatcctaagg | tctataccta | 720 |
| aagataggcc | atcctatcag | tgtcacctaa | agagggtctt | agagagggcc | tatggagttc | 780 |
| ctatagggtc | ctttaaaata | taccataaaa | atctgagtga | ctatctcaca | gtgtacggac | 840 |
| ctaaagttcc | cccatagggg | gtacctaaag | cccagccaat | cacctaaagt | caaccttcgg | 900 |
| ttgaccttga | gggttcccta | agggttgggg | atgaccettg | ggtttgtctt | tgggtgttac | 960 |
| cttgagtgtc | tctctgtgtc | cctatctgtt | acagtctcct | aaagtatcct | cctaaagtca | 1020 |
| cctcctaacg | tccatcctaa | agccaacacc | taaagcctac | acctaaagac | ccatcaagtc | 1080 |
| aacgcctatc | ttaaagttta | aacataaaga | ccaga | | | 1115 |

PHARMACEUTICAL COMPOSITIONS COMPRISING BACTERIAL DELIVERY VEHICLES AND USES THEREOF

REFERENCE TO SEQUENCE LISTING SUBMITTED VIA EFS-WEB

This application includes an electronically submitted sequence listing in .txt format. The .txt file contains a sequence listing entitled "2643-10_ST25.txt" created on Sep. 9, 2019 and is 4,739 bytes in size. The sequence listing contained in this .txt file is part of the specification and is hereby incorporated by reference herein in its entirety.

FIELD OF THE INVENTION

The invention relates to the field of molecular biology and particularly to the delivery of a payload by bacterial delivery vehicle. More specifically, the present invention concerns the encapsulation and the delivery of a plasmid by bacterial virus particles.

BACKGROUND OF THE INVENTION

Nowadays, the treatment of bacterial infections mainly relies on the use of antibiotics. However, excessive and inappropriate use of antibiotics has fostered the emergence and spread of antibiotic-resistant microorganisms. Indeed, infections caused by antibiotic-resistant microorganisms, also known as "superbugs", sometimes no longer respond to conventional treatments, thereby extending the duration of the disease related to infection and even leading to patient death. Because of the development of this antibiotic resistance phenomenon and the lack of discovery of new antibiotic classes, humanity is now facing the possibility of a future without effective treatment for bacterial infections.

Bacterial viruses (or phages) are small viruses displaying the ability to infect and kill bacteria while they do not affect cells from other organisms. Initially described almost a century ago by William Twort, and independently discovered shortly thereafter by Felix d'Herelle, more than 6000 different bacterial viruses have been discovered so far and described morphologically. The vast majority of these viruses are tailed while a small proportion are polyhedral, filamentous or pleomorphic. They may be classified according to their morphology, their genetic content (DNA vs. RNA), their specific host, the place where they live (marine virus vs. other habitats), and their life cycle. As intracellular parasites of bacterial cells, phages display different life cycles within the bacterial host: lytic, lysogenic, pseudo-lysogenic, and chronic infection. Lytic phages, once their DNA injected into their host, replicate their own genome and produce new viral particles at the expense of the host. Indeed, they cause lysis of the host bacterial cell as a normal part of the final stage of their life cycles to liberate viral particles. Temperate phages (also termed temperate phages) can either replicate by means of the lytic life cycle and cause lysis of the host bacterium, or they can incorporate their DNA into the host bacterial DNA and become non-infectious prophages (lysogenic cycle). Nowadays, only strictly lytic phages are chosen for phage therapy.

Currently, several phage therapy clinical trials are in progress and they all rely on a mixture of different purified phages, also called phage cocktail. Usually, phage cocktails are composed of at least 3 phages, up to 10 phages in some cases. Combining phages permit to increase the host range of the drug by combining each individual phage host range. Because the different phages have different host receptors, it also reduces the chance that, through mutation of a receptor, resistant bacterium arises. Phage cocktail is therefore a combination of different phages, each one of them encoding different proteins that will lead to the death of the host. It means that each phage can kill the cell in a different way (degrading DNA, bursting the cell, hijacking molecular machinery, etc.). Moreover, each phage genome is contained in different phage particles targeting different receptors. This turns out to be regulatory difficult to get approved because of its complexity.

On the contrary, the use of packaged phagemids (viral particle where phage genome is replaced by a plasmid of interest) allows to have a defined and control way of killing the host. Example of packaged phagemids encoding CRISPR-Cas9 or toxins have shown promising results in killing targeted bacterial population (Bikard et al., 2012, Cell Host & Microbe 12, 177-186; Jiang et al., 2013, Nat Biotechnol 31, 233-239; Krom et al., 2015, Nano Letters 15, 4808-4813; Bikard et al, 2014, Nat Biotech 11, Vol. 32, Citorik, R et al, 2014, Nat Biotech 11, Vol. 32).

However, the use of packaged phagemid has been restricted to a single plasmid encapsidated in a single viral particle. This is not optimal for in vivo and clinical applications. Indeed, due to the genetic and epigenetic heterogeneity of pathogenic bacterial population in vitro and in vivo, the chance for a single viral particle to be injected in all clinically relevant strains is low. In addition, a single mutation changing the receptor could be enough for a resistant bacterial population to spread.

WO2008/157515 relates to the cloning of genomic libraries using phage encapsidation mechanisms. In particular, encapsidation initiation sites (PIS) are introduced at the level of a target DNA by transposition. These sites allow the encapsulation of the target DNA in phage capsids. The DNA encapsidated is then purified, ligated with a cohesive end and re-encapsidated and cloned into a bacterial strain for further sequencing. More particularly, this document discloses a plasmid pDW7 (FIG. 5) comprising the encapsidation sites cos and pac. However, the purpose of WO2008/157515 has nothing in common with the purpose of the present invention. Indeed, the method described in this document will never lead to the encapsidation in different delivery vehicles and pDW7 has not been designed for and does not code for the expression of a protein of interest into the target bacteria.

SUMMARY OF THE INVENTION

To overcome these problems, a first phagemid cocktail or mixture has been developed based on a single payload containing at least 2 orthogonal packaging sites, allowing its packaging into at least two different bacterial delivery vehicles.

The invention concerns a pharmaceutical composition comprising at least two different bacterial delivery vehicles into which the same payload is packaged. Such payload comprises a nucleic acid sequence of interest under the control of a promoter and at least two orthogonal bacterial virus packaging sites that allow packaging of said payload into said at least two different bacterial delivery vehicles.

Preferably, the at least two orthogonal bacterial virus packaging sites are at least two different cos sites, at least two different pac sites or at least two different concatemer junction sites.

Alternatively, the at least two orthogonal bacterial virus packaging sites are at least one cos site and at least one pac site, at least one cos site and at least one concatemer junction site, at least one pac site and at least one concatemer junction site, or at least one cos site, at least one pac site and at least one concatemer junction site.

In one aspect, the at least two orthogonal bacterial virus packaging sites are selected in the group consisting of λ cos site, P4 cos site, SPP1 pac site, P1 pac site, T1 pac site, mu pac site, P22 pac site, φ8 pac site, Sf6 pac site, 149 pac site, T7 concatemer junction, and A1 122-concatemer junction. For instance, the at least two orthogonal bacterial virus packaging sites comprising λ cos site and P4 cos site, or λ cos site, P4 cos site and P1 pac site, or λ cos site, P4 cos site and T7 concatemer junction, or λ cos site, P4 cos site, P1 pac site and T7 concatemer junction.

The nucleic sequence of interest of the payload according to the invention can be selected from the group consisting of a Cas nuclease, a Cas9 nuclease, a guide RNA, a single guide RNA (sgRNA), a CRISPR locus, a toxin, a gene expressing an enzyme such as a nuclease or a kinase, a TALEN, a ZFN, a meganuclease, a recombinase, a bacterial receptor, a membrane protein, a structural protein, a secreted protein, a gene expressing resistance to an antibiotic or to a drug in general, a gene expressing a toxic protein or a toxic factor, and a gene expressing a virulence protein or a virulence factor, or any combination thereof.

The nucleic sequence of interest may particularly be an encoding element(s) of the CRISPR/Cas system for the reduction of gene expression or inactivation of a gene selected from the group consisting of an antibiotic resistance gene, virulence factor or protein gene, toxin factor or protein gene, a gene expressing a bacterial receptor, a membrane protein, a structural protein, a secreted protein, and a drug resistance gene, or any of their combination thereof.

The bacterial delivery vehicles according to the invention can particularly be bacterial viruses, preferably bacterial viruses selected from the group consisting of BW73, B278, D6, D108, E, E1, E24, E41, FI-2, FI-4, FI-5, HI8A, Ff18B, i, MM, Mu, 025, PhI-5, Pk, PSP3, P1, P1D, P2, P4, S1, Wφ, φK13, φ1, φ2, φ7, φ92, 7 A, 8φ, 9φ, 18, 28-1, 186, 299, HH-*Escherichia* (2), AB48, CM, C4, C16, DD-VI, E4, E7, E28, FI1, FI3, H, H1, H3, H8, K3, M, N, ND-2, ND-3, ND4, ND-5, ND6, ND-7, Ox-I, Ox-2, Ox-3, Ox-4, Ox-5, Ox-6, PhI-I, RB42, RB43, RB49, RB69, S, SaI-I, Sa1-2, Sa1-3, Sa1-4, Sa1-5, Sa1-6, TC23, TC45, TuII*-6, TuIP-24, TuII*46, TuIP-60, T2, T4, T6, T35, al, 1, IA, 3, 3A, 3T+, 5φ, 9266Q, CFO103, HK620, J, K, K1F, m59, no. A, no. E, no. 3, no. 9, N4, sd, T3, T7, WPK, W31, ΔH, φC3888, φK3, φK7, φK12, φV-1, Φ04-CF, Φ05, Φ06, Φ07, φ1, φ1.2, φ20, φ95, φ263, φ1O92, φ1, φ11, Ω8, 1, 3, 7, 8, 26, 27, 28-2, 29, 30, 31, 32, 38, 39, 42, 933W, NN-*Escherichia* (1), Esc-7-11, AC30, CVX-5, C1, DDUP, EC1, EC2, E21, E29, F1, F26S, F27S, Hi, HK022, HK97, HK139, HK253, HK256, K7, ND-I, PA-2, q, S2, T1,), T3C, T5, UC-I, w, β4, γ2, λ, ΦD326, φγ, Φ06, Φ7, Φ10, φ80, χ, 2, 4, 4A, 6, 8A, 102, 150, 168, 174, 3000, AC6, AC7, AC28, AC43, AC50, AC57, AC81, AC95, HK243, K1O, ZG/3A, 5, 5A, 21EL, H19-J and 933H.

Particularly, the bacterial delivery vehicles are capable of targeting at least two different bacteria and of introducing the payload into the bacteria.

Alternatively, the bacterial delivery vehicles are capable of targeting the same bacteria and of introducing the payload into these bacteria.

The pharmaceutical composition according to the invention comprise the disclosed bacterial delivery vehicles and at least one additional active ingredient, for instance a prebiotic and/or a probiotic and/or an antibiotic, and/or another antibacterial or antibiofilm agent, and/or any agent enhancing the targeting of the bacterial delivery vehicle to a bacteria and/or the delivery of the payload into a bacteria.

The pharmaceutical composition according to the invention may be for use as a medicament.

In a particular embodiment, the pharmaceutical composition may be used for in-situ bacterial production of a compound of interest, preferably said compound of interest being produced inside the targeted bacteria, secreted from the targeted bacteria or expressed on the surface of the targeted bacteria. Particularly, the compound of interest can be an antigen expressed on the surface of the targeted bacteria for prophylactic and/or therapeutic vaccination.

The pharmaceutical composition according to the invention may be for use in the treatment of a disorder or disease caused by a bacterium, preferably by an antibiotic-resistant bacterium, such as an infection, preferably a bacterial infection, inflammatory diseases, auto-immune diseases, cancers, metabolic disorders and/or brain disorders.

The pharmaceutical composition according to the invention may also be for use in the prevention of a disorder or a disease caused by a bacterium found in a subject, preferably by an antibiotic-resistant bacterium, such as an infection, preferably a bacterial infection, inflammatory diseases, auto-immune diseases, cancers, metabolic disorders and/or brain disorders.

The invention also concerns a payload comprising a nucleic acid sequence of interest under the control of a promoter and at least two orthogonal bacterial virus packaging sites that allow packaging of the payload into said at least two different bacterial delivery vehicles. Such payload may be a plasmid.

The invention finally concerns a bacterial delivery vehicle comprising the payload according to the invention. Such bacterial delivery vehicle may be a bacterial virus particle.

DETAILED DESCRIPTION OF THE INVENTION

Introduction

Figures 1, 2:
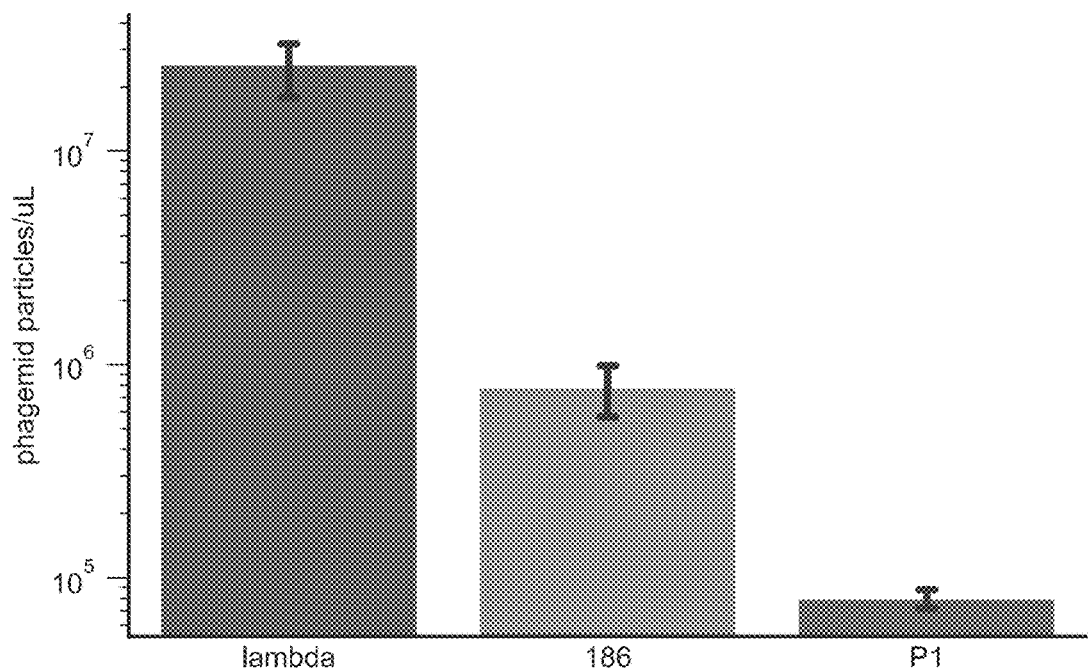
FIG. 1: Concentration of phagemid particles produce from the different lysogenes.
FIG. 2: Data from three independent phagemids production.

The present invention relates to a payload suitable to be packaged into at least two different bacterial delivery vehicles. This payload comprises at least two orthogonal bacterial viruses packaging sites that allow packaging of the payload into at least two different bacterial delivery vehicles. Indeed, the advantage is to be able to deliver the same payload to target cells by at least two different bacterial delivery vehicles. Then, it allows the preparation of a pharmaceutical or veterinary composition comprising at least two different bacterial delivery vehicles, each bacterial delivery vehicle having the same payload. In addition, depending on the patient or subject conditions, the person skilled in the art will be able to select the most appropriate bacterial delivery vehicle for each case and to prepare the selected bacterial delivery vehicle with the packaged payload.

The present disclosure relates to a bacterial delivery vehicle comprising such a payload packaged into the bacterial delivery vehicle. It relates to a composition, especially a pharmaceutical or veterinary composition, comprising at least two different bacterial delivery vehicles, the bacterial delivery vehicles comprising the same payload.

It also relates to a bacterial cell comprising such a payload, in particular bacterial cells capable of producing a bacterial delivery vehicle comprising such a payload, and to a method for producing such a bacterial delivery vehicle.

The present disclosure relates to the use of the bacterial delivery vehicle comprising such a payload or the composition, especially a pharmaceutical or veterinary composition, comprising at least two different bacterial delivery vehicles, the bacterial delivery vehicles comprising the same payload as a medicament, especially in the treatment of a disorder or disease, in particular caused by a bacterium.

In another aspect a kit is provided comprising a payload as defined herein, optionally a satellite phage and/or a helper phage to promote the packaging of the payload in a delivery vehicle, such as a bacterial virus particle, or the structural and functional proteins necessary to promote an in vitro packaging of the payload in a bacterial virus particle, and optionally bacterial cells suitable for packaged payload production.

The bacterial delivery vehicles, preferably the bacterial virus particle, are prepared from bacterial virus, in particular bacteriophages. The bacterial viruses are chosen in order to be able to introduce the payload into the targeted bacteria.

Definitions

To facilitate the understanding of the invention, a number of terms are defined below.

The terms "polynucleotide", "nucleic acid" and "nucleic acid sequence" are equivalent and refer to a polymeric form of nucleotide of any length, preferably to a sequence of at least two nucleotides covalently linked together which can be single-stranded or double-stranded or contains portion of both single-stranded and double-stranded sequence. Nucleic acids (e.g., components, or portions of the nucleic acids) of the present invention may be naturally occurring or engineered. Engineered nucleic acids include recombinant nucleic acids and synthetic nucleic acids. Nucleic acids can be in the form of a circular sequence or a linear sequence or a combination of both forms. The nucleic acid can be DNA, both genomic or cDNA, or RNA or a combination of both. The nucleic acid may contain any combination of deoxyribonucleotides and ribonucleotides, and any combination of bases. Any combination of the above features of a nucleic acid is also encompassed by the present invention.

As used herein, the term "gene" can be a genomic gene comprising transcriptional and/or translational regulatory sequences and/or a coding region and/or non-translated sequences (e.g., introns, 5'- and 3'-untranslated sequences and regulatory sequences). The coding region of a gene can be a nucleotide sequence coding for an amino acid sequence or a functional RNA, such as tRNA, rRNA, catalytic RNA, siRNA, miRNA and antisense RNA. A gene can also be an mRNA or cDNA corresponding to the coding regions (e.g. exons and miRNA) optionally comprising 5'- or 3' untranslated sequences linked thereto. A gene can also be an amplified nucleic acid molecule produced in vitro comprising all or a part of the coding region and/or 5'- or 3'-untranslated sequences linked thereto.

The terms "polypeptide" and "protein" are used interchangeably herein. Polypeptides described herein may be composed of standard amino acids (i.e., the 20 L-alpha-amino acids that are specified by the genetic code, optionally further including selenocysteine and/or pyrrolysine). Polypeptides may comprise one or more non-standard amino acids. Non-standard amino acids can be amino acids that are found in naturally occurring polypeptides, e.g., as a result of post-translational modification, and/or amino acids that are not found in naturally occurring polypeptides. Polypeptides may comprise one or more amino acid analogues known in the art. Beta-amino acids or D-amino acids may be used. One or more of the amino acids in a polypeptide or peptide may be modified, for example, by the addition of a chemical entity such as a carbohydrate group, a phosphate group, a fatty acid group, a linker for conjugation, functionalization, etc. A polypeptide that has a non-polypeptide moiety covalently or non-covalently associated may still be referred to as a "polypeptide". Polypeptides may be purified from natural sources, produced in vitro or in vivo in suitable expression systems using recombinant DNA technology, synthesized through chemical means such as conventional solid phase peptide synthesis and/or using methods involving chemical ligation of synthesized peptides. The term "polypeptide sequence" or "protein sequence" or "amino acid sequence" as used herein can refer to the polypeptide material itself and/or to the sequence information (i.e. the succession of letters or three letter codes used as abbreviations for amino acid names) that biochemically characterizes a polypeptide.

The term "heterologous" in the context of a nucleic acid construct (payload, plasmid, vector or cargo) indicates that the nucleic acid comprises two or more subsequences that are not found in the same relationship to each other in nature. For instance, a nucleic acid is typically recombinantly produced, has two or more sequences from unrelated genes arranged to make a new functional nucleic acid, e.g., a nucleic acid encoding a fluorescent protein from one source and a nucleic acid encoding a peptide sequence from another source. Similarly, a heterologous protein indicates that the protein comprises two or more subsequences that are not found in the same relationship to each other in nature. In the context of a host cell, it means that the sequence encodes a protein which originates from a source different from the cell in which it is introduced or that the coding sequence comes from the same species as the cell in which it is introduced but it is considered heterologous due to its environment which is not natural, for example because it is under the control of a promoter which is not its natural promoter, or is introduced at a location which differs from its natural location.

As used herein, the term «payload» refers to any nucleic acid sequence that can be transferred into a bacterium by a bacterial delivery vehicle. The term «payload» may particularly refer to a plasmid, vector or cargo as defined hereafter. Preferably, the payload can be a phagemid or phasmid obtained from natural, evolved or engineered bacteriophage genome. The payload can also be composed in part of phagemid or phasmid obtained from a natural, evolved or engineered bacteriophage genome.

As used herein, the term "same payload" or "identical payload" are equivalent and refer to bacterial delivery vehicles containing payload with the same nucleic acid sequence enconding biological functions, i.e phage packaging, plasmid replication, plasmid selection, expression of proteins of interest in the target bacterium. In a first aspect, two payloads are considered as "same payload" when they have exactly the same nucleic acid sequence. In a second aspect, two payloads are considered as "same payload" when they encode the same biological functions. In this second aspect, the "same payload" may refer to two payloads having at least 70, 80, 90 or 95% of identity between each other. In other words, the "same payload" may refer to two payloads having at least 70, 80, 90 or 95% of identity between each other and encoding the same biological functions. In a particular aspect, the payloads have the same sequence except the tracer DNA sequences.

As used herein, the terms "plasmid", "vector" and "cargo" are equivalent and refer to a payload, such as DNA or RNA, transferred into a host cell using a bacterial delivery vehicle. A vector may comprise an origin of replication, a selectable marker, and optionally a suitable site for the insertion of a sequence or gene. A vector can be either a self-replicating extrachromosomal vector or a vector which integrates into a host genome. It can also comprise expression elements including, for example, a promoter, the correct translation initiation sequence such as a ribosomal binding site and a start codon, a termination codon, and a transcription termination sequence. A plasmid may also comprise other regulatory regions such as enhancers, silencers and boundary elements/insulators to direct the level of transcription of a given gene. Vectors capable of directing the expression of genes and/or nucleic acid sequence to which they are operatively linked can also be referred to herein as "expression vectors". There are several common types of vectors including plasmids, bacterial virus genomes, phagemids, virus genomes, cosmids, and artificial chromosomes. The plasmid can be a vector for stable or transient expression of a gene or sequence. In one embodiment, the plasmid of the invention is a phagemid or plasmid and refers to a vector that derives from both a plasmid and a bacterial virus genome. The plasmid may comprise a plasmid origin of replication (ori), a packaging signal and/or a tracer DNA sequence.

As used herein, the term "packaged payload" or "payload packaged into a delivery vehicle" refers to a payload which is contained into a delivery vehicle to promote its delivery into the targeted bacteria.

As used herein, the term "packaged plasmid" or "plasmid packaged into a bacterial virus particle" refers to a plasmid which is encapsidated into a proteinaceous envelope or capsid of a bacterial virus.

As used herein, the term "bacterial delivery vehicle" refers to any mean that allows the transfer of a payload into a cell, preferably a bacterial cell. There are several types of delivery vehicle encompassed by the present invention including, without limitation, bacteriophage scaffold, virus scaffold, protein-based or peptide-based delivery vehicle. Any combination of delivery vehicles is also encompassed by the present invention. The delivery vehicle can particularly refer to a bacteriophage derived scaffold and can be obtained from a natural, evolved or engineered capsid. The bacterial delivery vehicle can also be a proteinaceous envelope or capsid. In an embodiment, the delivery vehicle is the payload as bacteria are naturally competent to take up a payload from the environment on their own. In certain embodiments, the delivery system can be administered to a subject in need thereof. The bacterial cell can be an isolated cell (e.g. in a bacteria cell culture) or a cell associated with a subject in which inhibiting or promoting the expression of a target gene or a sequence of interest is desired.

As used herein, the terms "bacterial virus", "phage" or "bacteriophage" are used interchangeably and refer to a functional phage particle comprising a nucleic acid packaged into a proteinaceous envelope or capsid. The term also refers to portions of the bacterial virus, including, e.g., a head portion, or an assembly of phage components, which provide substantially the same functional activity.

As used herein, the terms "bacterial virus particle" or "virion" are equivalent and refer to a phage shape particle comprising a payload. The bacterial virus particle can be a proteinaceous envelope or capsid. Particularly, it refers to a bacterial virus particle devoid of a bacteriophage genome.

As used herein, the terms "proteinaceous envelope", "capsid", or "coat proteins" are equivalent and refer to the shape of the shell of proteins that protects the nucleic acid (i.e., genome) of a virus that is generally composed of structural units, or capsomers. Capsids are broadly classified according to their structure and shape known by the person skilled in the art. Preferably, they refer to bacteriophage capsids or coat proteins.

As used herein, the terms "different bacterial delivery vehicle", "different virus particles" or "distinct virus particles" or "different virus capsids" are equivalent and refer to the packaging of identical plasmids into bacterial delivery vehicles such as viral particles which are different, e.g. two different bacteriophage capsids.

As used herein, the terms "packaged" or "encapsulated" are equivalent and refer to the packaging of a payload, especially a plasmid, into a bacterial delivery vehicle. In one embodiment, the term "packaging" may be equivalent to the term "encapsidation" which refers to the packaging of a payload into a bacterial virus particle or capsid.

As used herein, the terms "orthogonal packaging sites" refer to packaging signals that are different and independent, meaning that they lead to separate packaging, i.e. into at least two different bacterial delivery vehicles such as capsids or bacterial virus particles.

The term "helper phage" as used herein refers to a virus being co-infected with a principal defective virus, in particular the payload to be packaged into a bacterial virus particle. The helper phage provides in trans the functions of which the first is deprived. In one embodiment, the packaged payload according to the invention may be produced using a helper phage strategy, well known to those skilled in the art. In this embodiment, the helper phage comprises all the genes coding for the structural and functional proteins that are indispensable for the payload according to the invention to be packaged or encapsidated (i.e. helper phage provides all the necessary gene products for particle formation). The helper phages are mutated wild-type phage containing a defective origin of replication or packaging signal, and hence, are inefficient in self-packaging, thus only bacterial virus particles carrying the deliverable nucleic acid (i.e., the payload or plasmid) will be produced. Helper phages may be chosen so that they cannot induce lysis of the host used for the particle production. It is understood by one skilled in the art that some bacteriophages are defective and need a helper phage for replication and/or packaging. Thus, according to the bacterial virus chosen in the present invention to prepare the bacterial virus particles, one skilled in the art would know if and which a helper phage is required.

As used herein, the terms "viral satellite genes" refers to genes derived from a satellite virus or satellite phage. Satellite phage are also known as a subviral agent and are composed of nucleic acid that depends on the co-infection of a host cell with a helper virus for all the morphogenetic functions, whereas for all its episomal functions (integration and immunity, multicopy plasmid replication) the satellite is completely autonomous from the helper. In one embodiment, the satellite genes can encode proteins that promote capsid size reduction of the helper phage, as described for the P4 Sid protein that controls the P2 capsid size to fit its smaller genome.

As used herein, the terms "promoter" and "transcriptional promoter" are equivalent and refer to a control region of a nucleic acid sequence at which transcription initiation and rate of transcription of the remainder of a nucleic acid sequence are controlled. A promoter may also contain sub-regions to which regulatory proteins and molecules may bind, such as RNA polymerase and other transcription factors. A promoter drives transcription of the nucleic acid sequence that it regulates. Herein, a promoter is considered to be "operably linked" when it is in a correct functional location and orientation in relation to a nucleic acid sequence it regulates to control ("drive") transcriptional initiation of that sequence.

As used herein, the term "origin of replication" refers to a particular sequence in a genome at which replication is initiated. This can either involve the replication of DNA in living organisms such as prokaryotes and eukaryotes, or that of DNA or RNA in viruses. Preferably, it refers to a bacterial origin of replication or a phage origin of replication that is present on the plasmid according to the invention.

As used herein, the term "selection marker" refers to a gene which is used to confirm the cloning of a gene or to confirm or ensure the presence of a plasmid in a bacterium. The selection marker can be a marker gene providing selectable phenotypes such as drug resistance, auxotrophy, resistance to cytotoxic agents, or surface protein expression. For example, an antibiotic-resistant gene, a gene allowing to overcome auxotrophy, a color-developing enzyme gene or a luminescent/fluorescent gene may be used. This confers a "selective advantage" to bacteria carrying such selection marker so as to be able to grow on medium supplied with antibiotics, heavy metals, or on medium without essential component such as amino acid.

As used herein, the term "inactivation" refers to the direct or indirect inhibition or decrease of the expression of a gene, or of the biological function of the protein, or of the production of specific gene products (protein or RNA), compared to a normal or previous condition. The regulation of the gene expression can be on the gene itself (i.e. cleavage, modifications), at the stage of transcription (i.e. using silencers or repressors), or using RNAi (e.g. siRNA, shRNA, endogenous microRNA or artificial microRNA), TALEN, ZFN, meganuclease or CRISPR/Cas system. In one embodiment, the CRISPR/Cas9 system is used to inactivate gene expression such as an antibiotic resistance gene, a virulence gene or a toxin gene present in the targeted bacteria.

As used herein, the term "bacterium" or "bacteria" refers to any prokaryotic microorganisms that exist as a single cell or in a cluster or aggregate of single cells. The term "bacterium" encompasses all variants of bacteria (e.g., endogenous bacteria, which naturally reside in a closed system, environmental bacteria or bacteria released for bioremediation or other efforts). Bacteria of the present disclosure include bacterial subdivisions of Eubacteria and Archaebacteria. Eubacteria can be further subdivided into Gram-positive and Gram-negative Eubacteria. Also included herein are those classified based on gross morphology alone (e.g., cocci, bacilli). In some embodiments, the bacteria are Gram-negative cells, and in other embodiments, the bacteria are Gram-positive cells.

As used herein, the terms "targeted bacteria" refers to the bacteria gender, species or strains that can be recognized by the bacterial delivery vehicle according to the invention and in which the bacterial delivery vehicle promote the introduction of the payload into said targeted bacteria. The specific spectrum of bacteriophages is known by the person skilled in the art, so that the person skilled in the art would know what would be the targeted bacteria according to the chosen phage. Preferably, the targeted bacteria are bacteria present in the human body (i.e., bacteria of the microbiota). Even more preferably, the targeted bacteria are bacteria presenting specific phenotypical characteristics of interest, such as but not limited to antibiotic-resistance.

As used herein, the terms "different bacteria" can refer to distinct bacteria species or can also refer to different strains or genetic variants or subtypes or genotypes of bacteria.

As used herein, the terms "containing the same payload" refers to the payload content of different bacterial delivery vehicles, meaning that identical payloads are packaged and contained into at least two different bacterial delivery vehicles. In an embodiment where the bacterial delivery vehicle is a bacterial virus, these terms mean that identical payloads are encapsidated and contained in at least two different bacterial virus capsids or particles (i.e., each bacteriophage has encapsidated and contains distinct copies of the same plasmid which present the same properties).

As used herein, the terms "antibiotic" and "antibacterial" are equivalent and refer to a type of antimicrobial active ingredient used in the treatment and prevention of bacterial infections. It can be a classical antibiotic that is produced by a microorganism that is antagonistic to the growth of other microorganisms and also encompasses more generally an antimicrobial agent that is capable of killing or inhibiting the growth of a microorganism, including chemically synthesized versions and variants of naturally occurring antibiotics.

As used herein, the term "antibiotic resistance gene" encompasses a gene, or the encoding portion thereof, which encodes a product or transcribes a functional RNA that confers antibiotic resistance. The antibiotic resistance gene may for example encode an enzyme which degrades an antibiotic, or an enzyme which modifies an antibiotic, or a pump such as an efflux pump, or a mutated target which suppresses the effect of the antibiotic.

As used herein, the terms "antibiotic resistant bacteria" refer to the ability of a bacterium to resist the effects of medication used against them.

The term "treatment" refers to any act intended to ameliorate the health status of patients or subjects such as therapy, prevention, prophylaxis and retardation of the infection. It designates both a curative treatment and/or a prophylactic treatment of a disease. A curative treatment is defined as a treatment resulting in cure or a treatment alleviating, improving and/or eliminating, reducing and/or stabilizing the symptoms of a disease or the suffering that it causes directly or indirectly. A prophylactic treatment comprises both a treatment resulting in the prevention of a disease and a treatment reducing and/or delaying the incidence of a disease or the risk of its occurrence. In certain embodiments, such term refers to the improvement or eradication of a disease, a disorder, an infection or symptoms associated with it. In other embodiments, this term refers to minimizing the spread or the worsening of an infection; e.g., resulting from antibiotic-resistant bacteria.

As used herein, the term "disorder" refers to an incorrectly functioning organ, part, structure, or system of the body. Preferably, the term disorder refers to a health disorder e.g. an illness that disrupts normal physical or mental functions. More preferably, the term disorder refers to a bacterial disease that is caused by or associated with bacteria or bacterial components that affect animals and/or humans. In a particular embodiment, the term disorder refers to the consequences of a bacterial infection, preferably by antibiotic resistant bacteria, or of a dysbiosis.

As used herein, the term "disease" refers to a disordered or incorrectly functioning organ, part, structure, or system of the body resulting from the effect of genetic or developmental errors, infection, poisons, nutritional deficiency or imbalance, toxicity, or unfavorable environmental factors. Preferably, the term disease refers to a bacterial disease that is caused by bacteria or bacterial components that affect animals and/or humans. In a particular embodiment, the term disease refers to the consequences of a bacterial infection, preferably by antibiotic resistant bacteria, or of a dysbiosis.

As used herein, a "pharmaceutical or veterinary composition" refers to a preparation of one or more of the active agents, such as the bacterial delivery vehicles containing the payload according to the invention, with optional other chemical components such as physiologically suitable carriers and excipients. The purpose of a pharmaceutical or veterinary composition is to facilitate administration of the active agent to an organism. Compositions of the present invention can be in a form suitable for any conventional route of administration or use. In one embodiment, the pharmaceutical or veterinary composition further comprises a pharmaceutically or veterinary acceptable vehicle.

A "pharmaceutically or veterinary acceptable vehicle" as referred to herein, is any known compound or combination of compounds that are known to those skilled in the art to be useful in formulating pharmaceutical or veterinary compositions. The pharmaceutically or veterinary acceptable vehicle may be a solid, and the composition may be in the form of a powder or tablet. The vehicle may also be an encapsulating material. In powders, the vehicle is a finely divided solid that is in admixture with the finely divided active agents according to the invention. In tablets, the active agent (e.g. the particle or system of the invention) may be mixed with a vehicle having the necessary compression properties in suitable proportions and compacted in the shape and size desired. The powders and tablets preferably contain up to 99% of the active agents. The pharmaceutical or veterinary vehicle may be a gel and the composition may be in the form of a cream or the like. However, the pharmaceutical or veterinary vehicle may alternatively be a liquid, and the pharmaceutical or veterinary composition is in the form of a solution. Liquid vehicles are used in preparing solutions, suspensions, emulsions, syrups, elixirs and pressurized compositions. Sterile liquid vehicles are useful in sterile liquid form compositions for enteral administration.

As used herein, a "prebiotic" refers to an ingredient that allows specific changes, both in the composition and/or activity in the gastrointestinal microbiota that may confer benefits upon the host. A prebiotic can be a comestible food or beverage or ingredient thereof. A prebiotic may be a selectively fermented ingredient. Prebiotics may include complex carbohydrates, amino acids, peptides, minerals, or other essential nutritional components for the survival of the bacterial composition.

As use herein, the term "probiotic" refers to a dietary supplement based on living microbes which, when taken in adequate quantitis, has a beneficial effect on the host organism by strengthening the intestinal ecosystem. A probiotic can comprise a non-pathogenic bacterial or fungal population, e.g., an immunomodulatory bacterial population, such as an anti-inflammatory bacterial population, with or without one or more prebiotics. They contain a sufficiently high number of living and active probiotic microorganisms that can exert a balancing action on gut flora by direct colonisation. It must be noted that, for purposes of the present description, the term "probiotic" is taken to mean any biologically active form of probiotic, preferably but not limited to lactobacilli, bifidobacteria, streptococci, enterococci, propionibacteria or saccaromycetes but even other microorganisms making up the normal gut flora, or also fragments of the bacterial wall or of the DNA of these microorganisms. These compositions are advantageous in being suitable for safe administration to humans and other mammalian subjects and are efficacious for the treatment, prevention, of a bacterial infection.

A "therapeutically effective amount" is an amount which, when administered to a subject, is the amount of active agent that is needed to treat the targeted disease or disorder, or to produce the desired effect, e.g. result in effective delivery of the bacterial delivery vehicles containing the payload to the targeted bacteria.

As used herein, the term "subject" or "patient" refers to an animal, preferably to a mammal, even more preferably to a human, including adult and child. However, the term "subject" also encompasses non-human animals, in particular mammals such as dogs, cats, horses, cows, pigs, sheep and non-human primates, among others.

The term "percentage of identity" in relation to sequences designates the level of identity or homology between said sequences and may be determined by techniques known per se in the art. Typically, the percentage of identity between two nucleic acid sequences is determined by means of computer programs such as GAP provided in the GCG program package (Program Manual for the Wisconsin Package, Version 8, August 1996, Genetics Computer Group, 575 Science Drive, Madison, Wis., USA 53711) (Needleman, S. B. and Wunsch, C.D., (1970), Journal of Molecular Biology, 48, 443-453). With settings adjusted to e.g., DNA sequences (particularly: GAP creation penalty of 5.0 and GAP extension penalty of 0.3), nucleic acid molecules may be aligned to each other using the Pileup alignment software available as part of the GCG program package. For comparing two amino acid sequences, one can use, for example, the tool "Emboss needle" for pairwise sequence alignment of proteins providing by EMBL-EBI and available on: ebi.ac.uk using default settings: (I) Matrix: BLOSUM62, (ii) Gap open: 10, (iii) gap extend: 0.5, (iv) output format: pair, (v) end gap penalty: false, (vi) end gap open: 10, (vii) end gap extend: 0.5.

Sequence identity between nucleotide or amino acid sequences can be determined by comparing an alignment of the sequences. When an equivalent position in the compared sequences is occupied by the same base or amino acid, then the molecules are identical at that position. Scoring an alignment as a percentage of identity is a function of the number of identical amino acids or bases at positions shared by the compared sequences. When comparing sequences, optimal alignments may require gaps to be introduced into one or more of the sequences to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties.

As used herein, the term "compatible size range" or "size requirement" refers to the size (kilobase) of a payload as disclosed herein that will be differentially packaged into the at least two different bacterial delivery vehicles. It is known by the person skilled in the art that, for identical payloads to be packaged into different capsids, they need to be a suitable substrate for each packaging mechanisms (e.g. headful or cohesive packaging mechanisms) and meet the size requirement to fit in the cavity of either of the at least two different bacterial virus capsids.

As used herein, "PFU" means plaque forming unit, as it is well defined in the art. Lytic bacteria viruses lyse the host cell, causing a zone of clearing (or plaque) on a culture plate. Theoretically, each plaque is formed by one phage and the number of plaques multiplied by the dilution factor is equal to the total number of phages in a test preparation.

As used herein, "CFU" means colony forming unit, as it is well defined in the art. This unit is used to estimate the number of viable bacteria or yeast in a sample, and refers to a mass of bacterial cells or yeast cells from the same bacterial or yeast progenitor.

"In vitro" refers to procedures that are performed outside of a cell. For example, purified enzymes or extracts of cells can be used to perform procedures in a vessel, such as a test tube.

"Ex vivo" refers to procedures that are performed outside of a multicellular organism, but use whole cells. For example, live cells from a subject, such as a human, can be cultured outside of the body and these cells can be used in testing procedures.

"In vivo" refers to procedures that are performed on a whole organism, such as a subject, including a human, such as in clinical trials. In vivo procedures can also be performed on non-human subjects, such as animal models.

The term "and/or" as used herein is to be taken as specific disclosure of each of the two specified features or components with or without the other. For example "A and/or B" is to be taken as specific disclosure of each of (i) A, (ii) B and (iii) A and B, just as if each is set out individually.

The term "a" or "an" can refer to one of or a plurality of the elements it modifies (e.g., "a reagent" can mean one or more reagents) unless it is contextually clear either one of the elements or more than one of the elements is described.

The term "about" as used herein in connection with any and all values (including lower and upper ends of numerical ranges) means any value having an acceptable range of deviation of up to +/−10% (e.g., +/−0.5%, +/−1%, +/−1.5%, +/−2%, +/−2.5%, +/−3%, +/−3.5%, +/−4%, +/−4.5%, +/−5%, +/−5.5%, +/−6%, +/−6.5%, +/−7%, +/−7.5%, +/−8%, +/−8.5%, +/−9%, +/−9.5%). The use of the term "about" at the beginning of a string of values modifies each of the values (i.e. "about 1, 2 and 3" refers to about 1, about 2 and about 3). Further, when a listing of values is described herein (e.g. about 50%, 60%, 70%, 80%, 85% or 86%) the listing includes all intermediate and fractional values thereof (e.g., 54%, 85.4%).

Payload of the Present Invention

The present invention relates to a payload suitable to be packaged into at least two different bacterial delivery vehicles and comprising at least two orthogonal bacterial viruses packaging sites.

To reproduce and survive, bacteria viruses need to package their genome inside their capsids. For this purpose, they evolved different sophisticated mechanisms differentiated by the nature of the phage termini: (i) single-stranded cohesive ends, (ii) circularly permuted direct terminal repeats, (iii) short, several hundred base pairs exact (non-permuted) direct terminal repeats, (iv) long, several thousand base pairs exact (non-permuted) direct terminal repeats, (v) terminal host DNA sequences, and (vi) covalently bound terminal proteins.

Two major packaging mechanisms relying on two different types of termini can be used according to the present invention which permit payload packaging into at least two different bacterial delivery vehicles are described hereafter.

Two different packaging sites using the same mechanism and relying on different terminases can also be used according to the present invention.

In an aspect of the disclosure, the at least two packaging sites are not comprised between a pair of transposable ends of a transposable element, especially Tn5 mosaic ends. In a very particular embodiment, the payload does not comprise any transposable end and/or transposable element.

Alternatively, the payload may also be the bacterial delivery vehicle as bacteria are naturally competent to take up a payload from the environment on their own.

Headful Packaging (Circularly Permuted Direct Terminal Repeats)

A headful packing system may feed the nucleic acid into the cavity of a phage prohead in a linear processive manner causing the head to expand until it reaches a limit where the DNA inside exerts pressure against the inner wall sufficient to stop progression. This may induce a conformational change in the head, which activates endonucleolytic cleavage of incoming DNA opening the way for attachment of phage tails to make infectious particles. Full heads may contain DNA molecules within a narrow size range. The capacity of the capsids may set a maximum size limitation on the packaged DNA. Representative headful packaging systems include, but are not limited to, P1, P7, T4, KVP40, P22 and (1)29.

Single-Stranded Cohesive Ends Packaging

The packaging machinery may use a specific site to initiate and terminate packaging (cos). It may employ highly specific cos sites to initiate and terminate packaging. These sites are cut by terminase leaving base overhangs (cos L and cos R) at the ends of the packaged DNA. In λ's natural rolling circle packaging substrate, cos sites are spaced closer together than the full packaging limit determined by head size. As a result, cos site spacing, and not head capacity, normally determines the length of virion DNA.

In one embodiment, the payload as disclosed hereafter can be packaged in the at least two different bacterial delivery vehicles by headful and/or cohesive packaging mechanisms.

The payload of the present invention is able to be packaged into at least two different bacterial delivery vehicles. This payload comprises:
 at least two orthogonal bacterial virus packaging sites that allow packaging into at least two different bacterial delivery vehicles;
 optionally, an origin of replication, preferably inactive in the bacteria targeted by the at least two different bacterial delivery vehicles;
 a nucleic acid sequence of interest under the control of a promoter.

Each of these features is described hereafter.

Payload Size

The size of the payload is selected so as to be suitable with the packaging into the considered bacterial delivery vehicles. Similarly, the considered bacterial delivery vehicles can be selected for being compatible, in particular having a size suitable with the payload to be packaged into such bacterial delivery vehicles.

In some embodiments, the payload disclosed herein comprises a size range of at least 100 base pairs (bp), at least 1 kilobase (kb), at least 2 kilobases (kb), at least 3 kilobases (kb), at least 4 kb, at least 5 kb, at least 10 kb, at least 15 kb, at least 20 kb, at least 25 kb, at least 30 kb, at least 35 kb, at least 40 kb, at least 45 kb, at least 50 kb, at least 55 kb, at least 60 kb, at least 65 kb, at least 70 kb, at least 75 kb, at least 80 kb, at least 85 kb, at least 90 kb, at least 95 kb, at least 100 kb, at least 105 kb, at least 110 kb, at least 115 kb, at least 120 kb, at least 125 kb, at least 130 kb, at least 135 kb, at least 140 kb, at least 145 kb, at least 150 kb, at least 175 kb, at least 200 kb, at least 225 kb, at least 250 kb, at least 275 kb, at least 300 kb, at least 325 kb, at least 350 kb, at least 375 kb, at least 400 kb, at least 425 kb, at least 450 kb, at least 475 kb, or at least 500 kb of nucleic acids.

Bacterial Virus Packaging Sites

For successful packaging into a bacterial delivery vehicle, the payload according to the invention comprises at least two different packaging signal sequences. For the same payload to be packaged into different capsids, it should to be a suitable substrate for each packaging mechanisms (i.e. headful or cohesive packaging mechanisms). This includes size requirement, no inhibition between packaging sites, and origin of replication compatible with both packaging systems.

Packaging sites include but are not limited to SPP1 (SPP1 pac site), P1 (P1 pac site), T1 (T1 pac site), T7 (T7 concatemer junction), lambda (λ cos site), P4 (P4 cos site), mu (mu pac site), P22 (P22 pac site), φ8 (φ8 pac site), Sf6 (Sf6 pac site), 149 (149 pac site), and A1 122 (A1 122-concatamer junction). Other types of packaging sites include HK97 packaging site, mEp235 packaging site, mEp043 packaging site, mEp234 packaging site, mEp505 packaging site, mEp506 packaging site, mEpX1 packaging site, mEpX2 packaging site, mEp390 packaging site, mEp460 packaging site, mEp213 packaging site, mEp237 packaging site, HK022 packaging site and phi80 packaging site. For most bacterial viruses, the packaging site is termed the pac site. In some cases, the packaging site is referred to as a concatemer junction (e.g. T7 concatemer junction). In every case, the packaging site is substantially isolated from sequences naturally occurring adjacent thereto in the bacteria virus genome.

For some bacterial viruses, the packaging site may be unknown. In these cases, pac sites can be determined by taking advantage of the property that plasmids containing a functional bacterial virus pac site are packaged. For example, the DNA sequences necessary for packaging by bacterial virus λ were determined by incorporating small restriction fragments of the)\, phage genomic DNA into a plasmid (Hohn, B 1983 PNAS USA 80:7456-7460). Using a similar strategy, the pac or cos sites for a number of bacterial viruses have been determined: λ (Miwa, T 1982 Gene 20:267-279); Mu (Groenen, MA and van de Putte, P 1985 Virology 144:520-522); filamentous bacteria viruses including fl, fd, M13, and Ike (Russel, M and Model, P 1989 J Virol 1989 63:3284-3295); P22 (Petri, J B and Schmieger, H 1990 Gene 88:47-55; Wu, H et al. 2002 Molec Microbiol 45:1631-1646); T7 (Chung, Y B and Hinkle, D C 1990 J Mo/Biol 216:927-938), and T3 (Hashimoto, C and Fujisawa, H 1992 Virology 187:788-795). The determination of DNA packaging strategy was also investigated by analysis of the terminase amino acid sequence of tailed-bacteriophage virions (Casjens and Gillcrease, Methods Mol Biol. 2009; 502: 91-111). A method to determine packaging sites and packaging mechanisms of phages using high-throughput sequencing data was described recently (Garneau J R, Depardieu F, Fortier L C, Bikard D and Monot M, Scientific Reports 2017 7(1):8292).

The payload according to the invention comprises at least two orthogonal packaging sites, preferably two orthogonal bacterial virus packaging sites, that allow packaging of the payload into at least two different bacterial delivery vehicles selected in the group consisting of pac sites, cos sites and concatemer junction sites or any other packaging sites with a different or unknown packaging mechanism or any combination thereof.

In one embodiment, the at least two different packaging sites can be at least two different cos sites (for example λ and P4 cos sites), at least two different pac sites (for example Mu, P1 and P22 pac sites) or at least two different concatemer junction sites (for example T7 and AI 122 concatemer junctions).

In another embodiment, the at least two different packaging sites can be at least one cos site and at least one pac site (for example λ cos site and P22 pac site), at least one cos site and at least one concatemer junction site (for example λ cos site and T7 concatemer junction), at least one pac site and at least one concatemer junction site (for example P22 pac site and T7 concatemer junction), or at least one cos site, at least one pac site and at least one concatemer junction site (for example λ cos site, P22 pac site and T7 concatemer junction).

Particularly, the payload according to the invention comprises at least two different packaging sites which can be selected in the group consisting of λ cos site, P4 cos site, SPP1 pac site, P1 pac site, T1 pac site, mu pac site, P22 pac site, φ8 pac site, Sf6 pac site, 149 pac site, T7 concatemer junction, A1 122-concatemer junction.

Preferably, the payload according to the invention comprises at least two different packaging sites which are λ cos site and P4 cos site. Alternatively, the payload according to the invention comprises λ cos site and P4 cos site, or λ cos site, P4 cos site and P1 pac site, or λ cos site, P4 cos site and T7 concatemer junction, or λ cos site, P4 cos site, P1 pac site and T7 concatemer junction.

In one embodiment, the payload according to the invention comprises at least two different packaging sites which are selected in the table 1 below. Preferably, the at least two different packaging sites are selected from the group consisting of SEQ ID No. 1, SEQ ID No. 2, SEQ ID No. 3, SEQ ID No. 4, SEQ ID No. 5 and SEQ ID No. 6 and any combination thereof.

Particularly, the payload according to the invention comprises a packaging site of SEQ ID No. 3 and at least one different packaging site selected from the group consisting of SEQ ID No. 1, SEQ ID No. 2, SEQ ID No. 4, SEQ ID No. 5 and SEQ ID No. 6.

In a particular embodiment, the payload according to the invention comprises at least three different packaging sites. Preferably the at least three packaging sites are selected from the group consisting of SEQ ID No. 1, SEQ ID No. 2, SEQ ID No. 3, SEQ ID No. 4, SEQ ID No. 5 and SEQ ID No. 6. Particularly, the payload according to the invention comprises three packaging sites of SEQ ID No. 1, SEQ ID No. 3 and SEQ. ID No. 5, respectively.

In a yet further embodiment, the at least two or at least three different packaging sites have at least 70% sequence identity, at least 75% sequence identity, at least 80% sequence identity, at least 85% sequence identity, at least 90% sequence identity, at least 95% sequence identity with any of the of the SEQ ID No. 1, SEQ ID No. 2, SEQ ID No. 3, SEQ ID No. 4, SEQ ID No. 5 and SEQ ID No. 6.

By different packaging sites, it is meant packaging sites having less than 80% of sequence identity between each other's, less than 75% of sequence identity, less than 70% of sequence identity, less than 65% of sequence identity, less than 60% of sequence identity, less than 55% of sequence identity, less than 50% of sequence identity, less than 45% of sequence identity, less than 40% of sequence identity, less than 35% of sequence identity, less than 30% of sequence identity, less than 25% of sequence identity, less than 20% of sequence identity, less than 15% of sequence identity, or less than 10% of sequence identity.

TABLE 1

Packaging sites DNA sequences

| SEQ ID | Name | Sequence |
|---|---|---|
| 1 | P1 Pac | ACCTGGGACGATCACAAGAAGAATTTTGCTCGCCTGGCG CGAGATGGTGGTTACACCATCGCACAGTATGCCGCCGAG TTTAATCTTAACCCTAATACCGCACGTCGTTATCTCCGTG CCTTCAAAGAGGACACCAGGACTACGGACAGCCGCAAG CCAAATAAGCCAGTCAGGAAGCCACTAAAAAGCATGATC ATTGATCACTCTAATGATCAACATGCAGGTGATCACATT GCGGCTGAAATAGCGGAAAAACAAAGAGTTAATGCCGTT GTCAGTGCCGCAGTCGAGAATGCGAAGCGCCAAAATAA GCGCATAAATGATCGTTCAGATGATCATGACGTGATCAC CCGCGCCCACCGGACCTTACGTGATCGCCTGGAACGCGA CACCCTGGATGATGATGGTGAACGCTTTGAGTTCGAAGT TGGCGATTACCTGATAGATAACGTTGAAGCGCGGAAGGC CGCGCGCGCTATGTTGCGTCGGTCCGGGGCCGATGTTCT GGAAACCACTCTTCTGGAAAAGTCTCTTTCTCATCTCCTT ATGCTGGAGAACGCCAGGGATACGTGTATTCGCCTGGTG CAGGAAATGCGCGATCAGCAAAAAGACGATGATGAAGG TACTCCGCCTGAATACCGTATCGCGAGCATGCTAAACAG CTGTTCCGCGCAGATAAGCAGCCTGATCAACACCATTTA CAGCATCCGGAATAACTATCGAAAAGAAAGCCGGGAGG CGGAAAAGCACGCTTTATCTATGGGGCAAGCTGGCATTG TTAAGCTGGCATA |
| 2 | Cos P4 | GCATGCGTTTTCCTGCCTCATTTTCTGCAAACCGCGCCAT TCCCGGCGCGGTCTGAGCGTGTCAGTGCAACTGCATTAA AACCGCCCCGCAAAGCGGGCGGGCGAGGCGGGGAAAGC ACCGCGCGCAAACCGACAAGTTAGTTAATTATTTGTGTA GTCAAAGTGCCTTCAGTACATACCTCGTTAATACATTGGA GCATAATGAAGAAAATCTATGGCTATGGTCCAAAACTG TCTTTTTTGATGGCACTATCCTGAAAAATATGCAAAAAAT AGATTGATGTAAGGTGGTTCTTGTCAGTGTCGCAAGATC CTTAAGAATTC |
| 3 | Cos lambda | CCAAAAAGCCTCGCTTTCAGCACCTGTCGTTTCCTTTCTT TTCAGAGGGTATTTTAAATAAAAACATTAAGTTATGACG AAGAAGAACGGAAACGCCTTAAACCGGAAAATTTTCATA AATAGCGAAAACCCGCGAGGTCGCCGCCCCGTAACCTGT CGGATCACCGGAAAGGACCCGTAAAGTGATAATGATTAT CATCTACATATCACAACGTGCGTAAAGG |
| 4 | Cos P2 | TAAGGTGCATTAAAACCGCCCCGTGAAGCGGGCGGGCGA GGCGGGGAAAGCACGGCGAGGCGGGGAAAGCACTGCGC GCTGACG |
| 5 | Cos 186 | TGTTTTGCATGCGTCAGGCTTGCCCGTTCTGGTTGTGCGT CGCCAGAGCTGGCGCGGCTCCAGAGTGGTCATGCAACTG CATTAAAACCGACCCATAAAGTGGGCAGGCGTGGCGGG GAAAGCATTGCGCGCCAGAGGTG |
| 6 | T7 concatemer junction | AGTCCATGCAGTTGGATTCCGTTAAGGTCGAGGGTGAAG TACTTGCTGACTTCCTTGAGGAACACATGATGCGTCCTAC GGTTGCTGCTACGCATATCATTGAGATGTCTGTGGGAGG AGTTGATGTGTACTCTGAGGACGATGAGGGTTACGGTAC GTCTTTCATTGAGTGGTGATTTATGCATTAGGACTGCATA GGGATGCACTATAGACCACGGATGGTCAGTTCTTTAAGT TACTGAAAAGACACGATAAATTAATACGACTCACTATAG GGAGAGGAGGGACGAAAGGTTACTATATAGATACTGAA TGAATACTTATAGAGTGCATAAAGTATGCATAATGGTGT ACCTAGAGTGACCTCTAAGAATGGTGATTATATTGTATTA GTATCACCTTAACTTAAGGACCAACATAAAGGGAGGAGA CTCATGTTCCGCTTATTGTTGAACCTACTGCGGCATAGAG TCACCTACCGATTTCTTGTGGTACTTTGTGCTGCCCTTGG GTACGCATCTCTTACTGGAGACCTCAGTTCACTGGAGTCT GTCGTTTGCTCTATACTCACTTGTAGCGATTAGGGTCTTC CTGACCGACTGATGGCTCACCGAGGGATTCAGCGGTATG ATTGCATCACACCACTTCATCCCTATAGAGTCAAGTCCTA AGGTATACCCATAAAGAGCCTCTAATGGTCTATCCTAAG GTCTATACCTAAAGATAGGCCATCCTATCAGTGTCACCTA AAGAGGGTCTTAGAGAGGGCTATGGAGTTCCTATAGGG TCCTTTAAAATATACCATAAAAATCTGAGTGACTATCTCA CAGTGTACGGACCTAAAGTTCCCCCATAGGGGGTACCTA AAGCCCAGCCAATCACCTAAAGTCAACCTTCGGTTGACC TTGAGGGTTCCCTAAGGGTTGGGGATGACCCTTGGGTTT GTCTTTGGGTGTTACCTTGAGTGTCTCTCTGTGTCCCTATC TGTTACAGTCTCCTAAAGTATCCTCCTAAAGTCACCTCCT AACGTCCATCCTAAAGCCAACACCTAAAGCCTACACCTA |

TABLE 1-continued

Packaging sites DNA sequences

| SEQ ID | Name | Sequence |
|---|---|---|
| | | AAGACCCATCAAGTCAACGCCTATCTTAAAGTTTAAACA TAAAGACCAGA |

Origin of Replication

The present invention envisions the use of origins of replication known in the art that have been identified from species-specific plasmid DNAs (e.g. ColE1, R1, pT181, pC194, pE194, RSF1010, pSC101, pMB1, R6K, RK2, p15a, pBBR1, pUC, pBR322 and the like), from bacterial virus (e.g. φX174, M13, F1 and P4) and from bacterial chromosomal origins of replication (e.g. oriC).

Bacteria-Specific Origins of Replication

Plasmid replication depends on host enzymes and on plasmid-controlled cis and trans determinants. For example, some plasmids have determinants that are recognized in almost all gram-negative bacteria and act correctly in each host during replication initiation and regulation. Other plasmids possess this ability only in some bacteria (Kues, U and Stahl, U 1989 Microbiol Rev 53:491-516).

Plasmids are replicated by three general mechanisms, namely theta type, strand displacement, and rolling circle (reviewed by Del Solar et al. 1998 Microbio and Molec Biol. Rev 62:434-464) that start at the origin of replication. This replication origins contain sites that are required for interactions of plasmid and/or host encoded proteins.

Origins of replication used on the payload of the invention may be moderate copy number, such as colE1 ori from pBR322 (15-20 copies per cell) or the R6K plasmid (15-20 copies per cell) or may be high copy number, e.g. pUC oris (500-700 copies per cell), pGEM oris (300-400 copies per cell), pTZ oris (>1000 copies per cell) or pBluescript oris (300-500 copies per cell).

In one embodiment, the bacterial origin of replication is selected in the group consisting of ColE1, pMB1 and variants (pBR322, pET, pUC, etc.), p15a, ColA, ColE2, pOSAK, pSC101, R6K, IncW (pSa etc.), IncFII, pT181, P1, F IncP, IncC, IncJ, IncN, IncP1, IncP4, IncQ, IncH11, RSF1010, CloDF13, NTP16, R1, f5, pPS10, pC194, pE194, BBR1, pBC1, pEP2, pWVO1, pLF1311, pAP1, pWKS1, pLS1, pLS11, pUB6060, pJD4, pIJ101, pSN22, pAMbeta1, pIP501, pIP407, ZM6100(Sa), pCU1, RA3, pMOL98, RK2/ RP4/RP1/R68, pB10, R300B, pRO1614, pRO1600, pECB2, pCM1, pFA3, RepFIA, RepFIB, RepFIC, pYVE439-80, R387, phasyl, RA1, TF-FC2, pMV158 and pUB113.

More preferably, the bacterial origin of replication is a E. coli origin of replication selected in the group consisting of ColE1, pMB1 and variants (pBR322, pET, pUC, etc.), p15a, ColA, ColE2, pOSAK, pSC101, R6K, IncW (pSa etc.), IncFII, pT181, P1, F IncP, IncC, IncJ, IncN, IncP1, IncP4, IncQ, IncH11, RSF1010, CloDF13, NTP16, R1, f5, pPS10.

More preferably, the bacterial origin of replication is selected in the group consisting of pC194, pE194, BBR1, pBC1, pEP2, pWVO1, pLF1311, pAP1, pWKS1, pLS1, pLS11, pUB6060, pJD4, 0.1101, pSN22, pAMbeta1, pIP501, pIP407, ZM6100(Sa), pCU1, RA3, pMOL98, RK2/ RP4/RP1/R68, pB10, R300B, pRO1614, pRO1600, pECB2, pCM1, pFA3, RepFIA, RepFIB, RepFIC, pYVE439-80, R387, phasyl, RA1, TF-FC2, pMV158 and pUB113.

Even more preferably, the bacterial origin of replication is ColE1.

Phage Origin of Replication

The payload according to the invention may comprise a phage replication origin which can initiate, with complementation of a complete phage genome, the replication of the payload for later encapsulation into the different bacterial delivery vehicles.

A phage origin of replication comprised in the payload of the invention can be any origin of replication found in a phage. Preferably, the phage origin of replication can be the wild-type or non-wildtype sequence of the M13, f1, φX174, P4, Lambda, P2, Lambda-like, HK022, mEP237, HK97, HK629, HK630, mEP043, mEP213, mEP234, mEP390, mEP460, mEPx1, mEPx2, phi80, mEP234, T2, T4, T5, T7, RB49, phiX174, R17, PRD1 P1-like, P2-like, P22, P22-like, N15 and N15-like bacteriophages.

More preferably, the phage origin of replication is selected in the group consisting of phage origins of replication of M13, f1, φX174, P4, and Lambda.

In a particular embodiment, the phage origin of replication is the P4 origin of replication.

Promoters

As known by the person skilled in the art, a promoter may be classified as strong or weak according to its affinity for RNA polymerase. The strength of a promoter may depend on whether initiation of transcription occurs at that promoter with high or low frequency. Different promoters with different strengths may be used in the present invention leading to different levels of gene/protein expression (e.g. the level of expression initiated from an mRNA originating from a weak promoter is lower than the level of expression initiated from a strong promoter).

It will be appreciated by those of ordinary skill in the art that a promoter sequence may be selected from a large number of known bacterial genes expressed by various bacterial species. Also, method of prokaryotic promoter prediction exists, and can be based on DNA stability analysis as described in Kanhere and Bansal (BMC Bioinformatics 2005, 6:1). The choice of promoter on the payload according to the present invention can thus be made based on the bacteria to target.

In some embodiments, a nucleic acid sequence of interest may be positioned under the control of a recombinant or heterologous promoter, which refers to a promoter that is not normally associated with the nucleic acid sequence of interest in its natural environment.

Examples of bacterial promoters for use in accordance with the present invention include, without limitation, positively regulated E. coli promoters such as positively regulated σ 70 promoters (e.g., inducible pBad/araC promoter, Lux cassette right promoter, modified lambda Prm promote, plac Or2-62 (positive), pBad/AraC with extra REN sites, pBad, P(Las) TetO, P(Las) CIO, P(Rh1), Pu, FecA, pRE, cadC, hns, pLas, pLux), a "s" promoter (e.g., Pdps), σ 32 promoters (e.g., heat shock) and σ 54 promoters (e.g., glnAp2); negatively regulated E. coli promoters such as negatively regulated σ 70 promoters (e.g., Promoter (PRM+), modified lambda Prm promoter, TetR-TetR-4C P(Las) TetO, P(Las) CIO, P(Lac) IQ, RecA_DlexO_D-Lac01, dapAp, FecA, Pspac-hy, pel, plux-cl, plux-lac, CinR, CinL, glucose controlled, modified Pr, modifed Prm+, FecA, Pcya, rec A (SOS), Rec A (SOS), EmrR_regulated, Betl_regulated, pLac_lux, pTet_Lac, pLac/Mnt, pTet/Mnt, LsrA/cI, pLux/cI, Lad, LacIQ, pLacIQ1, pLas/cI, pLas/Lux, pLux/Las, pRecA with LexA binding site, reverse BBa_R0011, pLacl/ara-1, pLacIq, rrnB PI, cadC, hns, PfhuA, pBad/araC, nhaA, OmpF, RcnR), σ S promoters (e.g., Lutz-Bujard LacO with alternative sigma factor σ 38), σ 32 promoters (e.g., Lutz-Bujard LacO with alternative sigma factor σ 32), σ 54 promoters (e.g., glnAp2); negatively regulated *B. subtilis* promoters such as repressible *B. subtilis* σ A promoters (e.g., Gram-positive IPTG-inducible, Xyl, hyper-spank), σ promoters, and the BioFAB promoters disclosed in Mutalik VK et al (Nature Methods, 2013, 10: 354-360, see in particular the supplementary data) as well as on the BioFAB website (biofab.synberc.org). Other inducible microbial promoters and/or bacterial promoters may be used in accordance with the present invention. An inducible promoter for use in accordance with the present disclosure may be induced by (or repressed by) one or more physiological condition(s), such as changes in pH, temperature, radiation, osmotic pressure, saline gradients, cell surface binding, and the concentration of one or more extrinsic or intrinsic inducing agent(s). The extrinsic inducer or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof.

Particularly preferred bacterial promoters for use in accordance with the present invention may be selected from constitutive promoters regulated by σ 70 such as the promoters of the Anderson collection (parts.igem.org): BBa_J23100, BBa_J23101, BBa_J23102, BBa_J23103, BBa_J23104, BBa_J23105, BBa_J23106, BBa_J23107, BBa_J23108, BBa_J23109, BBa_J23110, BBa_J23111, BBa_J23112, BBa_J23113, BBa_J23114, BBa_J23115, BBa_J23116, BBa_J23117, BBa_J23118, and BBa_J23119.

In some embodiments of the present invention, a promoter may or may not be used in conjunction with an "enhancer," which refers to a cis-acting regulatory sequence involved in the transcriptional activation of a nucleic acid sequence downstream of the promoter. The enhancer may be located at any functional location before or after the promoter.

Terminators

In some embodiments, the payload may comprise a terminator sequence, or terminator. A "terminator," as used herein, is a nucleic acid sequence that causes transcription to stop. A terminator may be unidirectional or bidirectional. It is comprised of a DNA sequence involved in specific termination of an RNA transcript by an RNA polymerase. A terminator sequence prevents transcriptional activation of downstream nucleic acid sequences by upstream promoters. Thus, in certain embodiments, a terminator that ends the production of an RNA transcript is contemplated. A terminator may be necessary in vivo to achieve desirable gene/protein expression levels.

The most commonly used type of terminator is a forward terminator. When placed downstream of a nucleic acid sequence of interest that is usually transcribed, a forward transcriptional terminator will cause transcription to abort. In some embodiments, bidirectional transcriptional terminators are provided, which usually cause transcription to terminate on both the forward and reverse strand. In some embodiments, reverse transcriptional terminators are provided, which usually terminate transcription on the reverse strand only. In prokaryotic systems, terminators usually fall into two categories (1) rho-independent terminators and (2) rho-dependent terminators. Rho-independent terminators are generally composed of palindromic sequence that forms a stem loop rich in G-C base pairs followed by a string of uracil bases.

Terminators for use in accordance with the present invention include any terminator of transcription described herein or known to one of ordinary skill in the art. Examples of terminators include, without limitation, the termination sequences of genes such as, for example, the bovine growth hormone terminator, and viral termination sequences such as, for example, the TO terminator, the TE terminator, Lambda T1 and the T1T2 terminator found in bacterial systems. In some embodiments, the termination signal may be a sequence that cannot be transcribed or translated, such as those resulting from a sequence truncation.

Terminators for use in accordance with the present invention also include terminators disclosed in Chen Y J et al (2013, Nature Methods, 10: 659-664), and the BioFAB terminators disclosed in Cambray G et al (Nucl Acids Res, 2013, 41(9): 5139-5148).

Sequence of Interest Under the Control of the Promoter

According to the invention, the payload comprises a sequence of interest under the control of a promoter.

In one embodiment, the sequence of interest is a programmable nuclease circuits to be delivered to the targeted bacteria. This programmable nuclease circuit may be able to mediate in vivo sequence-specific elimination of bacteria that contain a target gene of interest (e.g. a gene that is harmful to humans). Some embodiments of the present disclosure relate to engineered variants of the Type II CRISPR-Cas (Clustered Regularly Interspaced Short Palindromic Repeats-CRISPR-associated) system of *Streptococcus pyogenes*. Other programmable nucleases that can be used include other CRISPR-Cas systems, engineered TALEN (Transcription Activator-Like Effector Nuclease) variants, engineered zinc finger nuclease (ZFN) variants, natural, evolved or engineered meganuclease or recombinase variants, and any combination or hybrids of programmable nucleases. Thus, the engineered autonomously distributed circuits provided herein may be used to selectively cleave DNA encoding a gene of interest such as, for example, a toxin gene, a virulence factor gene, an antibiotic resistance gene, a remodeling gene or a modulatory gene (cf. WO2014124226 and US2015/0064138).

Other sequences of interest, preferably programmable, can be added to the payload so as to be delivered to targeted bacteria. Preferably, the sequence of interest added to the payload leads to cell death of the targeted bacteria. For example, the nucleic acid sequence of interest added to the payload may encode holins or toxins.

Alternatively, the sequence of interest circuit added to the payload does not lead to bacteria death. For example, the sequence of interest may encode reporter genes leading to a luminescence or fluorescence signal, or being able to elicit an immune response. Alternatively, the sequence of interest may comprise proteins and enzymes achieving a useful function such as modifying the metabolism of the bacteria or the composition of its environment and/or such as producing a therapeutic effect.

In a particular embodiment, the nucleic sequence of interest is selected in the group consisting of a Cas nuclease, a Cas9 nuclease, a guide RNA, a single guide RNA (sgRNA), a CRISPR locus, a gene expressing an enzyme such as a nuclease or a kinase, a TALEN, a ZFN, a meganuclease, a recombinase, a bacterial receptor, a membrane protein, a structural protein, a secreted protein, resistance to an antibiotic or to a drug in general, a gene expressing a toxic protein or a toxic factor and a gene expressing a virulence protein or a virulence factor or any combination thereof.

Toxin

In a particular embodiment, the payload according to the invention comprises a sequence of interest that encodes a bacteriocin, which can be a proteinaceous toxin produced by bacteria to kill or inhibit growth of other bacteria. Bacteriocins are categorized in several ways, including producing strain, common resistance mechanisms, and mechanism of killing. Such bacteriocin had been described from gram negative bacteria (e.g. microcins, colicin-like bacteriocins and tailocins) and from gram positive bacteria (e.g. Class I, Class II, Class III or Class IV bacteriocins).

In one embodiment, the payload according to the invention further comprises a sequence of interest encoding a toxin selected in the group consisting of microcins, colicin-like bacteriocins, tailocins, Class I, Class II, Class III and Class IV bacteriocins.

In a particular embodiment, the corresponding immunity polypeptide (i.e. anti-toxin) may be used to protect bacterial cells (see review by Cotter et al., Nature Reviews Microbiology 11: 95, 2013, which is hereby incorporated by reference in its entirety) for payload production and packaging purpose but is absent in the pharmaceutical composition and in the targeted bacteria in which the payload of the invention is delivered.

CRISPR-Cas

The CRISPR system contains two distinct elements, i.e. i) an endonuclease, in this case the CRISPR associated nuclease (Cas or "CRISPR associated protein") and ii) a guide RNA. The guide RNA is in the form of a chimeric RNA which consists of the combination of a CRISPR (RNAcr) bacterial RNA and a RNAtracr (trans-activating RNA CRISPR) (Jinek et al., Science 2012). The gRNA combines the targeting specificity of the cRNA corresponding to the "spacing sequences" that serve as guides to the Cas proteins, and the conformational properties of the Rtracr in a single transcript. When the gRNA and the Cas protein are expressed simultaneously in the cell, the target genomic sequence can be permanently modified or interrupted. The modification is advantageously guided by a repair matrix.

The CRISPR system includes two main classes depending on the nuclease mechanism of action:
   Class 1 is made of multi-subunit effector complexes and includes type I, III and IV
   Class 2 is made of single-unit effector modules, like Cas9 nuclease, and includes type II (II-A,II-B,II-C,II-C variant), V (V-A,V-B,V-C,V-D,V-E,V-U1,V-U2,V-U3,V-U4,V-U5) and VI (VI-A,VI-B1,VI-B2,VI-C,VI-D)

The sequence of interest according to the present invention comprises a nucleic acid sequence encoding Cas protein. A variety of CRISPR enzymes are available for use as a sequence of interest on the payload according to the present invention. In some embodiments, the CRISPR enzyme is a Type II CRISPR enzyme. In some embodiments, the CRISPR enzyme catalyzes DNA cleavage. In some other embodiments, the CRISPR enzyme catalyzes RNA cleavage. In one embodiment, the CRISPR enzymes may be coupled to a sgRNA. In certain embodiments, the sgRNA targets a gene selected in the group consisting of an antibiotic resistance gene, virulence protein or factor gene, toxin protein or factor gene, a bacterial receptor gene, a membrane protein gene, a structural protein gene, a secreted protein gene and a gene expressing resistance to a drug in general.

Non-limiting examples of Cas proteins as part of a multi-subunit effector or as a single-unit effector include Cas1, Cas1B, Cas2, Cas3, Cas4, Cas5, Cas6, Cas7, Cas8, Cas9 (also known as Csn1 and Csx12), Cas10, Cas11 (SS), Cas12a (Cpf1), Cas12b (C2c1), Cas12c (C2c3), Cas12d (CasY), Cas12e (CasX), C2c4, C2c8, C2c5, C2c10, C2c9, Cas13a (C2c2), Cas13b (C2c6), Cas13c (C2c7), Cas13d, Csa5, Csc1, Csc2, Cse1, Cse2, Csy1, Csy2, Csy3, Csf1, Csf2, Csf3, Csf4, Csm2, Csm3, Csm4, Csm5, Csm6, Cmr1, Cmr3, Cmr4, Cmr5, Cmr6, Csn2, Csb1, Csb2, Csb3, Csx17, Csx14, Csx10, Csx16, CsaX, Csx13, Csx1, Csx15, SdCpf1, CmtCpf1, TsCpf1, CmaCpf1, PcCpf1, ErCpf1, FbCpf1, UbcCpf1, AsCpf1, LbCpf1, homologues thereof, orthologues thereof, variants thereof, or modified versions thereof. In some embodiments, the CRISPR enzyme cleaves both strands of the target nucleic acid at the Protospacer Adjacent Motif (PAM) site.

In a particular embodiment, the CRISPR enzyme is any Cas9 protein, for instance any naturally-occurring bacterial Cas9 as well as any variants, homologs or orthologues thereof.

By "Cas9" is meant a protein Cas9 (also called Csn1 or Csx12) or a functional protein, peptide or polypeptide fragment thereof, i.e. capable of interacting with the guide RNA(s) and of exerting the enzymatic activity (nuclease) which allows it to perform the double-strand cleavage of the DNA of the target genome. "Cas9" can thus denote a modified protein, for example truncated to remove domains of the protein that are not essential for the predefined functions of the protein, in particular the domains that are not necessary for interaction with the gRNA (s).

The sequence encoding Cas9 (the entire protein or a fragment thereof) as used in the context of the invention can be obtained from any known Cas9 protein (Fonfara et al., 2014; Koonin et al., 2017). Examples of Cas9 proteins useful in the present invention include, but are not limited to, Cas9 proteins of *Streptococcus pyogenes* (SpCas9), *Streptococcus thermophiles* (St1Cas9, St3Cas9), *Streptococcus mutans, Staphylococcus aureus* (SaCas9), *Campylobacter jejuni* (CjCas9), *Francisella novicida* (FnCas9) and *Neisseria meningitides* (NmCas9).

The sequence encoding Cpf1 (Cas12a) (the entire protein or a fragment thereof) as used in the context of the invention can be obtained from any known Cpf1 (Cas12a) protein (Koonin et al., 2017). Examples of Cpf1 (Cas12a) proteins useful in the present invention include, but are not limited to, Cpf1(Cas12a) proteins of *Acidaminococcus* sp, *Lachnospiraceae bacteriu* and *Francisella novicida*.

The sequence encoding Cas13a (the entire protein or a fragment thereof) as used in the context of the invention can be obtained from any known Cas13a (C2c2) protein (Abudayyeh et al., 2017). Examples of Cas13a (C2c2) proteins useful in the present invention include, but are not limited to, Cas13a (C2c2) proteins of *Leptotrichia wadei* (LwaCas13a).

The sequence encoding Cas13d (the entire protein or a fragment thereof) as used in the context of the invention can be obtained from any known Cas13d protein (Yan et al., 2018). Examples of Cas13d proteins useful in the present invention include, but are not limited to, Cas13d proteins of *Eubacterium siraeum* and *Ruminococcus* sp.

In a particular embodiment, the nucleic sequence of interest is a CRISPR/Cas9 system for the reduction of gene expression or inactivation a gene selected in the group consisting of an antibiotic resistance gene, virulence factor or protein gene, toxin factor or protein gene, a gene expressing a bacterial receptor, a membrane protein, a structural protein, a secreted protein, and a gene expressing resistance to a drug in general.

In one embodiment, the CRISPR system is used to target and inactivate a virulence factor. A virulence factor can be any substance produced by a pathogen that alter host-pathogen interaction by increasing the degree of damage done to the host. Virulence factors are used by pathogens in many ways, including, for example, in cell adhesion or colonization of a niche in the host, to evade the host's immune response, to facilitate entry to and egress from host cells, to obtain nutrition from the host, or to inhibit other physiological processes in the host. Virulence factors can include enzymes, endotoxins, adhesion factors, motility factors, factors involved in complement evasion, and factors that promote biofilm formation. For example, such targeted virulence factor gene can be *E. coli* virulence factor gene such as, without limitation, EHEC-H1yA, Stx1 (VT1), Stx2 (VT2), Stx2a (VT2a), Stx2b (VT2b), Stx2c (VT2c), Stx2d (VT2d), Stx2e (VT2e) and Stx2f (VT2f), Stx2h (VT2h), fimA, fimF, fimH, neuC, kpsE, sfa, foc, iroN, aer, iha, papC, papGI, papGII, papGIII, h1yC, cnf1, hra, sat, ireA, usp ompT, ibeA, malX, fyuA, irp2, traT, afaD, ipaH, eltB, estA, bfpA, eaeA, espA, aaiC, aatA, TEM, CTX, SHV, csgA, csgB, csgC, csgD, csgE, csgF, csgG, csgH, T1SS, T2SS, T3SS, T4SS, T5SS, T6SS (secretion systems). For example, such targeted virulence factor gene can be *Shigella dysenteriae* virulence factor gene such as, without limitation, stx1 and stx2. For example, such targeted virulence factor gene can be *Yersinia pestis* virulence factor gene such as, without limitation, yscF (plasmid-borne (pCD1) T3SS external needle subunit). For example, such targeted virulence factor gene can be *Francisella tularensis* virulence factor gene such as, without limitation, fs1A. For example, such targeted virulence factor gene can be *Bacillus anthracia* virulence factor gene such as, without limitation, pag (Anthrax toxin, cell-binding protective antigen). For example, such targeted virulence factor gene can be *Vibrio cholera* virulence factor gene such as, without limitation, ctxA and ctxB (cholera toxin), tcpA (toxin co-regulated pilus), and toxT (master virulence regulator). For example, such targeted virulence factor gene can be *Pseudomonas aeruginosa* virulence factor genes such as, without limitation, pyoverdine (e.g., sigma factor pvdS, biosynthetic genes pvdL, pvdl, pvdJ, pvdH, pvdA, pvdF, pvdQ, pvdN, pvdM, pvdO, pvdP, transporter genes pvdE, pvdR, pvdT, opmQ), siderophore pyochelin (e.g., pchD, pchC, pchB, pchA, pchE, pchF and pchG, and toxins (e.g., exoU, exoS and exoT). For example, such targeted virulence factor gene can be *Klebsiella pneumoniae* virulence factor genes such as, without limitation, fimA (adherence, type I fimbriae major subunit), and cps (capsular polysaccharide). For example, such targeted virulence factor gene can be *Acinetobacter baumannii* virulence factor genes such as, without limitation, ptk (capsule polymerization) and epsA (assembly). For example, such targeted virulence factor gene can be *Salmonella enterica Typhi* virulence factor genes such as, without limitation, MIA (invasion, SPI-1 regulator), ssrB (SPI-2 regulator), and those associated with bile tolerance, including efflux pump genes acrA, acrB and to 1C. For example, such targeted virulence factor gene can be *Fusobacterium nucleatum* virulence factor genes such as, without limitation, FadA and TIGIT. For example, such targeted virulence factor gene can be *Bacteroides fragilis* virulence factor genes such as, without limitation, bft.

In another embodiment, the CRISPR/Cas9 system is used to target and inactivate an antibiotic resistance gene such as, without limitation, GyrB, ParE, ParY, AAC(1), AAC(2'), AAC(3), AAC(6'), ANT(2"), ANT(3"), ANT(4'), ANT(6), ANT(9), APH(2"), APH(3"), APH(3'), APH(4), APH(6), APH(7"), APH(9), ArmA, RmtA, RmtB, RmtC, Sgm, AER, BLA1, CTX-M, KPC, SHV, TEM, BlaB, CcrA, IMP, NDM, VIM, ACT, AmpC, CMY, LAT, PDC, OXA β-lactamase, mecA, Omp36, OmpF, PIB, bla (blal, blaR1) and mec (mecl, mecR1) operons, Chloramphenicol acetyltransferase (CAT), Chloramphenicol phosphotransferase, Ethambutol-resistant arabinosyltransferase (EmbB), MupA, MupB, Integral membrane protein MprF, Cfr 23 S rRNA methyltransferase, Rifampin ADP-ribosyltransferase (Arr), Rifampin glycosyl-transferase, Rifampin monooxygenase, Rifampin phosphotransferase, DnaA, RbpA, Rifampin-resistant beta-subunit of RNA polymerase (RpoB), Erm 23 S rRNA methyltransferases, Lsa, MsrA, Vga, VgaB, Streptogramin Vgb lyase, Vat acetyltransferase, Fluoroquinolone acetyltransferase, Fluoroquinolone-resistant DNA topoisomerases, Fluoroquinolone-resistant GyrA, GyrB, ParC, Quinolone resistance protein (Qnr), FomA, FomB, FosC, FosA, FosB, FosX, VanA, VanB, VanD, VanR, VanS, Lincosamide nucleotidyl-transferase (Lin), EreA, EreB, GimA, Mgt, Ole, Macrolide phosphotransferases (MPH), MefA, MefE, Mel, Streptothricin acetyltransferase (sat), Sul1, Sul2, Sul3, sulfonamide-resistant FolP, Tetracycline inactivation enzyme TetX, TetA, TetB, TetC, Tet30, Tet31, TetM, TetO, TetQ, Tet32, Tet36, MacAB-To1C, MsbA, MsrA, VgaB, EmrD, EmrAB-To1C, NorB, GepA, MepA, AdeABC, AcrD, MexAB-OprM, mtrCDE, EmrE, adeR, acrR, baeSR, mexR, phoPQ, mtrR, or any antibiotic resistance gene described in the Comprehensive Antibiotic Resistance Database (card.mcmaster.ca)

In another embodiment, the CRISPR/Cas9 system is used to target and inactivate a bacterial toxin gene. Bacterial toxin can be classified as either exotoxins or endotoxins. Exotoxins are generated and actively secreted; endotoxins remain part of the bacteria. The response to a bacterial toxin can involve severe inflammation and can lead to sepsis. Such toxin can be for example Botulinum neurotoxin, Tetanus toxin, *Staphylococcus* toxins, Diphtheria toxin, Anthrax toxin, Alpha toxin, Pertussis toxin, Shiga toxin, Heat-stable enterotoxin (*E. coli* ST), colibactin, BFT (*B. fragilis* toxin) or any toxin described in Henkel et al., (Toxins from Bacteria in EXS. 2010; 100: 1-29).

Selection Marker

In one embodiment, the payload according to the invention may further comprise a selection marker. In a particular embodiment, the selection marker provides a selective advantage to the bacterial cell infected by the payload, such as resistance to antibiotics, resistance to heavy metals, complementing a host auxotrophy and/or exhibiting fluorescent or luminescent proteins.

The inclusion of the suitable selectable marker gene in a payload allows testing and/or detection for successful delivery of the payload according to the invention. The payload according to the invention may comprise one or more nucleic acid sequences encoding selectable marker such as auxotrophic markers (e.g., LEU2, URA3, TRP 1, HIS3, DapA or ThyA) (Peubez et al, 2010), detectable labels such as fluorescent or luminescent proteins (e.g., GFP, eGFP, DsRed, CFP, YFP), or protein conferring resistance to a chemical/toxic compound (e.g., MGMT gene conferring resistance to temozolomide, kanamycin resistance, chloramphenicol resistance, etc.) or any combinations thereof. These markers can be used to select or detect host cells comprising the vector according to the invention and can be easily chosen by the skilled person according to the host cell.

For most purposes, an antibiotic resistance gene is a commonly used selection marker to facilitate molecular biology cloning of the payload and to allow the detection or selection of bacteria transformed by such payload. Antibiotic resistance genes are well known in the art and include but are not limited to ampicillin resistance (Amp), chloramphenicol resistance (Cm), tetracycline resistance (Tet), kanamycin resistance (Kan), hygromycin resistance (Qiyg or hph genes), and zeomycin resistance (Zeo).

Alternatively, antibiotic-free selection systems have been suggested. Such antibiotic-free selection systems include bacterial toxin-antitoxin systems [Engelberg-Kulka, H. and Glaser, G., Annu. Rev. Microbiol. 53 (1999) 43-70] and genes responsible for resistance against heavy metals, such as tellurium [Silver, S, and Phung, L. T., Annu. Rev. Microbiol. 50 (1996) 753-789], and systems, in which the payload encodes a gene complementing a host auxotrophy [Wang, M. D., et al., J. Bacteriol. 169 (1987) 5610-5614].

Auxotrophic marker selection in bacteria has previously been described. See, for example, U.S. Pat. Nos. 4,920,048, 5,691,185, 6,291,245, 6,413,768, 6,752,994, Struhl et al. ((1976) PNAS USA 73; 1471-1475); MacCormick, C. A., et al., ((1995) *FEMS Microbiol. Lett.* 127:105-109); Dickely et al. ((1995), *Mol. Microbiol.* 15:839-847); Sørensen et al., ((2000) *Appl. Environ. Microbiol.* 66:1253-1258); Fiedler & Skerra, ((2001) Gene 274: 111-118).

In a preferred embodiment, the payload according to the invention comprises an auxotrophic marker.

Targeted Bacteria

The bacteria targeted by bacterial delivery vehicles can be any bacteria present in a mammal organism. It can be any commensal, symbiotic or pathogenic bacteria of the microbiota or microbiome.

A microbiome may comprise of a variety of endogenous bacterial species, any of which may be targeted in accordance with the present disclosure. In some embodiments, the genus and/or species of targeted endogenous bacterial cells may depend on the type of bacteriophages being used for preparing the bacterial virus particles. For example, some bacteriophages exhibit tropism for, or preferentially target, specific host species of bacteria. Other bacteriophages do not exhibit such tropism and may be used to target a number of different genus and/or species of endogenous bacterial cells.

Examples of bacterial cells include, without limitation, cells from bacteria of the genus *Yersinia, Escherichia, Klebsiella, Acinetobacter, Bordetella, Neisseria, Aeromonas, Franciesella, Corynebacterium, Citrobacter, Chlamydia, Hemophilus, Brucella, Mycobacterium, Legionella, Rhodococcus, Pseudomonas, Helicobacter, Vibrio, Bacillus, Erysipelothrix, Salmonella, Streptomyces, Streptococcus, Staphylococcus, Bacteroides, Prevotella, Clostridium, Bifidobacterium, Clostridium, Brevibacterium, Lactococcus, Leuconostoc, Actinobacillus, Selnomonas, Shigella, Zymonas, Mycoplasma, Treponema, Leuconostoc, Corynebacterium, Enterococcus, Enterobacter, Pyrococcus, Serratia, Morganella, Parvimonas, Fusobacterium, Actinomyces, Porphyromonas, Micrococcus, Bartonella, Borrelia, Brucelia, Campylobacter, Chlamydophilia, Cutibacterium, Propionibacterium, Gardnerella, Ehrlichia, Haemophilus, Leptospira, Listeria, Mycoplasma, Nocardia, Rickettsia, Ureaplasma,* and *Lactobacillus,* and any mixture thereof.

Thus, delivery vehicles may target (e.g., specifically target) a bacterial cell from any one or more of the foregoing genus of bacteria to specifically deliver the payload according to the invention.

Preferably, the targeted bacteria can be selected from the group consisting of *Yersinia* spp., *Escherichia* spp., *Klebsiella* spp., *Acinetobacter* spp., *Pseudomonas* spp., *Helicobacter* spp., *Vibrio* spp., *Salmonella* spp., *Streptococcus* spp., *Staphylococcus* spp., *Bacteroides* spp., *Clostridium* spp., *Shigella* spp., *Enterococcus* spp., *Enterobacter* spp., *Listeria* spp., *Cutibacterium* spp., *Propionibacterium* spp., *Fusobacterium* spp., *Porphyromonas* spp. and *Gardnerella* spp.

In some embodiments, bacterial cells of the present invention are anaerobic bacterial cells (e.g., cells that do not require oxygen for growth). Anaerobic bacterial cells include facultative anaerobic cells such as but not limited to *Escherichia coli, Shewanella oneidensis, Gardnerella vaginalis* and *Listeria*. Anaerobic bacterial cells also include obligate anaerobic cells such as, for example, *Bacteroides, Clostridium, Cutibacterium, Propionibacterium, Fusobacterium* and *Porphyromonas* species. In humans, anaerobic bacteria are most commonly found in the gastrointestinal tract. In some particular embodiment, the targeted bacteria are thus bacteria most commonly found in the gastrointestinal tract. Bacteriophages used for preparing the bacterial virus particles, and then the bacterial virus particles, may target (e.g., to specifically target) anaerobic bacterial cells according to their specific spectra known by the person skilled in the art to specifically deliver the payload.

In some embodiments, the targeted bacterial cells are, without limitation, *Bacteroides thetaiotaomicron, Bacteroides fragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus actinobycetemcomitans, cyanobacteria, Escherichia coli, Helicobacter pylori, Selnomonas ruminatium, Shigella sonnei, Zymomonas mobilis, Mycoplasma mycoides, Treponema denticola, Bacillus thuringiensis, Staphilococcus lugdunensis, Leuconostoc oenos, Corynebacterium xerosis, Lactobacillus plantarum, Lactobacillus rhamnosus, Lactobacillus casei, Lactobacillus acidophilus, Enterococcus faecalis, Bacillus coagulans, Bacillus cereus, Bacillus popillae, Synechocystis* strain PCC6803, *Bacillus liquefaciens, Pyrococcus abyssi, Selenomonas nominantium, Lactobacillus hilgardii, Streptococcus fetus, Lactobacillus pentosus, Bacteroides fragilis, Staphylococcus epidermidis, Streptomyces phaechromogenes, Streptomyces ghanaenis, Klebsiella pneumoniae, Enterobacter cloacae, Enterobacter aerogenes, Serratia marcescens, Morganella morganii, Citrobacter freundii, Propionibacterium freudenreichii, Pseudomonas aerigunosa, Parvimonas micra, Prevotella intermedia, Fusobacterium nucleatum, Prevotella nigrescens, Actinomyces israelii, Porphyromonas endodontalis, Porphyromonas gingivalis Micrococcus luteus, Bacillus megaterium, Aeromonas hydrophila, Aeromonas caviae, Bacillus anthracia, Bartonella henselae, Bartonella Quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Campylobacter coli, Campylobacter fetus, Chlamydia pneumoniae, Chlamydia trachomatis, Chlamydophila psittaci, Clostridium botulinum, Clostridium difficile, Clostridium perfringens, Clostridium tetani, Corynebacterium diphtheria, Cutibacterium acnes* (formerly *Propionibacterium acnes), Ehrlichia canis, Ehrlichia chaffeensis, Enterococcus faecium, Francisella tularensis, Haemophilus influenza, Legionella pneumophila, Leptospira interrogans, Leptospira santarosai, Leptospira weilii, Leptospira noguchii,*

Listeria monocytogenes, Mycobacterium leprae, Mycobacterium tuberculosis, Mycobacterium ulcerans, Mycoplasma pneumonia, Neisseria gonorrhoeae, Neisseria meningitides, Nocardia asteroids, Rickettsia rickettsia, Salmonella enteritidis, Salmonella typhi, Salmonella paratyphi, Salmonella typhimurium, Shigella flexnerii, Shigella dysenteriae, Staphylococcus saprophyticus, Streptococcus pneumoniae, Streptococcus pyogenes, Gardnerella vaginalis, Streptococcus viridans, Treponema pallidum, Ureaplasma urealyticum, Vibrio cholera, Vibrio parahaemolyticus, Yersinia pestis, Yersinia enterocolitica, Yersinia pseudotuberculosis, Actinobacter baumanii, Pseudomonas aerigunosa, and a mixture thereof, preferably the bacteria of interest are selected from the group consisting of Escherichia coli, Enterococcus faecium, Staphylococcus aureus, Klebsiella pneumoniae, Acinetobacter baumanii, Pseudomonas aeruginosa, Enterobacter cloacae, and Enterobacter aerogenes, and a mixture thereof.

In one embodiment, the targeted bacteria are Escherichia coli.

Thus, bacteriophages used for preparing the bacterial virus particles, and then the bacterial virus particles, may target (e.g., specifically target) a bacterial cell from any one or more of the foregoing genus and/or species of bacteria to specifically deliver the payload.

In one embodiment, the targeted bacteria are pathogenic bacteria. The targeted bacteria can be virulent bacteria.

The targeted bacteria can be antibacterial resistance bacteria, preferably selected from the group consisting of extended-spectrum beta-lactamase-producing (ESBL) Escherichia coli, ESBL Klebsiella pneumoniae, vancomycin-resistant Enterococcus (VRE), methicillin-resistant Staphylococcus aureus (MRSA), multidrug-resistant (MDR) Acinetobacter baumannii, MDR Enterobacter spp., and a combination thereof. Preferably, the targeted bacteria can be selected from the group consisting of extended-spectrum beta-lactamase-producing (ESBL) Escherichia coli strains.

Alternatively, the targeted bacterium can be a bacterium of the microbiome of a given species, preferably a bacterium of the human microbiota.

Bacterial Viruses

The bacterial virus particles are prepared from bacterial virus. The bacterial viruses are chosen in order to be able to introduce the payload into the targeted bacteria.

Bacterial viruses are preferably bacteriophages. Bacteriophage are obligate intracellular parasites that multiply inside bacteria by co-opting some or all of the host biosynthetic machinery. Phage genomes come in a variety of sizes and shapes (e.g., linear or circular). Most phages range in size from 24-200 nm in diameter. Phages contain nucleic acid (i.e., genome) and proteins, and may be enveloped by a lipid membrane. Depending upon the phage, the nucleic acid genome can be either DNA or RNA, and can exist in either circular or linear forms. The size of the phage genome varies depending upon the phage. The simplest phages have genomes that are only a few thousand nucleotides in size, while the more complex phages may contain more than 100,000 nucleotides in their genome, and in rare instances more than 1,000,000. The number and amount of individual types of protein in phage particles will vary depending upon the phage.

Optionally, the bacteriophage is selected from the Order Caudovirales consisting of, based on the taxonomy of Krupovic et al, Arch Virol, 2015:

family Myoviridae such as, without limitation, genus Cp220virus, Cp8virus, Ea214virus, Felixo1virus, Mooglevirus, Suspvirus, Hp1virus, P2virus, Kayvirus, P100virus, Silviavirus, Spo1virus, Tsarbombavirus, Twortvirus, Cc31virus, Jd18virus, Js98virus, Kp15virus, Moonvirus, Rb49virus, Rb69virus, S16virus, Schizot4virus, Sp18virus, T4virus, Cr3virus, Se1virus, V5virus, Abouovirus, Agatevirus, Agrican357virus, Ap22virus, Arv1virus, B4virus, Bastillevirus, Bc431virus, Bcep78virus, Bcepmuvirus, Biquartavirus, Bxz1virus, Cd119virus, Cp51virus, Cvm10virus, Eah2virus, Elvirus, Hapunavirus, Jimmervirus, Kpp10virus, M12virus, Machinavirus, Marthavirus, Msw3virus, Muvirus, Myohalovirus, Nit1virus, P1virus, Pakpunavirus, Pbunavirus, Phikzvirus, Rheph4virus, Rs12virus, Rs1unavirus, Secunda5virus, Sep1virus, Spn3virus, Svunavirus, Tg1virus, Vhm1virus and Wphvirus.

family Podoviridae such as, without limitation, genus Fri1virus, Kp32virus, Kp34virus, Phikmvvirus, Pradovirus, Sp6virus, T7virus, Cp1virus, P68virus, Phi29virus, Nona33virus, Pocjvirus, Tl2011virus, Bcep22virus, Bpp1virus, Cba41virus, Dfl12virus, Ea92virus, Epsilon15virus, F116virus, G7cvirus, Jwa1phavirus, Kf1virus, Kpp25virus, Lit1virus, Luz24virus, Luz7virus, N4virus, Nonanavirus, P22virus, Pagevirus, Phieco32virus, Prtbvirus, Sp58virus, Una961virus and Vp5virus.

family Siphoviridae such as, without limitation, genus Camvirus, Likavirus, R4virus, Acadianvirus, Coopervirus, Pgl1virus, Pipefishvirus, Rosebushvirus, Brujitavirus, Che9cvirus, Hawkeyevirus, Plotvirus, Jerseyvirus, Klgvirus, Sp311virus, Lmdlvirus, Una4virus, Bongovirus, Reyvirus, Buttersvirus, Charlievirus, Redivirus, Baxtervirus, Nymphadoravirus, Bignuzvirus, Fishburnevirus, Phayoncevirus, Kp36virus, Rogue1virus, Rtpvirus, T1virus, T1svirus, Ab18virus, Amigovirus, Anatolevirus, Andromedavirus, Attisvirus, Barnyardvirus, Berna113virus, Biseptimavirus, Bronvirus, C2virus, C5virus, Cba181virus, Cbastvirus, Cecivirus, Che8virus, Chivirus, Cjw1virus, Corndogvirus, Cronusvirus, D3112virus, D3virus, Decurrovirus, Demosthenesvirus, Doucettevirus, E125virus, Eiauvirus, Ff47virus, Gaiavirus, Gilesvirus, Gordonvirus, Gordtnkvirus, Harrisonvirus, Hk578virus, Hk97virus, Jenstvirus, Jwxvirus, Kelleziovirus, Korravirus, L5virus, Lambdavirus, Laroyevirus, Liefievirus, Marvinvirus, Mudcatvirus, N15virus, Nonagvirus, Nplvirus, Omegavirus, P12002virus, P12024virus, P23virus, P70virus, Pa6virus, Pamx74virus, Patiencevirus, Pbilvirus, Pepy6virus, Pfr1virus, Phic31virus, Phicbkvirus, Phietavirus, Phifelvirus, Phijllvirus, Pis4avirus, Psavirus, Psimunavirus, Rdjlvirus, Rer2virus, Sap6virus, Send513virus, Septima3virus, Seuratvirus, Sextaecvirus, Sfi11virus, Sfi21dtivirus, Sitaravirus, Sk1virus, Slashvirus, Smoothievirus, Soupsvirus, Spbetavirus, Ssp2virus, T5virus, Tankvirus, Tin2virus, Titanvirus, Tm4virus, Tp21virus, Tp84virus, Triavirus, Trigintaduovirus, Vegasvirus, Vendettavirus, Wbetavirus, Wildcatvirus, Wizardvirus, Woesvirus, Xp10virus, Ydn12virus and Yuavirus.

family Ackermannviridae such as, without limitation, genus Ag3virus, Limestonevirus, Cba120virus and Vilvirus.

Optionally, the bacteriophage is not part of the Order Caudovirales but from families with Unassigned order such as, without limitation, family Tectiviridae (such as genus Alphatectivirus, Betatectivirus), family Corticoviridae (such as genus Corticovirus), family Inoviridae (such as genus Fibrovirus, Habenivirus, Inovirus, Lineavirus, Plectrovirus, Saetivirus, Vespertiliovirus), family Cystoviridae (such as genus *Cystovirus*), family Leviviridae (such as genus Allolevivirus, Levivirus), family Microviridae (such as genus Alpha3microvirus, G4microvirus, Phix174microvirus, Bdellomicrovirus, Chlamydiamicrovirus, Spiromicrovirus) and family Plasmaviridae (such as genus *Plasmavirus*).

Optionally, the bacteriophage is targeting Archea not part of the Order Caudovirales but from families with Unassigned order such as, without limitation, Ampullaviridae, FuselloViridae, Globuloviridae, Guttaviridae, Lipothrixviridae, Pleolipoviridae, Rudiviridae, Salterprovirus and Bicaudaviridae.

A non-exhaustive listing of bacterial genera and their known host-specific bacteria viruses is presented in the following paragraphs. Synonyms and spelling variants are indicated in parentheses. Homonyms are repeated as often as they occur (e.g., D, D, d) Unnamed phages are indicated by "NN" beside their genus and their numbers are given in parentheses.

Bacteria of the genus *Actinomyces* can be infected by the following phages: Av-I, Av-2, Av-3, BF307, CT1, CT2, CT3, CT4, CT6, CT7, CT8 and 1281.

Bacteria of the genus *Aeromonas* can be infected by the following phages: AA-I, Aeh2, N, PM1, TP446, 3, 4, 11, 13, 29, 31, 32, 37, 43, 43-10T, 51, 54, 55R.1, 56, 56RR2, 57, 58, 59.1, 60, 63, Aeh1, F, PM2, 1, 25, 31, 40RR2.8t, (syn=44R), (syn=44RR2.8t), 65, PM3, PM4, PM5 and PM6.

Bacteria of the genus *Bacillus* can be infected by the following phages: A, aiz1, A1-K-I, B, BCJA1, BC1, BC2, BLL1, BL1, BP142, BSL1, BSL2, BS1, BS3, BS8, BS15, BS18, BS22, BS26, BS28, BS31, BS104, BS105, BS106, BTB, B1715V1, C, CK-I, Coll, Corl, CP-53, CS-I, CSi, D, D, D, D5, ent1, FPB, FP9, FSi, FS2, FS3, FS5, FS8, FS9, G, GH8, GT8, GV-I, GV-2, GT-4, g3, g12, g13, g14, g16, g17, g21, g23, g24, g29, H2, ken1, KK-88, Kum1, Kyu1, J7W-1, LP52, (syn=LP-52), L7, Mex1, MJ-I, mor2, MP-7, MP1O, MP12, MP14, MP15, Neo1, No 2, N5, N6P, PBC1, PBLA, PBP1, P2, S-a, SF2, SF6, Sha1, Si11, SP02, (syn=ΦSPP1), SPβ, STI, STi, SU-I1, t, TbI, Tb2, Tb5, TbIO, Tb26, Tb51, Tb53, Tb55, Tb77, Tb97, Tb99, Tb560, Tb595, Td8, Td6, Td15, TgI, Tg4, Tg6, Tg7, Tg9, TgIO, TgI1, Tg13, Tg15, Tg21, Tin1, Tin7, Ting, Tin13, Tm3, Toc1, Tog1, to11, TP-I, TP-10vir, TP-15c, TP-16c, TP-17c, TP-19, TP35, TP51, TP-84, Tt4, Tt6, type A, type B, type C, type D, type E, Tφ3, VA-9, W, wx23, wx26, Yun1, α, γ, p11, φmed-2, φT, φμ-4, φ3T, φ75, φ1O5, (syn=φ1O5), IA, IB, 1-97A, 1-97B, 2, 2, 3, 3, 3, 5, 12, 14, 20, 30, 35, 36, 37, 38, 41C, 51, 63, 64, 138D, I, II, IV, NN-*Bacillus* (13), ale1, AR1, AR2, AR3, AR7, AR9, Bace-11, (syn=11), Bastille, BL1, BL2, BL3, BL4, BL5, BL6, BL8, BL9, BP124, BS28, BS80, Ch, CP-51, CP-54, D-5, dar1, den1, DP-7, ent1, FoSi, FoS2, FS4, FS6, FS7, G, ga11, gamma, GE1, GF-2, GSi, GT-I, GT-2, GT-3, GT-4, GT-5, GT-6, GT-7, GV-6, g15, 19, 110, ISi, K, MP9, MP13, MP21, MP23, MP24, MP28, MP29, MP30, MP32, MP34, MP36, MP37, MP39, MP40, MP41, MP43, MP44, MP45, MP47, MP50, NLP-I, No. 1, N17, N19, PBS1, PK1, PMB1, PMB12, PMJ1, S, SPO1, SP3, SP5, SP6, SP7, SP8, SP9, SP1O, SP-15, SP50, (syn=SP-50), SP82, SST, sub1, SW, Tg8, Tg12, Tg13, Tg14, thu1, thuA, thuS, Tin4, Tin23, TP-13, TP33, TP50, TSP-I, type V, type VI, V, Vx, β22, φe, φNR2, φ25, φ63, 1, 1, 2, 2C, 3NT, 4, 5, 6, 7, 8, 9, 10, 12, 12, 17, 18, 19, 21, 138, III, 4 (*B. megateriwn*), 4 (*B. sphaericus*), AR13, BPP-IO, BS32, BS107, B1, B2, GA-I, GP-IO, GV-3, GV-5, g8, MP20, MP27, MP49, Nf, PP5, PP6, SF5, Tg18, TP-I, Versailles, φ15, φ29, 1-97, 837/IV, mt-*Bacillus* (1), Bat1O, BSL1O, BSLI 1, BS6, BSI 1, BS16, BS23, BS1O1, BS102, g18, mor1, PBL1, SN45, thu2, thu3, TmI, Tm2, TP-20, TP21, TP52, type F, type G, type IV, HN-BacMus (3), BLE, (syn=θc), BS2, BS4, BSS, BS7, B1O, B12, BS20, BS21, F, MJ-4, PBA12, AP50, AP50-04, AP50-11, AP50-23, AP50-26, AP50-27 and Bam35. The following *Bacillus*-specific phages are defective: DLP10716, DLP-11946, DPB5, DPB12, DPB21, DPB22, DPB23, GA-2, M, No. IM, PBLB, PBSH, PBSV, PBSW, PBSX, PBSY, PBSZ, phi, SPa, type 1 and μ.

Bacteria of the genus *Bacteroides* can be infected by the following phages: ad I2, Baf-44, Baf-48B, Baf-64, Bf-I, Bf-52, B40-8, F1, β1, φA1, φBrO1, φBrO2, 11, 67.1, 67.3, 68.1, mt-*Bacteroides* (3), Bf42, Bf71, HN-Bdellovibrio (1) and BF-41.

Bacteria of the genus *Bordetella* can be infected by the following phages: 134 and NN-*Bordetella* (3).

Bacteria of the genus *Borrellia* can be infected by the following phages: NN-*Borrelia* (1) and NN-*Borrelia* (2).

Bacteria of the genus *Brucella* can be infected by the following phages: A422, Bk, (syn=Berkeley), BM29, FOi, (syn=F01), (syn=FQ1), D, FP2, (syn=FP2), (syn=FD2), Fz, (syn=Fz75/13), (syn=Firenze 75/13), (syn=Fi), Fi, (syn=F1), Fim, (syn=Flm), (syn=Fim), FiU, (syn=HU), (syn=FiU), F2, (syn=F2), F3, (syn=F3), F4, (syn=F4), F5, (syn=F5), F6, F7, (syn=F7), F25, (syn=F25), (syn=£25), F25U, (syn=F25u), (syn=F25U), (syn=F25V), F44, (syn-F44), F45, (syn=F45), F48, (syn=F48), I, Im, M, MC/75, M51, (syn=M85), P, (syn=D), 5708, R, Tb, (syn=TB), (syn=Tbilisi), W, (syn=Wb), (syn=Weybridge), X, 3, 6, 7, 10/1, (syn=10), (syn=F8), (syn=F8), 12m, 24/11, (syn=24), (syn=F9), (syn=F9), 45/111, (syn=45), 75, 84, 212/XV, (syn=212), (syn=Fi0), (syn=F10), 371/XXIX, (syn=371), (syn=Fn), (syn=F11) and 513.

Bacteria of the genus *Burkholderia* can be infected by the following phages: CP75, NN-*Burkholderia* (1) and 42.

Bacteria of the genus *Campylobacter* can be infected by the following phages: C type, NTCC12669, NTCC12670, NTCC12671, NTCC12672, NTCC12673, NTCC12674, NTCC12675, NTCC12676, NTCC12677, NTCC12678, NTCC12679, NTCC12680, NTCC12681, NTCC12682, NTCC12683, NTCC12684, 32f, 111c, 191, NN-*Campylobacter* (2), Vfi-6, (syn=V19), VfV-3, V2, V3, V8, V16, (syn=Vfi-1), V19, V20(V45), V45, (syn=V-45) and NN-*Campylobacter* (1).

Bacteria of the genus *Chlamydia* can be infected by the following phage: Chp1.

Bacteria of the genus *Clostridium* can be infected by the following phages: CAK1, CA5, Ca7, CEβ, (syn=1C), CEγ, Cld1, c-n71, c-203 Tox-, DEβ, (syn=ID), (syn=1Dt0X+), HM3, KM1, KT, Ms, NA1, (syn=Naltox+), PA135Oe, Pfó, PL73, PL78, PL81, P1, P50, P5771, P19402, 1CtOX+, 2CtOX\2D3 (syn=2Dt0X+), 3C, (syn=3Ctox+), 4C, (syn=4CtOX+), 56, III-1, NN-*Clostridium* (61), NB1t0X+, α1, CA1, HMT, HM2, PF15 P-23, P-46, Q-05, Q-oe, Q-16, Q-21, Q-26, Q-40, Q-46, S111, SA02, WA01, WA03, Wm, W523, 80, C, CA2, CA3, CPT1, CPT4, c1, c4, c5, HM7, H11/A1, H18/Ax, FWS23, Hi58ZA1, K2ZA1, K21ZS23, ML, NA2tOX; Pf2, Pf3, Pf4, S9ZS3, S41ZA1, S44ZS23, α2, 41, 112ZS23, 214/S23, 233/Ai, 234/S23, 235/S23, II-1, 11-2, 11-3, NN-*Clostridium* (12), CA1, F1, K, S2, 1, 5 and NN-*Clostridium* (8).

Bacteria of the genus *Corynebacterium* can be infected by the following phages: CGK1 (defective), A, A2, A3, A101, A128, A133, A137, A139, A155, A182, B, BF, B17, B18, B51, B271, B275, B276, B277, B279, B282, C, capi, CC1, CG1, CG2, CG33, CL31, Cog, (syn=CG5), D, E, F, H, H-I, hqi, hq2, 11ZH33, Ii/31, J, K, K, (syn=Ktox"), L, L, (syn=Ltox+), M, MC-I, MC-2, MC-3, MC-4, MLMa, N, O, ovi, ov2, ov3, P, P, R, RP6, RS29, S, T, U, UB1, ub2, UH1, UH3, uh3, uh5, uh6, β, (syn=βtox+), βhv64, βvir, γ, (syn=γtoχ-), γ19, δ, (syn=δ'ox+), p, (syn=ptoχ-), Φ9, φ84, ω, IA, 1/1180, 2, 2/1180, 5/1180, 5ad/9717, 7/4465, 8/4465, 8ad/10269, 10/9253, 13Z9253, 15/3148, 21/9253, 28, 29, 55, 2747, 2893, 4498 and 5848.

Bacteria of the genus *Enterococcus* are infected by the following phage: DF78, F1, F2, 1, 2, 4, 14, 41, 867, D1, SB24, 2BV, 182, 225, C2, C2F, E3, E62, DS96, H24, M35, P3, P9, SB1O1, S2, 2B II, 5, 182a, 705, 873, 881, 940, 1051, 1057, 21096C, NN-*Enterococcus* (1), PE1, F1, F3, F4, VD13, 1, 200, 235 and 341.

Bacteria of the genus *Erysipelothrix* can be infected by the following phage: NN-*Eiysipelothrix* (1).

Bacteria of the genus *Escherichia* can be infected by the following phages: BW73, B278, D6, D108, E, E1, E24, E41, FI-2, FI-4, FI-5, HI8A, Ff18B, i, MM, Mu, (syn=mu), (syn=MuI), (syn=Mu-I), (syn=MU-I), (syn=MuI), (syn=μ), 025, PhI-5, Pk, PSP3, P1, P1D, P2, P4 (defective), S1, Wφ, φK13, φR73 (defective), φ1, φ2 , φ7, φ92, iv (defective), 7 A, 8φ, 9φ, 15 (defective), 18, 28-1, 186, 299, HH-*Escherichia* (2), AB48, CM, C4, C16, DD-VI, (syn=Dd-Vi), (syn=DDVI), (syn=DDVi), E4, E7, E28, FI1, FI3, H, H1, H3, H8, K3, M, N, ND-2, ND-3, ND4, ND-5, ND6, ND-7, Ox-I (syn=OX1), (syn=HF), Ox-2 (syn=0x2), (syn=0X2), Ox-3, Ox-4, Ox-5, (syn=0X5), Ox-6, (syn=66F), (syn=φ66t), (syn=φ66t-)5 0111, PhI-I, RB42, RB43, RB49, RB69, S, SaI-I, Sa1-2, Sa1-3, Sa1-4, Sa1-5, Sa1-6, TC23, TC45, TuII*-6, (syn=TuII*), TuIP-24, TuII*46, TuIP-60, T2, (syn=ganuTia), (syn=γ), (syn=PC), (syn=P.C.), (syn=T-2), (syn=T2), (syn=P4), T4, (syn=T-4), (syn=T4), T6, T35, α1, 1, IA, 3, (syn=Ac3), 3A, 3T+, (syn=3), (syn=M1), 5φ, (syn=φ5), 9266Q, CFO103, HK620, J, K, K1F, m59, no. A, no. E, no. 3, no. 9, N4, sd, (syn=Sd), (syn=SD), (syn=Sa)3 (syn=sd), (syn=SD), (syn=CD), T3, (syn=T-3), (syn=T3), T7, (syn=T-7), (syn=T7), WPK, W31, ΔH, φC3888, φK3, φK7, φK12, φV-1, Φ04-CF, Φ05, Φ06, Φ07, φ1, φ1.2, φ20, φ95, φ263, φ1O92, φ1, φ11, (syn=φW), Ω8, 1, 3, 7, 8, 26, 27, 28-2, 29, 30, 31, 32, 38, 39, 42, 933W, NN-*Escherichia* (1), Esc-7-11, AC30, CVX-5, C1, DDUP, EC1, EC2, E21, E29, F1, F26S, F27S, Hi, HK022, HK97, (syn=ΦHK97), HK139, HK253, HK256, K7, ND-I, no.D, PA-2, q, S2, T1, (syn=α), (syn=P28), (syn=T-I), (syn=Tx), T3C, T5, (syn=T-5), (syn=T5), UC-I, w, β4, γ2, λ (syn=lambda), (syn=Φλ), ΦD326, φγ, Φ06, Φ7, Φ10, λ80, χ, (syn=χi), (syn=φχ), (syn=φχi), 2, 4, 4A, 6, 8A, 102, 150, 168, 174, 3000, AC6, AC7, AC28, AC43, AC50, AC57, AC81, AC95, HK243, K1O, ZG/3A, 5, 5A, 21EL, H19-J and 933H.

Bacteria of the genus *Fusobacterium* are infected by the following phage: NN-*Fusobacterium* (2), fv83-554/3, fv88-531/2, 227, fv2377, fv2527 and fv8501.

Bacteria of the genus *Haemophilus* are infected by the following phage: HP1, S2 and N3.

Bacteria of the genus *Helicobacter* are infected by the following phage: HP1 and ^^-*Helicobacter* (1).

Bacteria of the genus *Klebsiella* are infected by the following phage: AIO-2, KI4B, K16B, K19, (syn=K19), K114, K115, K121, K128, K129, KI32, K133, K135, K1106B, K1171B, K1181B, K1832B, AIO-I, AO-I, AO-2, AO-3, FC3-10, K, K11, (syn=KI1), K12, (syn=K12), K13, (syn=K13), K1 70/11), K14, (syn=K14), K15, (syn=K15), K16, (syn=K16), K17, (syn=K17), K18, (syn=K18), K119, (syn=K19), K127, (syn=K127), K131, (syn=K131), K135, K1171B, II, VI, IX, CI-I, K14B, K18, K111, K112, K113, K116, K117, K118, K120, K122, K123, K124, K126, K130, K134, K1106B, KIi65B, K1328B, KLXI, K328, P5046, 11, 380, III, IV, VII, VIII, FC3-11, K12B, (syn=K12B), K125, (syn=K125), K142B, (syn=K142), (syn=K142B), K1181B, (syn=KI1 81), (syn=K1181B), K1765/!, (syn=K1765/1), K1842B, (syn=K1832B), K1937B, (syn=K1937B), L1, φ28, 7, 231, 483, 490, 632 and 864/100.

Bacteria of the genus *Lepitospira* are infected by the following phage: LE1, LE3, LE4 and ~NN-*Leptospira* (1).

Bacteria of the genus *Listeria* are infected by the following phage: A511, 01761, 4211, 4286, (syn=B054), A005, A006, A020, A500, A502, A511, A1 18, A620, A640, B012, B021, B024, B025, B035, B051, B053, B054, B055, B056, B101, BI 10, B545, B604, B653, C707, D441, H5047, H1OG, H8/73, H19, H21, H43, H46, H107, H108, HI 10, H163/84, H312, H340, H387, H391/73, H684/74, H924A, PSA, U153, φMLUP5, (syn=P35), 00241, 00611, 02971A, 02971C, 5/476, 5/911, 5/939, 5/11302, 5/11605, 5/11704, 184, 575, 633, 699/694, 744, 900, 1090, 1317, 1444, 1652, 1806, 1807, 1921/959, 1921/11367, 1921/11500, 1921/ 11566, 1921/12460, 1921/12582, 1967, 2389, 2425, 2671, 2685, 3274, 3550, 3551, 3552, 4276, 4277, 4292, 4477, 5337, 5348/11363, 5348/11646, 5348/12430, 5348/12434, 10072, 11355C, 11711A, 12029, 12981, 13441, 90666, 90816, 93253, 907515, 910716 and NN-Lisferia (15).

Bacteria of the genus *Morganella* are infected by the following phage: 47.

Bacteria of the genus *Mycobacterium* are infected by the following phage: 13, AG1, ALi, ATCC 11759, A2, B.C3, BG2, BK1, BK5, *butyricum*, B-I, B5, B7, B30, B35, Clark, C1, C2, DNAIII, DSP1, D4, D29, GS4E, (syn=GS4E), GS7, (syn=GS-7), (syn=GS7), lacticola, Legendre, Leo, L5, (syn=ΦL-5), MC-I, MC-3, MC-4, minetti, MTPHI 1, Mx4, MyF3P/59a, phlei, (syn=phlei 1), phlei 4, Polonus II, rabinovitschi, smegmatis, TM4, TM9, TM1O, TM20, Y7, Y1O, φ630, IB, IF, IH, 1/1, 67, 106, 1430, B1, (syn=Bo1), B24, D, D29, F-K, F-S, HP, Polonus I, Roy, R1, (syn=R1-Myb), (syn=Ri), 11, 31, 40, 50, 103a, 103b, 128, 3111-D, 3215-D and NN-*Mycobacterium* (1).

Bacteria of the genus *Neisseria* are infected by the following phage: Group I, group II and NP1.

Bacteria of the genus *Nocardia* are infected by the following phage: MNP8, NJ-L, NS-8, N5 and TtiN-*Nocardia*.

Bacteria of the genus *Proteus* are infected by the following phage: Pm5, 13vir, 2/44, 4/545, 6/1004, 13/807, 20/826, 57, 67b, 78, 107/69, 121, 9/0, 22/608, 30/680, PmI, Pm3, Pm4, Pm6, Pm7, Pm9, PmIO, PmI1, Pv2, π1, φm, 7/549, 9B/2, 10A/31, 12/55, 14, 15, 16/789, 17/971, 19A/653, 23/532, 25/909, 26/219, 27/953, 32A/909, 33/971, 34/13, 65, 5006M, 7480b, VI, 13/3a, Clichy 12, π2600, φχ7, 1/1004, 5/742, 9, 12, 14, 22, 24/860, 2600/D52, Pm8 and 24/2514.

Bacteria of the genus *Providencia* are infected by the following phage: PL25, PL26, PL37, 9211/9295, 9213/921 Ib, 9248, 7/R49, 7476/322, 7478/325, 7479, 7480, 9000/ 9402 and 9213/921 Ia.

Bacteria of the genus *Pseudomonas* are infected by the following phage: PfI, (syn=Pf-I), Pf2, Pf3, PP7, PRR1, 7s, im-*Pseudomonas* (1), AI-I, AI-2, B 17, B89, CB3, Co1 2, Co1 11, Co1 18, Co1 21, C154, C163, C167, C2121, E79, F8, ga, gb, H22, K1, M4, N2, Nu, PB-I, (syn=PB1), pf16, PMN17, PP1, PP8, Psa1, PsP1, PsP2, PsP3, PsP4, PsP5, PS3, PS17, PTB80, PX4, PX7, PYO1, PYO2, PYO5, PYO6, PYO9, PYO1O, PYO13, PYO14, PYO16, PYO18, PYO19, PYO20, PYO29, PYO32, PYO33, PYO35, PYO36, PYO37, PYO38, PYO39, PYO41, PYO42, PYO45, PYO47, PYO48, PYO64, PYO69, PYO103, P1K, SLP1, SL2, S2, UNL-I, wy, Yai, Ya4, Yan, φBE, φCTX, φC17, φKZ, (syn=ΦKZ), φ-LT, Φmu78, φNZ, φPLS-1, φST-1, φW-14, φ-2, 1/72, 2/79, 3, 3/DO, 4/237, 5/406, 6C, 6/6660, 7, 7v, 7/184, 8/280, 9/95, 10/502, 11/DE, 12/100, 12S, 16, 21, 24, 25F, 27, 31, 44, 68, 71, 95, 109, 188, 337, 352, 1214, HN-*Pseudomonas* (23), A856, B26, CI-I, CI-2, C5, D, gh-1, F1 16, HF, H90, K5, K6, K104, K109, K166, K267, N4, N5, 06N-25P, PE69, Pf, PPN25, PPN35, PPN89, PPN91, PP2, PP3, PP4, PP6, PP7, PP8, PP56, PP87, PP1 14, PP206, PP207, PP306, PP651, Psp231a, Pssy401, Pssy9220, psi, PTB2, PTB20, PTB42, PX1, PX3, PX1O, PX12, PX14, PYO70, PYO71, R, SH6, SH133, tf, Ya5, Ya7, φBS, ΦKf77, φ-MC, ΦmnF82, φPLS27, φPLS743, φS-1, 1, 2, 2, 3, 4, 5, 6, 7, 7, 8, 9, 10, 11, 12, 12B, 13, 14, 15, 14, 15, 16, 17, 18, 19, 20, 20, 21, 21, 22, 23, 23, 24, 25, 31, 53, 73, 119x, 145, 147, 170, 267, 284, 308, 525, NN-*Pseudomonas* (5), af, A7, B3, B33, B39, BI-I, C22, D3, D37, D40, D62, D3112, F7, F1O, g, gd, ge, gξ Hw12, Jb 19, KF1, L°, OXN-32P, O6N-52P, PCH-I, PC13-1, PC35-1, PH2, PH51, PH93, PH132, PMW, PM13, PM57, PM61, PM62, PM63, PM69, PM105, PM1 13, PM681, PM682, PO4, PP1, PP4, PP5, PP64, PP65, PP66, PP71, PP86, PP88, PP92, PP401, PP711, PP891, Pssy41, Pssy42, Pssy403, Pssy404, Pssy420, Pssy923, PS4, PS-IO, Pz, SD1, SL1, SL3, SL5, SM, φC5, φC11, φC11-1, φC13, φC15, φMO, φX, φO4, φ1 1, φ240, 2, 2F, 5, 7m, 11, 13, 13/441, 14, 20, 24, 40, 45, 49, 61, 73, 148, 160, 198, 218, 222, 236, 242, 246, 249, 258, 269, 295, 297, 309, 318, 342, 350, 351, 357-1, 400-1, HN-*Pseudomonas* (6), G1O1, M6, M6a, L1, PB2, Pssy15, Pssy4210, Pssy4220, PYO12, PYO34, PYO49, PYO50, PYO51, PYO52, PYO53, PYO57, PYO59, PYO200, PX2, PX5, SL4, φO3, φO6 and 1214.

Bacteria of the genus *Rickettsia* are infected by the following phage: NN-*Rickettsia*.

Bacteria of the genus *Salmonella* are infected by the following phage: b, Beccles, CT, d, Dundee, f, FeIs 2, GI, GUI, GVI, GVIII, k, K, i, j, L, 01, (syn=0-1), (syn=O1), (syn=O-I), (syn=7), 02, 03, P3, P9a, P1O, Sab3, Sab5, San1S, San17, SI, Taunton, ViI, (syn=ViI), 9, imSalmonella (1), N-I, N-5, N-IO, N-17, N-22, 11, 12, 16-19, 20.2, 36, 449C/C178, 966A/C259, a, B.A.O.R., e, G4, GUI, L, LP7, M, MG40, N-18, PSA68, P4, P9c, P22, (syn=P22), (syn=PLT22), (syn=PLT22), P22a1, P22-4, P22-7, P22-11, SNT-I, SNT-2, SP6, Vi11i ViIV, ViV, ViVI, ViVII, Worksop, Sj5, ε34, 1, 37, 1(40), (syn=φ1[40]), 1, 422, 2, 2.5, 3b, 4, 5, 6, 14(18), 8, 14(6,7), 10, 27, 28B, 30, 31, 32, 33, 34, 36, 37, 39, 1412, SNT-3, 7-11, 40.3, c, C236, C557, C625, C966N, g, GV, G5, G1 73, h, IRA, Jersey, MB78, P22-1, P22-3, P22-12, Sab1, Sab2, Sab2, Sab4, San1, San2, San3, San4, San6, San7, San8, San9, San13, San14, San16, San18, San19, San20, San21, San22, San23, San24, San25, San26, SasL1, SasL2, SasL3, SasL4, SasL5, S1BL, SII, ViII, φ1, 1, 2, 3a, 3a1, 1010, Ym-*Salmonella* (1), N-4, SasL6 and 27.

Bacteria of the genus *Serratia* are infected by the following phage: A2P, PS20, SMB3, SMP, SMP5, SM2, V40, V56, ic, ΦCP-3, ΦCP-6, 3M, 10/1a, 20A, 34CC, 34H, 38T, 345G, 345P, 501B, SMB2, SMP2, BC, BT, CW2, CW3, CW4, CW5, Lt232, L2232, L34, L.228, SLP, SMPA, V.43, σ, φCW1, ΦCP-6-1, ΦCP-6-2, ΦCP-6-5, 3T, 5, 8, 9F, 10/1, 2OE, 32/6, 34B, 34CT, 34P, 37, 41, 56, 56D, 56P, 6OP, 61/6, 74/6, 76/4, 101/8900, 226, 227, 228, 229F, 286, 289, 290F, 512, 764a, 2847/10, 2847/1Oa, L.359 and SMB1.

Bacteria of the genus *Shigella* are infected by the following phage: Fsa, (syn=a), FSD2d, (syn=D2d), (syn=W2d), FSD2E, (syn=W2e), fv, F6, f7.8, H-Sh, PE5, P90, SfII, Sh, SHm, SHrv, (syn=HIV), SHvi, (syn=HVI), SHVvm, (syn=HVIII), SKγ66, (syn=gamma 66), (syn=γββ), (syn=γ66b), SKm, (syn=SIIIb)5 (syn=UI), SKw, (syn=Siva), (syn=IV), SIC™, (syn=SIVA.), (syn=IVA), SKvi, (syn=KVI), (syn=Svi), (syn=VI), SKvm, (syn=Svm), (syn=VIII), SKVIIIA, (syn=SvmA), (syn=VIIIA), STvi, STK, STx1, STxn, S66, W2, (syn=D2c), (syn=D20), φ1, φIVb 3-SO-R, 8368-SO-R, F7, (syn=FS7), (syn=K29), F1O, (syn=FS1O), (syn=K31), I1, (syn=alfa), (syn=FSa), (syn=K18), (syn=α), I2, (syn=a), (syn=K19), SG33, (syn=G35), (syn=SO-35/G), SG35, (syn=SO-55/G), SG3201, (syn=SO-3201/G), SHn, (syn=HII), SHv, (syn=SHV), SHx, SHX, SKn, (syn=K2), (syn=KII), (syn=Sn), (syn=SsII), (syn=II), SKrv, (syn=Sm), (syn=SsIV), (syn=IV), SK1Va, (syn=Swab), (syn=SsIVa), (syn=IVa), SKV, (syn=K4), (syn=KV), (syn=SV), (syn=SsV), (syn=V), SKx, (syn=K9), (syn=KX), (syn=SX), (syn=SsX), (syn=X), STV, (syn=T35), (syn=35-50-R), STvm, (syn=T8345), (syn=8345-SO-S-R), W1, (syn=D8), (syn=FSD8), W2a, (syn=D2A), (syn=FS2a), DD-2, Sf6, FSi, (syn=F1), SF6, (syn=F6), SG42, (syn=SO-42/G), SG3203, (syn=SO-3203/G), SKF12, (syn=SsF12), (syn=F12), (syn=F12), STn, (syn=1881-SO-R), γ66, (syn=gamma 66a), (syn=Ssγ66), φ2, BI1, DDVII, (syn=DD7), FSD2b, (syn=W2B), FS2, (syn=F2), (syn=F2), FS4, (syn=F4), (syn=F4), FS5, (syn=F5), (syn=F5), FS9, (syn=F9), (syn=F9), FI 1, P2-S0-S, SG36, (syn=SO-36/G), (syn=G36), SG3204, (syn=SO-3204/G), SG3244, (syn=SO-3244/G), SHi, (syn=HI), SHvπ, (syn=HVII), SHK, (syn=HIX), SHx1, SHxπ, (syn=HXn), SKI, KI, (syn=S1), (syn=SsI), SKVII, (syn=KVII), (syn=Svπ), (syn=SsVII), SKIX, (syn=KIX), (syn=S1x), (syn=SsIX), SKXII, (syn=KXII), (syn=Sxn), (syn=SsXII), STi, STff1, STrv, STVi, STvπ, S70, 5206, U2-S0-S, 3210-SO-S, 3859-SO-S, 4020-SO-S, φ3, φ5, φ7, φ8, φ9, φ10, φ11, φ13, φ14, φ18, SHm, (syn=Hπi), SHχi, (syn=HXt) and SKxI, (syn=KXI), (syn=Sχi), (syn=SsXI), (syn=XI).

Bacteria of the genus *Staphylococcus* are infected by the following phage: A, EW, K, Ph5, Ph9, PhIO, Ph13, P1, P2, P3, P4, P8, P9, P1O, RG, SB-i, (syn=Sb-I), S3K, Twort, ΦSK311, φ812, 06, 40, 58, 119, 130, 131, 200, 1623, STC1, (syn=stc1), STC2, (syn=stc2), 44AHJD, 68, AC1, AC2, A6"C", A9"C", b581, CA-I, CA-2, CA-3, CA-4, CA-5, DI 1, L39x35, L54a, M42, N1, N2, N3, N4, N5, N7, N8, N1O, Ni 1, N12, N13, N14, N16, Ph6, Ph12, Ph14, UC-18, U4, U15, S1, S2, S3, S4, S5, X2, Z1, φB5-2, φD, ω, 11, (syn=φ11), (syn=P11-M15), 15, 28, 28A, 29, 31, 31B, 37, 42D, (syn=P42D), 44A, 48, 51, 52, 52A, (syn=P52A), 52B, 53, 55, 69, 71, (syn=P71), 71A, 72, 75, 76, 77, 79, 80, 80α, 82, 82A, 83 A, 84, 85, 86, 88, 88A, 89, 90, 92, 95, 96, 102, 107, 108, 111, 129-26, 130, 130A, 155, 157, 157A, 165, 187, 275, 275A, 275B, 356, 456, 459, 471, 471A, 489, 581, 676, 898, 1139, 1154A, 1259, 1314, 1380, 1405, 1563, 2148, 2638A, 2638B, 2638C, 2731, 2792A, 2792B, 2818, 2835, 2848A, 3619, 5841, 12100, AC3, A8, A1O, A13, b594n, D, HK2, N9, N15, P52, P87, S1, S6, Z4, φRE, 3A, 3B, 3C, 6, 7, 16, 21, 42B, 42C, 42E, 44, 47, 47A5 47C, 51, 54, 54x1, 70, 73, 75, 78, 81, 82, 88, 93, 94, 101, 105, 110, 115, 129/16, 174, 594n, 1363/14, 2460 and mS-*Staphylococcus* (1).

Bacteria of the genus *Streptococcus* are infected by the following phage: EJ-I, NN-*Streptococais* (1), a, C1, FL0Ths, H39, Cp-I, Cρ-5, Cp-7, Cp-9, Cp-IO, AT298, A5, a1O/J1, a1O/J2, a1O/J5, a1O/J9, A25, BTI 1, b6, CA1, c20-1, c20-2, DP-I, Dp-4, DT1, ET42, e1O, FA101, FETths, Fκ, FKKIOI, FKLIO, FKP74, FKH, FLOThs, FyIO1, f1, F10, F20140/76, g, GT-234, HB3, (syn=HB-3), HB-623, HB-746, M102, O1205, φO1205, PST, PO, P1, P2, P3, P5, P6, P8, P9, P9, P12, P13, P14, P49, P50, P51, P52, P53, P54, P55, P56, P57, P58, P59, P64, P67, P69, P71, P73, P75, P76, P77, P82, P83, P88, sc, sch, sf, Sfi1 1, (syn=SFiI 1), (syn=φSFi11), (syn=ΦSfi1 1), (syn=φSfi1 1), sfi19, (syn=SFi19), (syn=φSFi19), (syn=φSfi19), Sfi21, (syn=SFi21), (syn=φSFi21), (syn=φSfi21), ST0, STX, st2, ST2, ST4, S3, (syn=φS3), s265, Φ17, φ42, Φ57, φ80, φ81, φ82, φ83, φ84, φ85, φ86, φ87, φ88, φ89, φ90, φ91, φ92, φ93, φ94, φ95, φ96, φ97, φ98, φ99, φ100, φ101, φ102, φ227, Φ7201, ω1, ω2, ω3, ω4, ω5, ω6, ω8, ω1O, 1, 6, 9, 1OF, 12/12, 14, 17SR, 19S, 24, 50/33, 50/34, 55/14, 55/15, 70/35, 70/36, 71/ST15, 71/45, 71/46, 74F, 79/37, 79/38, 80/J4, 80/J9, 80/5T16, 80/15, 80/47, 80/48, 101, 103/39, 103/40, 121/41, 121/42, 123/43, 123/44, 124/44, 337/ST17 and m*Streptococcus* (34).

Bacteria of the genus *Treponema* are infected by the following phage: NN-*Treponema* (1).

Bacteria of the genus *Vibrio* are infected by the following phage: CTXΦ, fs, (syn=si), fs2, Ivpf5, Vf12, Vf33, VPIΦ, VSK, v6, 493, CP-T1, ET25, kappa, K139, Labol,)XN-69P, OXN-86, O6N-21P, PB-I, P147, rp-1, SE3, VA-I, (syn=VcA-I), VcA-2, VP1, VP2, VP4, VP7, VP8, VP9, VP1O, VP17, VP18, VP19, X29, (syn=29 d'Herelle), t, ΦHAWI-1, ΦHAWI-2, ΦHAWI-3, ΦHAWI-4, ΦHAWI-5, ΦHAWI-6, ΦHAWI-7, XHAWI-8, ΦHAWI-9, ΦHAWI-10, ΦHCl-1, ΦHC1-2, ΦHC1-3, ΦHC1-4, ΦHC2-1, >HC2-2, ΦHC2-3, ΦHC2-4, ΦHC3-1, ΦHC3-2, ΦHC3-3, ΦHD1S-1, ΦHD1S-2, ΦHD2S-1, ΦHD2S-2, ΦHD2S-3, ΦHD2S-4, ΦHD2S-5, ΦHDO-1, ΦHDO-2, ΦHDO-3, ΦHDO-4, ΦHDO-5, ΦHDO-6, ΦKL-33, ΦKL-34, ΦKL-35, ΦKL-36, ΦKWH-2, ΦKWH-3, ΦKWH-4, ΦMARQ-1, ΦMARQ-2, ΦMARQ-3, ΦMOAT-1, ΦO139, ΦPEL1A-1, ΦPEL1A-2, ΦPEL8A-1, ΦPEL8A-2, ΦPEL8A-3, ΦPEL8C-1, ΦPEL8C-2, ΦPEL13A-1, ΦPEL13B-1, ΦPEL13B-2, ΦPEL13B-3, ΦPEL13B-4, ΦPEL13B-5, ΦPEL13B-6, ΦPEL13B-7, ΦPEL13B-8, ΦPEL13B-9, ΦPEL13B-10, φVP143, φVP253, Φ16, φ138, 1-II, 5, 13, 14, 16, 24, 32, 493, 6214, 7050, 7227, II, (syn=group II), (syn==φ2), V, VIII, ~m-*Vibrio* (13), KVP20, KVP40, nt-1, O6N-22P, P68, e1, e2, e3, e4, e5, FK, G, I, K, nt-6, N1, N2, N3, N4, N5, O6N-34P, OXN-72P, OXN-85P, OXN-100P, P, Ph-I, PL163/10, Q, S, T, φ92, 1-9, 37, 51, 57, 70A-8, 72A-4, 72A-10, 110A-4, 333, 4996, I (syn=group I), III (syn=group III), VI, (syn=A-Saratov), VII, IX, X, HN-*Vibrio* (6), pA1, 7, 7-8, 70A-2, 71A-6, 72A-5, 72A-8, 108A-10, 109A-6, 109A-8, 1 1OA-1, 110A-5, 110A-7, hv-1, OXN-52P, P13, P38, P53, P65, P108, Pi11, TPI3 VP3, VP6, VP12, VP13, 70A-3, 70A-4, 70A-10, 72A-1, 108A-3, 109-B1, 110A-2, 149, (syn=φ149), IV, (syn=group IV), NN-*Vibrio* (22), VP5, VPI1, VP15, VP16, α1, α2, α3a, α3b, 353B and HN-*Vibrio* (7).

Bacteria of the genus *Yersinia* are infected by the following phage: H, H-I, H-2, H-3, H-4, Lucas 110, Lucas 303, Lucas 404, YerA3, YerA7, YerA20, YerA41, 3/M64-76, 5/G394-76, 6/C753-76, 8/C239-76, 9/F18167, 1701, 1710, PST, 1/F2852-76, D'Herelle, EV, H, Kotljarova, PTB, R, Y, YerA41, φNerO3-12, 3, 4/C1324-76, 7/F783-76, 903, 1/M6176 and Yer2AT.

More preferably, the bacteriophage is selected in the group consisting of *Salmonella* virus SKML39, *Shigella* virus AG3, Dickeya virus Limestone, Dickeya virus RC2014, *Escherichia* virus CBA120, *Escherichia* virus PhaxI, *Salmonella* virus 38, *Salmonella* virus Det7, *Salmonella* virus GG32, *Salmonella* virus PM10, *Salmonella* virus SFP10, *Salmonella* virus SH19, *Salmonella* virus SJ3, *Escherichia* virus ECML4, *Salmonella* virus Marshall, *Salmonella* virus Maynard, *Salmonella* virus SJ2, *Salmonella* virus STML131, *Salmonella* virus Vil, *Erwinia* virus Ea2809, *Klebsiella* virus 0507KN21, *Serratia* virus IME250, *Serratia* virus MAM1, *Campylobacter* virus CP21, *Campylobacter* virus CP220, *Campylobacter* virus CPt10, *Campylobacter* virus IBB35, *Campylobacter* virus CP81, *Campylobacter* virus CP30A, *Campylobacter* virus CPX, *Campylobacter* virus NCTC12673, *Erwinia* virus Ea214, *Erwinia* virus M7, *Escherichia* virus AYO145A, *Escherichia* virus EC6, *Escherichia* virus HY02, *Escherichia* virus JH2, *Escherichia* virus TP1, *Escherichia* virus VpaE1, *Escherichia* virus wV8, *Salmonella* virus FelixO1, *Salmonella* virus HB2014, *Salmonella* virus Mushroom, *Salmonella* virus UAB87, *Citrobacter* virus Moogle, *Citrobacter* virus Mordin, *Escherichia* virus SUSP1, *Escherichia* virus SUSP2, *Aeromonas* virus phiO18P, *Haemophilus* virus HP1, *Haemophilus* virus HP2, *Pasteurella* virus F108, *Vibrio* virus K139, *Vibrio* virus Kappa, *Burkholderia* virus phi52237, *Burkholderia* virus phiE122, *Burkholderia* virus phiE202, *Escherichia* virus 186, *Escherichia* virus P4, *Escherichia* virus P2, *Escherichia* virus Wphi, Mannheimia virus PHL101, *Pseudomonas* virus phiCTX, *Ralstonia* virus RSA1, *Salmonella* virus Fels2, *Salmonella* virus PsP3, *Salmonella* virus SopEphi, *Yersinia* virus L413C, *Staphylococcus* virus G1, *Staphylococcus* virus G15, *Staphylococcus* virus JD7, *Staphylococcus* virus K, *Staphylococcus* virus MCE2014, *Staphylococcus* virus P108, *Staphylococcus* virus Rodi, *Staphylococcus* virus 5253, *Staphylococcus* virus S25-4, *Staphylococcus* virus SA12, *Listeria* virus A511, *Listeria* virus P100, *Staphylococcus* virus Remus, *Staphylococcus* virus SA11, *Staphylococcus* virus Stau2, *Bacillus* virus Camphawk, *Bacillus* virus SPO1, *Bacillus* virus BCP78, *Bacillus* virus TsarBomba, *Staphylococcus* virus Twort, *Enterococcus* virus phiEC24C, *Lactobacillus* virus Lb338-1, *Lactobacillus* virus LP65, *Enterobacter* virus PG7, *Escherichia* virus CC31, *Klebsiella* virus JD18, *Klebsiella* virus PKO111, *Escherichia* virus Bp7, *Escherichia* virus IME08, *Escherichia* virus JS10, *Escherichia* virus JS98, *Escherichia* virus QL01, *Escherichia* virus VR5, *Enterobacter* virus Eap3, *Klebsiella* virus KP15, *Klebsiella* virus KP27, *Klebsiella* virus Matisse, *Klebsiella* virus Miro, *Citrobacter* virus Merlin, *Citrobacter* virus Moon, *Escherichia* virus JSE, *Escherichia* virus phi1, *Escherichia* virus RB49, *Escherichia* virus HX01, *Escherichia* virus JS09, *Escherichia* virus RB69, *Shigella* virus UTAM, *Salmonella* virus S16, *Salmonella* virus STML198, *Vibrio* virus KVP40, *Vibrio* virus nt1, *Vibrio* virus Va1KK3, *Escherichia* virus VR7, *Escherichia* virus VR20, *Escherichia* virus VR25, *Escherichia* virus VR26, *Shigella* virus SP18, *Escherichia* virus AR1, *Escherichia* virus C40, *Escherichia* virus E112, *Escherichia* virus ECML134, *Escherichia* virus HY01, *Escherichia* virus Ime09, *Escherichia* virus RB3, *Escherichia* virus RB14, *Escherichia* virus T4, *Shigella* virus Pss1, *Shigella* virus Shfl2, *Yersinia* virus D1, *Yersinia* virus PST, *Acinetobacter* virus 133, *Aeromonas* virus 65, *Aeromonas* virus Aeh1, *Escherichia* virus RB16, *Escherichia* virus RB32, *Escherichia* virus RB43, *Pseudomonas* virus 42, *Cronobacter* virus CR3, *Cronobacter* virus CR8, *Cronobacter* virus CR9, *Cronobacter* virus PBES02, *Pectobacterium* virus phiTE, *Cronobacter* virus GAP31, *Escherichia* virus 4MG, *Salmonella* virus SE1, *Salmonella* virus SSE121, *Escherichia* virus FFH2, *Escherichia* virus FV3, *Escherichia* virus JES2013, *Escherichia* virus VS, *Brevibacillus* virus Abouo, *Brevibacillus* virus Davies, *Bacillus* virus Agate, *Bacillus* virus Bobb, *Bacillus* virus Bp8pC, *Erwinia* virus Deimos, *Erwinia* virus Ea35-70, *Erwinia* virus RAY, *Erwinia* virus Simmy50, *Erwinia* virus SpecialG, *Acinetobacter* virus AB1, *Acinetobacter* virus AB2, *Acinetobacter* virus AbC62, *Acinetobacter* virus AP22, *Arthrobacter* virus ArV1, *Arthrobacter* virus Trina, *Bacillus* virus AvesoBmore, *Bacillus* virus B4, *Bacillus* virus Bigbertha, *Bacillus* virus Riley, *Bacillus* virus Spock, *Bacillus* virus Troll, *Bacillus* virus Bastille, *Bacillus* virus CAM003, *Bacillus* virus Bc431, *Bacillus* virus Bcp1, *Bacillus* virus BCP82, *Bacillus* virus BM15, *Bacillus* virus Deepblue, *Bacillus* virus JBP901, *Burkholderia* virus Bcep1, *Burkholderia* virus Bcep43, *Burkholderia* virus Bcep781, *Burkholderia* virus BcepNY3, *Xanthomonas* virus OP2, *Burkholderia* virus BcepMu, *Burkholderia* virus phiE255, *Aeromonas* virus 44RR2, *Mycobacterium* virus Alice, *Mycobacterium* virus Bxz1, *Mycobacterium* virus Dandelion, *Mycobacterium* virus HyRo, *Mycobacterium* virus 13, *Mycobacterium* virus Nappy, *Mycobacterium* virus Sebata, *Clostridium* virus phiC2, *Clostridium* virus phiCD27, *Clostridium* virus phiCD119, *Bacillus* virus CP51, *Bacillus* virus JL, *Bacillus* virus Shanette, *Escherichia* virus CVM10, *Escherichia* virus ep3, *Erwinia* virus Asesino, *Erwinia* virus EaH2, *Pseudomonas* virus EL, *Halomonas* virus HAP1, *Vibrio* virus VP882, *Brevibacillus* virus Jimmer, *Brevibacillus* virus Osiris, *Pseudomonas* virus Ab03, *Pseudomonas* virus KPP10, *Pseudomonas* virus PAKP3, *Sinorhizobium* virus M7, *Sinorhizobium* virus M12, *Sinorhizobium* virus N3, *Erwinia* virus Machina, *Arthrobacter* virus Brent, *Arthrobacter* virus Jawnski, *Arthrobacter* virus Martha, *Arthrobacter* virus Sonny, *Edwardsiella* virus MSW3, *Edwardsiella* virus PEi21, *Escherichia* virus Mu, *Shigella* virus SfMu, *Halobacterium* virus phiH, *Bacillus* virus Grass, *Bacillus* virus NIT1, *Bacillus* virus SPG24, *Aeromonas* virus 43, *Escherichia* virus P1, *Pseudomonas* virus CAb1, *Pseudomonas* virus CAb02, *Pseudomonas* virus JG004, *Pseudomonas* virus PAKP1, *Pseudomonas* virus PAKP4, *Pseudomonas* virus PaP1, *Burkholderia* virus BcepF1, *Pseudomonas* virus 141, *Pseudomonas* virus Ab28, *Pseudomonas* virus DL60, *Pseudomonas* virus DL68, *Pseudomonas* virus F8, *Pseudomonas* virus JG024, *Pseudomonas* virus KPP12, *Pseudomonas* virus LBL3, *Pseudomonas* virus LMA2, *Pseudomonas* virus PB1, *Pseudomonas* virus SN, *Pseudomonas* virus PA7, *Pseudomonas* virus phiKZ, *Rhizobium* virus RHEph4, *Ralstonia* virus RSF1, *Ralstonia* virus RSL2, *Ralstonia* virus RSL1, *Aeromonas* virus 25, *Aeromonas* virus 31, *Aeromonas* virus Aes12, *Aeromonas* virus Aes508, *Aeromonas* virus AS4, *Stenotrophomonas* virus IME13, *Staphylococcus* virus IPLAC1C, *Staphylococcus* virus SEP1, *Salmonella* virus SPN3US, *Bacillus* virus 1, *Geobacillus* virus GBSV1, *Yersinia* virus R1RT, *Yersinia* virus TG1, *Bacillus* virus G, *Bacillus* virus PBS1, *Microcystis* virus Ma-LMM01, *Vibrio* virus MAR, *Vibrio* virus VHML, *Vibrio* virus VP585, *Bacillus* virus BPS13, *Bacillus* virus Hakuna, *Bacillus* virus Megatron, *Bacillus* virus WPh, *Acinetobacter* virus AB3, *Acinetobacter* virus Abp1, *Acinetobacter* virus Fri1, *Acinetobacter* virus IME200, *Acinetobacter* virus PD6A3, *Acinetobacter* virus PDAB9, *Acinetobacter* virus phiAB1, *Escherichia* virus K30, *Klebsiella* virus K5, *Klebsiella* virus K11, *Klebsiella* virus Kp1, *Klebsiella* virus KP32, *Klebsiella* virus KpV289, *Klebsiella* virus F19, *Klebsiella* virus K244, *Klebsiella* virus Kp2, *Klebsiella* virus KP34, *Klebsiella* virus KpV41, *Klebsiella* virus KpV71, *Klebsiella* virus KpV475, *Klebsiella* virus SU503, *Klebsiella* virus SU552A, *Pantoea* virus Limelight, *Pantoea* virus Limezero, *Pseudomonas* virus LKA1, *Pseudomonas* virus phiKMV, *Xanthomonas* virus f20, *Xanthomonas* virus f30, *Xylella* virus Prado, *Erwinia* virus Era103, *Escherichia* virus K5, *Escherichia* virus K1-5, *Escherichia* virus K1E, *Salmonella* virus SP6, *Escherichia* virus T7, *Kluyvera* virus Kvp1, *Pseudomonas* virus gh1, *Prochlorococcus* virus PSSP7, *Synechococcus* virus P60, *Synechococcus* virus Syn5, *Streptococcus* virus Cp1, *Streptococcus* virus Cp7, *Staphylococcus* virus 44AHJD, *Streptococcus* virus C1, *Bacillus* virus B103, *Bacillus* virus GA1, *Bacillus* virus phi29, *Kurthia* virus 6, *Actinomyces* virus Av1, *Mycoplasma* virus P1, *Escherichia* virus 24B, *Escherichia* virus 933W, *Escherichia* virus Min27, *Escherichia* virus PA28, *Escherichia* virus Stx2 II, *Shigella* virus 7502Stx, *Shigella* virus POCJ13, *Escherichia* virus 191, *Escherichia* virus PA2, *Escherichia* virus TL2011, *Shigella* virus VASD, *Burkholderia* virus Bcep22, *Burkholderia* virus Bcepi102, *Burkholderia* virus Bcepmig1, *Burkholderia* virus DC1, *Bordetella* virus BPP1, *Burkholderia* virus BcepC6B, *Cellulophaga* virus Cba41, *Cellulophaga* virus Cba172, *Dinoroseobacter* virus DFL12, *Erwinia* virus Ea9-2, *Erwinia* virus Frozen, *Escherichia* virus phiV10, *Salmonella* virus Epsilon15, *Salmonella* virus SPN1S, *Pseudomonas* virus F116, *Pseudomonas* virus H66, *Escherichia* virus APEC5, *Escherichia* virus APEC7, *Escherichia* virus Bp4, *Escherichia* virus EC1UPM, *Escherichia* virus ECBP1, *Escherichia* virus G7C, *Escherichia* virus IME11, *Shigella* virus Sb1, *Achromobacter* virus Axp3, *Achromobacter* virus JWAlpha, *Edwardsiella* virus KF1, *Pseudomonas* virus KPP25, *Pseudomonas* virus R18, *Pseudomonas* virus Ab09, *Pseudomonas* virus LIT1, *Pseudomonas* virus PA26, *Pseudomonas* virus Ab22, *Pseudomonas* virus CHU, *Pseudomonas* virus LUZ24, *Pseudomonas* virus PAA2, *Pseudomonas* virus PaP3, *Pseudomonas* virus PaP4, *Pseudomonas* virus TL, *Pseudomonas* virus KPP21, *Pseudomonas* virus LUZ7, *Escherichia* virus N4, *Salmonella* virus 9NA, *Salmonella* virus SP069, *Salmonella* virus BTP1, *Salmonella* virus HK620, *Salmonella* virus P22, *Salmonella* virus ST64T, *Shigella* virus Sf6, *Bacillus* virus Page, *Bacillus* virus Palmer, *Bacillus* virus Pascal, *Bacillus* virus Pony, *Bacillus* virus Pookie, *Escherichia* virus 172-1, *Escherichia* virus ECB2, *Escherichia* virus NJ01, *Escherichia* virus phiEco32, *Escherichia* virus Septima11, *Escherichia* virus SU10, *Brucella* virus Pr, *Brucella* virus Tb, *Escherichia* virus Pollock, *Salmonella* virus FSL SP-058, *Salmonella* virus FSL SP-076, *Helicobacter* virus 1961P, *Helicobacter* virus KHP30, *Helicobacter* virus KHP40, *Hamiltonella* virus APSE1, *Lactococcus* virus KSY1, *Phormidium* virus WMP3, *Phormidium* virus WMP4, *Pseudomonas* virus 119X, *Roseobacter* virus SIO1, *Vibrio* virus VpV262, *Vibrio* virus VC8, *Vibrio* virus VP2, *Vibrio* virus VP5, *Streptomyces* virus Amela, *Streptomyces* virus phiCAM, *Streptomyces* virus Aaronocolus, *Streptomyces* virus Caliburn, *Streptomyces* virus Danzina, *Streptomyces* virus Hydra, *Streptomyces* virus Izzy, *Streptomyces* virus Lannister, *Streptomyces* virus Lika, *Streptomyces* virus Sujidade, *Streptomyces* virus Zemlya, *Streptomyces* virus ELB20, *Streptomyces* virus R4, *Streptomyces* virus phiHau3, *Mycobacterium* virus Acadian, *Mycobacterium* virus Baee, *Mycobacterium* virus Reprobate, *Mycobacterium* virus Adawi, *Mycobacterium* virus Bane1, *Mycobacterium* virus BrownCNA, *Mycobacterium* virus Chrisnmich, *Mycobacterium* virus Cooper, *Mycobacterium* virus JAMaL, *Mycobacterium* virus Nigel, *Mycobacterium* virus Stinger, *Mycobacterium* virus Vincenzo, *Mycobacterium* virus Zemanar, *Mycobacterium* virus Apizium, *Mycobacterium* virus Manad, *Mycobacterium* virus Oline, *Mycobacterium* virus Osmaximus, *Mycobacterium* virus Pg1, *Mycobacterium* virus Soto, *Mycobacterium* virus Suffolk, *Mycobacterium* virus Athena, *Mycobacterium* virus Bernardo, *Mycobacterium* virus Gadjet, *Mycobacterium* virus Pipefish, *Mycobacterium* virus Godines, *Mycobacterium* virus Rosebush, *Mycobacterium* virus Babsiella, *Mycobacterium* virus Brujita, *Mycobacterium* virus Che9c, *Mycobacterium* virus Sbash, *Mycobacterium* virus Hawkeye, *Mycobacterium* virus Plot, *Salmonella* virus AG11, *Salmonella* virus Ent1, *Salmonella* virus f18SE, *Salmonella* virus Jersey, *Salmonella* virus L13, *Salmonella* virus LSPA1, *Salmonella* virus SE2, *Salmonella* virus SETP3, *Salmonella* virus SETP7, *Salmonella* virus SETP13, *Salmonella* virus SP101, *Salmonella* virus SS3e, *Salmonella* virus wks13, *Escherichia* virus K1G, *Escherichia* virus K1H, *Escherichia* virus K1ind1, *Escherichia* virus K1ind2, *Salmonella* virus SP31, *Leuconostoc* virus Lmd1, *Leuconostoc* virus LN03, *Leuconostoc* virus LN04, *Leuconostoc* virus LN12, *Leuconostoc* virus LN6B, *Leuconostoc* virus P793, *Leuconostoc* virus 1A4, *Leuconostoc* virus Ln8, *Leuconostoc* virus Ln9, *Leuconostoc* virus LN25, *Leuconostoc* virus LN34, *Leuconostoc* virus LNTR3, *Mycobacterium* virus Bongo, *Mycobacterium* virus Rey, *Mycobacterium* virus Butters, *Mycobacterium* virus Michelle, *Mycobacterium* virus Charlie, *Mycobacterium* virus Pipsqueaks, *Mycobacterium* virus Xeno, *Mycobacterium* virus Panchino, *Mycobacterium* virus Phrann, *Mycobacterium* virus Redi, *Mycobacterium* virus Skinnyp, *Gordonia* virus BaxterFox, *Gordonia* virus Yeezy, *Gordonia* virus Kita, *Gordonia* virus Zirinka, *Gorrdonia* virus Nymphadora, *Mycobacterium* virus Bignuz, *Mycobacterium* virus Brusacoram, *Mycobacterium* virus Donovan, *Mycobacterium* virus Fishburne, *Mycobacterium* virus Jebeks, *Mycobacterium* virus Malithi, *Mycobacterium* virus Phayonce, *Enterobacter* virus F20, *Klebsiella* virus 1513, *Klebsiella* virus KLPN1, *Klebsiella* virus KP36, *Klebsiella* virus PKP126, *Klebsiella* virus Sushi, *Escherichia* virus AHP42, *Escherichia* virus AHS24, *Escherichia* virus AKS96, *Escherichia* virus C119, *Escherichia* virus E41c, *Escherichia* virus Eb49, *Escherichia* virus Jk06, *Escherichia* virus KP26, *Escherichia* virus Rogue1, *Escherichia* virus ACGM12, *Escherichia* virus Rtp, *Escherichia* virus ADB2, *Escherichia* virus JMPW1, *Escherichia* virus JMPW2, *Escherichia* virus T1, *Shigella* virus PSf2, *Shigella* virus Shfl1, *Citrobacter* virus Stevie, *Escherichia* virus TLS, *Salmonella* virus SP126, Cronobacter virus Esp2949-1, *Pseudomonas* virus Ab18, *Pseudomonas* virus Ab19, *Pseudomonas* virus PaMx11, *Arthrobacter* virus Amigo, *Propionibacterium* virus Anatole, *Propionibacterium* virus B3, *Bacillus* virus Andromeda, *Bacillus* virus Blastoid, *Bacillus* virus Curly, *Bacillus* virus Eoghan, *Bacillus* virus Finn, *Bacillus* virus Glittering, *Bacillus* virus Riggi, *Bacillus* virus Taylor, *Gordonia* virus Attis, *Mycobacterium* virus Barnyard, *Mycobacterium* virus Konstantine, *Mycobacterium* virus Predator, *Mycobacterium* virus Bernal13, *Staphylococcus* virus 13, *Staphylococcus* virus 77, *Staphylococcus* virus 108PVL, *Mycobacterium* virus Bron, *Mycobacterium* virus Faith1, *Mycobacterium* virus Joedirt, *Mycobacterium* virus Rumpelstiltskin, *Lactococcus* virus bIL67, *Lactococcus* virus c2, *Lactobacillus* virus c5, *Lactobacillus* virus Ld3, *Lactobacillus* virus Ld17, *Lactobacillus* virus Ld25A, *Lactobacillus* virus LLKu, *Lactobacillus* virus phiLdb, Cellulophaga virus Cba121, Cellulophaga virus Cba171, Cellulophaga virus Cba181, Cellulophaga virus ST, *Bacillus* virus 250, *Bacillus* virus IEBH, *Mycobacterium* virus Ardmore, *Mycobacterium* virus Avani, *Mycobacterium* virus Boomer, *Mycobacterium* virus Che8, *Mycobacterium* virus Che9d, *Mycobacterium* virus Deadp, *Mycobacterium* virus Dlane, *Mycobacterium* virus Dorothy, *Mycobacterium* virus Dotproduct, *Mycobacterium* virus Drago, *Mycobacterium* virus Fruitloop, *Mycobacterium* virus Gumbie, *Mycobacterium* virus Ibhubesi, *Mycobacterium* virus Llij, *Mycobacterium* virus Mozy, *Mycobacterium* virus Mutaforma13, *Mycobacterium* virus Pacc40, *Mycobacterium* virus PMC, *Mycobacterium* virus Ramsey, *Mycobacterium* virus Rockyhorror, *Mycobacterium* virus SG4, *Mycobacterium* virus Shaunal, *Mycobacterium* virus Shilan, *Mycobacterium* virus Spartacus, *Mycobacterium* virus Taj, *Mycobacterium* virus Tweety, *Mycobacterium* virus Wee, *Mycobacterium* virus Yoshi, *Salmonella* virus Chi, *Salmonella* virus FSLSP030, *Salmonella* virus FSLSP088, *Salmonella* virus iEPS5, *Salmonella* virus SPN19, *Mycobacterium* virus 244, *Mycobacterium* virus Bask21, *Mycobacterium* virus CJW1, *Mycobacterium* virus Eureka, *Mycobacterium* virus Kostya, *Mycobacterium* virus Porky, *Mycobacterium* virus Pumpkin, *Mycobacterium* virus Sirduracell, *Mycobacterium* virus Toto, *Mycobacterium* virus Corndog, *Mycobacterium* virus Firecracker, *Rhodobacter* virus RcCronus, *Pseudomonas* virus D3112, *Pseudomonas* virus DMS3, *Pseudomonas* virus FHA0480, *Pseudomonas* virus LPB1, *Pseudomonas* virus MP22, *Pseudomonas* virus MP29, *Pseudomonas* virus MP38, *Pseudomonas* virus PA1KOR, *Pseudomonas* virus D3, *Pseudomonas* virus PMG1, *Arthrobacter* virus Decurro, *Gordonia* virus Demosthenes, *Gordonia* virus Katyusha, *Gordonia* virus Kvothe, *Propionibacterium* virus B22, *Propionibacterium* virus Doucette, *Propionibacterium* virus E6, *Propionibacterium* virus G4, *Burkholderia* virus phi6442, *Burkholderia* virus phi1026b, *Burkholderia* virus phiE125, *Edwardsiella* virus eiAU, *Mycobacterium* virus Ff47, *Mycobacterium* virus Muddy, *Mycobacterium* virus Gaia, *Mycobacterium* virus Giles, *Arthrobacter* virus Captnmurica, *Arthrobacter* virus Gordon, *Gordonia* virus GordTnk2, *Paenibacillus* virus Harrison, *Escherichia* virus EK99P1, *Escherichia* virus HK578, *Escherichia* virus JL1, *Escherichia* virus SSL2009a, *Escherichia* virus YD2008s, *Shigella* virus EP23, Sodalis virus SO1, *Escherichia* virus HK022, *Escherichia* virus HK75, *Escherichia* virus HK97, *Escherichia* virus HK106, *Escherichia* virus HK446, *Escherichia* virus HK542, *Escherichia* virus HK544, *Escherichia* virus HK633, *Escherichia* virus mEp234, *Escherichia* virus mEp235, *Escherichia* virus mEpX1, *Escherichia* virus mEpX2, *Escherichia* virus mEp043, *Escherichia* virus mEp213, *Escherichia* virus mEp237, *Escherichia* virus mEp390, *Escherichia* virus mEp460, *Escherichia* virus mEp505, *Escherichia* virus mEp506, *Brevibacillus* virus Jenst, *Achromobacter* virus 83-24, *Achromobacter* virus JWX, *Arthrobacter* virus Kellezzio, *Arthrobacter* virus Kitkat, *Arthrobacter* virus Bennie, *Arthrobacter* virus DrRobert, *Arthrobacter* virus Glenn, *Arthrobacter* virus HunterDalle, *Arthrobacter* virus Joann, *Arthrobacter* virus Korra, *Arthrobacter* virus Preamble, *Arthrobacter* virus Pumancara, *Arthrobacter* virus Wayne, *Mycobacterium* virus Alma, *Mycobacterium* virus Arturo, *Mycobacterium* virus Astro, *Mycobacterium* virus Backyardigan, *Mycobacterium* virus BBPiebs31, *Mycobacterium* virus Benedict, *Mycobacterium* virus Bethlehem, *Mycobacterium* virus Billknuckles, *Mycobacterium* virus Bruns, *Mycobacterium* virus Bxb1, *Mycobacterium* virus Bxz2, *Mycobacterium* virus Che12, *Mycobacterium* virus Cuco, *Mycobacterium* virus D29, *Mycobacterium* virus Doom, *Mycobacterium* virus Ericb, *Mycobacterium* virus Euphoria, *Mycobacterium* virus George, *Mycobacterium* virus Gladiator, *Mycobacterium* virus Goose, *Mycobacterium* virus Hammer, *Mycobacterium* virus Heldan, *Mycobacterium* virus Jasper, *Mycobacterium* virus JC27, *Mycobacterium* virus Jeffabunny, *Mycobacterium* virus JHC117, *Mycobacterium* virus KBG, *Mycobacterium* virus Kssjeb, *Mycobacterium* virus Kugel, *Mycobacterium* virus L5, *Mycobacterium* virus Lesedi, *Mycobacterium* virus LHTSCC, *Mycobacterium* virus lockley, *Mycobacterium* virus Marcell, *Mycobacterium* virus Microwolf, *Mycobacterium* virus Mrgordo, *Mycobacterium* virus Museum, *Mycobacterium* virus Nepal, *Mycobacterium* virus Packman, *Mycobacterium* virus Peaches, *Mycobacte-* rium virus Perseus, *Mycobacterium* virus Pukovnik, *Mycobacterium* virus Rebeuca, *Mycobacterium* virus Redrock, *Mycobacterium* virus Ridgecb, *Mycobacterium* virus Rockstar, *Mycobacterium* virus Saintus, *Mycobacterium* virus Skipole, *Mycobacterium* virus Solon, *Mycobacterium* virus Switzer, *Mycobacterium* virus SWU1, *Mycobacterium* virus Ta17a, *Mycobacterium* virus Tiger, *Mycobacterium* virus Timshe1, *Mycobacterium* virus Trixie, *Mycobacterium* virus Turbido, *Mycobacterium* virus Twister, *Mycobacterium* virus U2, *Mycobacterium* virus Violet, *Mycobacterium* virus Wonder, *Escherichia* virus DE3, *Escherichia* virus HK629, *Escherichia* virus HK630, *Escherichia* virus Lambda, *Arthrobacter* virus Laroye, *Mycobacterium* virus Halo, *Mycobacterium* virus Liefie, *Mycobacterium* virus Marvin, *Mycobacterium* virus Mosmoris, *Arthrobacter* virus Circum, *Arthrobacter* virus Mudcat, *Escherichia* virus N15, *Escherichia* virus 9g, *Escherichia* virus JenK1, *Escherichia* virus JenP1, *Escherichia* virus JenP2, *Pseudomonas* virus NP1, *Pseudomonas* virus PaMx25, *Mycobacterium* virus Baka, *Mycobacterium* virus Courthouse, *Mycobacterium* virus Littlee, *Mycobacterium* virus Omega, *Mycobacterium* virus Optimus, *Mycobacterium* virus Thibault, *Polaribacter* virus P12002L, *Polaribacter* virus P12002S, *Nonlabens* virus P12024L, *Nonlabens* virus P12024S, *Thermus* virus P23-45, *Thermus* virus P74-26, *Listeria* virus LP26, *Listeria* virus LP37, *Listeria* virus LP110, *Listeria* virus LP114, *Listeria* virus P70, *Propionibacterium* virus ATCC29399BC, *Propionibacterium* virus ATCC29399BT, *Propionibacterium* virus Attacne, *Propionibacterium* virus Keiki, *Propionibacterium* virus Kubed, *Propionibacterium* virus Lauchelly, *Propionibacterium* virus MrAK, *Propionibacterium* virus Ouroboros, *Propionibacterium* virus P91, *Propionibacterium* virus P105, *Propionibacterium* virus P144, *Propionibacterium* virus P1001, *Propionibacterium* virus P1.1, *Propionibacterium* virus P100A, *Propionibacterium* virus P100D, *Propionibacterium* virus P101A, *Propionibacterium* virus P104A, *Propionibacterium* virus PA6, *Propionibacterium* virus Pacnes201215, *Propionibacterium* virus PAD20, *Propionibacterium* virus PAS50, *Propionibacterium* virus PHL009M11, *Propionibacterium* virus PHL025M00, *Propionibacterium* virus PHL037M02, *Propionibacterium* virus PHL041M10, *Propionibacterium* virus PHL060L00, *Propionibacterium* virus PHL067M01, *Propionibacterium* virus PHL070N00, *Propionibacterium* virus PHL071N05, *Propionibacterium* virus PHL082M03, *Propionibacterium* virus PHL092M00, *Propionibacterium* virus PHL095N00, *Propionibacterium* virus PHL111M01, *Propionibacterium* virus PHL112N00, *Propionibacterium* virus PHL113M01, *Propionibacterium* virus PHL114L00, *Propionibacterium* virus PHL116M00, *Propionibacterium* virus PHL117M00, *Propionibacterium* virus PHL117M01, *Propionibacterium* virus PHL132N00, *Propionibacterium* virus PHL141N00, *Propionibacterium* virus PHL151M00, *Propionibacterium* virus PHL151N00, *Propionibacterium* virus PHL152M00, *Propionibacterium* virus PHL163M00, *Propionibacterium* virus PHL171M01, *Propionibacterium* virus PHL179M00, *Propionibacterium* virus PHL194M00, *Propionibacterium* virus PHL199M00, *Propionibacterium* virus PHL301M00, *Propionibacterium* virus PHL308M00, *Propionibacterium* virus Pirate, *Propionibacterium* virus Procrass1, *Propionibacterium* virus SKKY, *Propionibacterium* virus Solid, *Propionibacterium* virus Stormborn, *Propionibacterium* virus Wizzo, *Pseudomonas* virus PaMx28, *Pseudomonas* virus PaMx74, *Mycobacterium* virus Patience, *Mycobacterium* virus PBI1, *Rhodococcus* virus Pepy6, *Rhodococcus* virus Poco6, *Propionibacterium* virus PFR1, *Streptomyces* virus phiBT1, *Streptomyces* virus phiC31, *Streptomyces* virus TG1, *Caulobacter* virus Karma, *Caulobacter* virus Magneto, *Caulobacter* virus phiCbK, *Caulobacter* virus Rogue, *Caulobacter* virus Swift, *Staphylococcus* virus 11, *Staphylococcus* virus 29, *Staphylococcus* virus 37, *Staphylococcus* virus 53, *Staphylococcus* virus 55, *Staphylococcus* virus 69, *Staphylococcus* virus 71, *Staphylococcus* virus 80, *Staphylococcus* virus 85, *Staphylococcus* virus 88, *Staphylococcus* virus 92, *Staphylococcus* virus 96, *Staphylococcus* virus 187, *Staphylococcus* virus 52a, *Staphylococcus* virus 80alpha, *Staphylococcus* virus CNPH82, *Staphylococcus* virus EW, *Staphylococcus* virus IPLA5, *Staphylococcus* virus IPLA7, *Staphylococcus* virus IPLA88, *Staphylococcus* virus PH15, *Staphylococcus* virus phiETA, *Staphylococcus* virus phiETA2, *Staphylococcus* virus phiETA3, *Staphylococcus* virus phiMR11, *Staphylococcus* virus phiMR25, *Staphylococcus* virus phiNM1, *Staphylococcus* virus phiNM2, *Staphylococcus* virus phiNM4, *Staphylococcus* virus SAP26, *Staphylococcus* virus X2, *Enterococcus* virus FL1, *Enterococcus* virus FL2, *Enterococcus* virus FL3, *Lactobacillus* virus ATCC8014, *Lactobacillus* virus phiJL1, *Pediococcus* virus cIP1, *Aeromonas* virus pIS4A, *Listeria* virus LP302, *Listeria* virus PSA, *Methanobacterium* virus psiM1, Roseobacter virus RDJL1, Roseobacter virus RDJL2, *Rhodococcus* virus RER2, *Enterococcus* virus BC611, *Enterococcus* virus IMEEF1, *Enterococcus* virus SAP6, *Enterococcus* virus VD13, *Streptococcus* virus SPQS1, *Mycobacterium* virus Papyrus, *Mycobacterium* virus Send513, *Burkholderia* virus KL1, *Pseudomonas* virus 73, *Pseudomonas* virus Ab26, *Pseudomonas* virus Kakheti25, *Escherichia* virus Cajan, *Escherichia* virus Seurat, *Staphylococcus* virus SEP9, *Staphylococcus* virus Sextaec, *Streptococcus* virus 858, *Streptococcus* virus 2972, *Streptococcus* virus ALQ132, *Streptococcus* virus 01205, *Streptococcus* virus Sfi11, *Streptococcus* virus 7201, *Streptococcus* virus DT1, *Streptococcus* virus phiAbc2, *Streptococcus* virus Sfi19, *Streptococcus* virus Sfi21, *Paenibacillus* virus Diva, *Paenibacillus* virus Hb10c2, *Paenibacillus* virus Rani, *Paenibacillus* virus Shelly, *Paenibacillus* virus Sitara, *Paenibacillus* virus Willow, *Lactococcus* virus 712, *Lactococcus* virus ASCC191, *Lactococcus* virus ASCC273, *Lactococcus* virus ASCC281, *Lactococcus* virus ASCC465, *Lactococcus* virus ASCC532, *Lactococcus* virus Bibb29, *Lactococcus* virus bIL170, *Lactococcus* virus CB13, *Lactococcus* virus CB14, *Lactococcus* virus CB19, *Lactococcus* virus CB20, *Lactococcus* virus jj50, *Lactococcus* virus P2, *Lactococcus* virus P008, *Lactococcus* virus sk1, *Lactococcus* virus S14, *Bacillus* virus Slash, *Bacillus* virus Stahl, *Bacillus* virus Staley, *Bacillus* virus Stills, *Gordonia* virus Bachita, *Gordonia* virus ClubL, *Gordonia* virus OneUp, *Gordonia* virus Smoothie, *Gordonia* virus Soups, *Bacillus* virus SPbeta, *Vibrio* virus MAR10, *Vibrio* virus SSP002, *Escherichia* virus AKFV33, *Escherichia* virus BF23, *Escherichia* virus DT57C, *Escherichia* virus EPS7, *Escherichia* virus FFH1, *Escherichia* virus H8, *Escherichia* virus slur09, *Escherichia* virus T5, *Salmonella* virus 118970sa12, *Salmonella* virus Shivani, *Salmonella* virus SPC35, *Salmonella* virus Stitch, *Arthrobacter* virus Tank, *Tsukamurella* virus TIN2, *Tsukamurella* virus TIN3, *Tsukamurella* virus TIN4, *Rhodobacter* virus RcSpartan, *Rhodobacter* virus RcTitan, *Mycobacterium* virus Anaya, *Mycobacterium* virus Angelica, *Mycobacterium* virus Crimd, *Mycobacterium* virus Fionnbarth, *Mycobacterium* virus Jaws, *Mycobacterium* virus Larva, *Mycobacterium* virus Macncheese, *Mycobacterium* virus Pixie, *Mycobacterium* virus TM4, *Bacillus* virus BMBtp2, *Bacillus* virus TP21, *Geobacillus* virus Tp84, *Staphylococcus* virus 47, *Staphylococcus* virus 3a, *Staphylococcus* virus 42e, *Staphy-* lococcus virus IPLA35, *Staphylococcus* virus phi12, *Staphylococcus* virus phiSLT, *Mycobacterium* virus 32HC, *Rhodococcus* virus RGL3, *Paenibacillus* virus Vegas, *Gordonia* virus Vendetta, *Bacillus* virus Wbeta, *Mycobacterium* virus Wildcat, *Gordonia* virus Twister6, *Gordonia* virus Wizard, *Gordonia* virus Hotorobo, *Gordonia* virus Monty, *Gordonia* virus Woes, *Xanthomonas* virus CP1, *Xanthomonas* virus OP1, *Xanthomonas* virus phi17, *Xanthomonas* virus Xop411, *Xanthomonas* virus Xp10, *Streptomyces* virus TP1604, *Streptomyces* virus YDN12, Alphaproteobacteria virus phiJ1001, *Pseudomonas* virus LKO4, *Pseudomonas* virus M6, *Pseudomonas* virus MP1412, *Pseudomonas* virus PAE1, *Pseudomonas* virus Yua, *Pseudoalteromonas* virus PM2, *Pseudomonas* virus phi6, *Pseudomonas* virus phi8, *Pseudomonas* virus phi12, *Pseudomonas* virus phi13, *Pseudomonas* virus phi2954, *Pseudomonas* virus phiNN, *Pseudomonas* virus phiYY, *Vibrio* virus fs1, *Vibrio* virus VGJ, *Ralstonia* virus RS603, *Ralstonia* virus RSM1, *Ralstonia* virus RSM3, *Escherichia* virus M13, *Escherichia* virus 122, *Salmonella* virus IKe, Acholeplasma virus L51, *Vibrio* virus fs2, *Vibrio* virus VFJ, *Escherichia* virus If1, *Propionibacterium* virus B5, *Pseudomonas* virus Pf1, *Pseudomonas* virus Pf3, *Ralstonia* virus PE226, *Ralstonia* virus RSS1, Spiroplasma virus SVTS2, *Stenotrophomonas* virus PSH1, *Stenotrophomonas* virus SMA6, *Stenotrophomonas* virus SMA7, *Stenotrophomonas* virus SMA9, *Vibrio* virus CTXphi, *Vibrio* virus KSF1, *Vibrio* virus VCY, *Vibrio* virus Vf33, *Vibrio* virus VfO3K6, *Xanthomonas* virus Cf1c, Spiroplasma virus C74, Spiroplasma virus R8A2B, Spiroplasma virus SkV1CR23x, *Escherichia* virus FI, *Escherichia* virus Qbeta, *Escherichia* virus BZ13, *Escherichia* virus MS2, *Escherichia* virus alpha3, *Escherichia* virus ID21, *Escherichia* virus ID32, *Escherichia* virus ID62, *Escherichia* virus NC28, *Escherichia* virus NC29, *Escherichia* virus NC35, *Escherichia* virus phiK, *Escherichia* virus St1, *Escherichia* virus WA45, *Escherichia* virus G4, *Escherichia* virus ID52, *Escherichia* virus Talmos, *Escherichia* virus phiX174, Bdellovibrio virus MAC1, Bdellovibrio virus MH2K, *Chlamydia* virus Chp1, *Chlamydia* virus Chp2, *Chlamydia* virus CPAR39, *Chlamydia* virus CPG1, Spiroplasma virus SpV4, Acholeplasma virus L2, *Pseudomonas* virus PR4, *Pseudomonas* virus PRD1, *Bacillus* virus AP50, *Bacillus* virus Bam35, *Bacillus* virus GIL16, *Bacillus* virus Wip1, *Escherichia* virus phi80, *Escherichia* virus RB42, *Escherichia* virus T2, *Escherichia* virus T3, *Escherichia* virus T6, *Escherichia* virus VT2-Sa, *Escherichia* virus VT1-Sakai, *Escherichia* virus VT2-Sakai, *Escherichia* virus CP-933V, *Escherichia* virus P27, *Escherichia* virus Stx2phi-I, *Escherichia* virus Stx1phi, *Escherichia* virus Stx2phi-II, *Escherichia* virus CP-1639, based on the *Escherichia* virus BP-4795, *Escherichia* virus 86, *Escherichia* virus Min27, *Escherichia* virus 2851, *Escherichia* virus 1717, *Escherichia* virus YYZ-2008, *Escherichia* virus EC026_P06, *Escherichia* virus ECO103_P15, *Escherichia* virus ECO103_P12, *Escherichia* virus ECO111_P16, *Escherichia* virus ECO111_P11, *Escherichia* virus VT2phi_272, *Escherichia* virus TL-2011c, *Escherichia* virus P13374, *Escherichia* virus Spy.

In one embodiment, the bacterial virus particles target *E. coli* and includes the capsid of a bacteriophage selected in the group consisting of BW73, B278, D6, D108, E, E1, E24, E41, FI-2, FI-4, FI-5, HI8A, Ff18B, i, MM, Mu, 025, PhI-5, Pk, PSP3, P1, P1D, P2, P4, S1, Wφ, φK13, φ1, φ2, φ7, φ92, 7 A, 8φ, 9φ, 18, 28-1, 186, 299, HH-*Escherichia* (2), AB48, CM, C4, C16, DD-VI, E4, E7, E28, FI1, FI3, H, H1, H3, H8, K3, M, N, ND-2, ND-3, ND4, ND-5, ND6, ND-7, Ox-I, Ox-2, Ox-3, Ox-4, Ox-5, Ox-6, PhI-I, RB42, RB43, RB49, RB69, S, SaI-I, Sa1-2, Sa1-3, Sa1-4, Sa1-5, Sa1-6, TC23, TC45, TuII*-6, TuIP-24, TuII*46, TuIP-60, T2, T4, T6, T35, α1, 1, IA, 3, 3A, 3T+, 5φ, 9266Q, CFO103, HK620, J, K, K1F, m59, no. A, no. E, no. 3, no. 9, N4, sd, T3, T7, WPK, W31, ΔH, φC3888, φK3, φK7, φK12, φV-1, Φ04-CF, Φ05, Φ06, Φ07, φ1, φ1.2, φ20, φ95, φ263, φ1O92, φ1, φ11, Ω8, 1, 3, 7, 8, 26, 27, 28-2, 29, 30, 31, 32, 38, 39, 42, 933W, NN-*Escherichia* (1), Esc-7-11, AC30, CVX-5, C1, DDUP, EC1, EC2, E21, E29, F1, F26S, F27S, Hi, HK022, HK97, HK139, HK253, HK256, K7, ND-I, PA-2, q, S2, T1,), T3C, T5, UC-I, w, β4, γ2, λ, ΦD326, φγ, Φ06, Φ7, Φ10, φ80, χ, 2, 4, 4A, 6, 8A, 102, 150, 168, 174, 3000, AC6, AC7, AC28, AC43, AC50, AC57, AC81, AC95, HK243, K1O, ZG/3A, 5, 5A, 21EL, H19-J and 933H.

Bacterial Delivery Vehicle

In one aspect, the bacterial delivery vehicle is a bacterial virus particle. In such embodiment, the payload may be a plasmid. Particularly, the invention may concern a bacterial virus particle with the plasmid according to the invention as disclosed hereabove (in particular it comprises at least two packaging sites) encapsidated into the particle. It also relates to a combination of at least two different bacterial virus particles, said different bacterial virus particles having the same plasmid encapsidated into the particles.

The different bacterial delivery vehicles are capable of targeting at least two different bacteria and of introducing the plasmid into said bacteria. Alternatively, the different bacterial virus particles are capable of targeting the same bacteria and of introducing the payload into said bacteria. The spectra of the population of bacterial virus particles is defined according to the bacteriophages infection spectra, as describe hereabove.

The particles may comprise the capsid of bacteriophages selected of in the group consisting of lambda derived capsids, P4 derived capsids, M13-derived capsids, P1 derived capsids (see, e.g., Westwater C A et al., Microbiology 148, 943-50 (2002); Kittleson J T et al., ACS Synthetoc Biology 1, 583-89 (2012); Mead D A et al, Biotechnology 10, 85-102 (1988)).

Optionally, the phagemid is selected from the group consisting of lambda derived phagemids, P4 derived phagemids, M13-derived phagemids, such as the ones containing the fl origin for filamentous phage packaging such as, for example, pBluescript II SK (+/−) and KS (+/−) phagemids, pBC SK and KS phagemids, pADL and P1 derived phagemids, preferably phagemids according to the invention are selected from lambda derived phagemids and P4 derived phagemids, more preferably, phagemids according to the invention are selected from lambda derived phagemids, preferably selected from the group consisting of HK022 derived phagemids, mEP237 derived phagemids, HK97 derived phagemids, HK629 derived phagemids, HK630 derived phagemids, mEP043 derived phagemids, mEP213 derived phagemids, mEP234 derived phagemids, mEP390 derived phagemids, mEP460 derived phagemids, mEPx1 derived phagemids, mEPx2 derived phagemids, phi80 derived phagemids and mEP234 derived phagemids.

In a preferred embodiment, the bacterial delivery vehicles comprise the capsid of bacteriophages selected in the group consisting of P2, P4, λ, and 186.

In an even more preferred embodiment, the bacterial delivery vehicles comprise the capsid of bacteriophages P2 and λ.

More preferably, the bacterial delivery vehicles may comprise the capsid of bacteriophages selected from lambda derived capsids, preferably selected from the group consisting of HK022 derived capsids, mEP237 derived capsids, HK97 derived capsids, HK629 derived capsids, HK630 derived capsids, mEP043 derived capsids, mEP213 derived capsids, mEP234 derived capsids, mEP390 derived capsids, mEP460 derived capsids, mEPx1 derived capsids, mEPx2 derived capsids, phi80 derived capsids, mEP234 derived capsids.

Method for Preparing the Bacterial Virus Particles—Producing Bacteria

In another aspect, a method is provided for preparing a population of at least two different bacterial virus particles containing the same payload.

In this particular aspect, the method comprises the introduction of the payload according to the invention into bacteria, the production bacteria. For instance, in the embodiment where the bacterial delivery vehicle are bacterial virus particles, the bacteria can be infected (i.e. according to the bacteriophage spectra known by the person skilled in the art). Alternatively, the bacteria can be transfected by the payload according to the invention.

The bacterium is suitable for the replication of the payload according to the invention and its packaging into at least one of the different bacterial delivery vehicles. For this purpose, the bacteria may further comprise satellite or helper phages genes to promote the packaging of the payload. The bacteria express the structural and functional proteins necessary to promote an in vitro packaging of the payload in a bacterial delivery vehicle, particularly in a bacterial virus particle. In particular, the bacteria express the protein of the particle, namely the capsid or coat proteins.

In one aspect, a first bacterium is used for producing the payload packaged into a first bacterial delivery vehicle and a second bacterium is used for producing the same payload packaged into a second bacterial virus particle. Then, for each bacterial virus particle, a specific bacterium is used for the production of the payload packaged into a particular bacterial virus particle. Accordingly, each specific bacterium comprises satellite or helper phage genes to promote the packaging of the payload into the particular bacterial virus particle. In particular, the first bacterium expresses the structural and functional proteins necessary to promote an intracellular (i.e. intrabacterial) packaging of the payload into a first bacterial virus particle; and the second bacterium expresses the structural and functional proteins necessary to promote an intracellular packaging of the payload into a second bacterial virus particle. In one embodiment, the first bacterium expresses the capsid or coat proteins of a first bacterial virus particle; and the second bacterium expresses the capsid or coat proteins of a second bacterial virus particle. Of course, if more than two bacterial virus particles are contemplated, the same applies to the additional bacterial virus particles. The present invention also relates to a kit comprising such a first and second bacteria and so on.

In another aspect, one bacterium is used for producing the payload packaged into a first bacterial delivery vehicle and a second bacterial delivery vehicle. Then, for a combination of at least two bacterial delivery vehicles, a bacterium is used for the production of the payload packaged into at least two different bacterial delivery vehicles. Accordingly, a bacterium comprises satellite or helper phages genes to promote the packaging of the payload into at least two different bacterial delivery vehicles, preferably into at least two different bacterial virus particles. In particular, the bacterium expresses the structural and functional proteins necessary to promote an intracellular packaging of the payload into a first bacterial delivery vehicle and a second bacterial virus particle. In one embodiment, the bacterium expresses the capsid or coat proteins of a first bacterial virus particle and of a second bacterial virus particle. Of course, if more than two bacterial virus particles are contemplated, the same applies to the additional bacterial virus particles.

Then, the method comprises:
providing the payload as defined above;
introducing said payload into bacteria, the bacteria being suitable for packaging the payload into a bacterial delivery vehicle; and
packaging the payload into the bacterial delivery vehicles.

The method may further comprise a step of recovering the bacterial delivery vehicles having the payload packaged into them.

The introduction of the payload into bacteria can be carried out by transfection or by injection.

Such methods may further comprise the use of a helper phage to promote the packaging in at least two different delivery vehicles. It is known by the person skilled in the art that some bacteriophages are defective and need a helper phage for replication and/or packaging. Thus, compatible pairs of principal phage and helper phage are easily made by the person skilled in the art to promote an efficient payload packaging. Such Helper phage can be but are not limited to M13KO7, R408, VCSM13, KM13 (Res Microbiol (2001) 152, 187-191), M13MDD3.2 (FEMS Microbiol Lett (1995) 125, 317-321), R408d3 (Gene (1997) 198, 99-103), VCSM13d3 (Gene (1997) 198, 99-103), Hyperphage (Nat Biotechnol (2001) 19, 75-78), CT helper phage (Nucleic Acids Res (2003) 31, e59), Ex-phage (Nucleic Acids Res (2002) 30, e18), Phaberge (J Immunol Methods (2003) 274, 233-244), XP5 (J Immunol Methods (2012) 376, 46-54), DeltaPhage (Nucleic Acids Res (2012) 40, e120). A bacterial strain carrying a helper phage derivative that expresses all the components required for encapsidation may also be used.

In another particular embodiment, such methods further comprise the use of a satellite phage. Preferably, the satellite phages can encode proteins that promote capsid size reduction of the principal phage, as described for the P4 Sid protein that controls the P2 capsid size to fit its smaller genome. Such satellite phage can for example be phages P4.

In another aspect, such methods further comprise the use of P4 satellite phage proteins, preferably the Sid protein, to promote the encapsidation of the payload in P2 bacterial virus capsid.

Alternatively, the bacterial delivery vehicle (i.e. bacterial virus particle) can be produced in vitro by contacting the payload with the structural and functional proteins necessary to promote an in vitro packaging of the payload into a particular bacterial virus particle (Hohn et al, PNAS, 1977) (Collins et al, PNAS, 1978)(Gunther et al, NAR, 1993)

Kit and Uses Thereof

In some embodiments, the present invention also relates to a kit comprising the payload as disclosed herein, optionally a satellite phage and/or a helper phage to promote the packaging of the payload in the at least two bacteria delivery vehicles and optionally bacterial cells suitable for packaged payload production.

In one embodiment, the kit further comprises a satellite phage and/or a helper phage to promote the packaging of the payload in the at least two bacteria delivery vehicles.

In a particular embodiment, the kit further comprises a Helper phage selected in the group consisting of M13KO7, R408, VCSM13, KM13 (Res Microbiol (2001) 152, 187-191), M13MDD3.2 (FEMS Microbiol Lett (1995) 125, 317-321), R408d3 (Gene (1997) 198, 99-103), VCSM13d3 (Gene (1997) 198, 99-103), Hyperphage (Nat Biotechnol (2001) 19, 75-78), CT helper phage (Nucleic Acids Res (2003) 31, e59), Ex-phage (Nucleic Acids Res (2002) 30, e18), Phaberge (J Immunol Methods (2003) 274, 233-244), XP5 (J Immunol Methods (2012) 376, 46-54), DeltaPhage (Nucleic Acids Res (2012) 40, e120).

In another embodiment, the kit further comprises a satellite phage or satellite phage genes. Preferably, the satellite phages can encode proteins that promote capsid size reduction of the principal phage, as described for the P4 Sid protein that controls the P2 capsid size to fit its smaller genome.

In some embodiments, the kit further comprises vials containing natural or non-natural bacterial host cells suitable for packaged payload production.

In one embodiment, the kit further comprises bacterial cells suitable for packaged payload production selected in the group consisting of *Actinomyces, Achromobacter, Acidaminococcus, Acinetobacter, Aeromonas, Alcaligenes, Bacillus, Bacteroides, Bifidobacterium, Bordetella, Borrelia, Brucella, Burkholderia, Butyriviberio, Campylobacter, Chlamydia, Citrobacter, Clostridium, Corynebacterium, Eikenella, Enterobacter, Enterococcus, Erysipelothrix, Escherichia, Eubacterium, Flavobacterium, Francisella, Fusobacterium, Haemophilus, Helicobacter, Klebsiella, Lactobacillus, Legionella, Leptospira, Listeria, Methanobrevibacter, Morganella, Mycobacterium, Mycoplamsa, Neisseria, Nocardia, Peptococcus, Prevotella, Providencia, Propionibacterium, Plesiomonas, Pseudomonas, Rickettsia, Ruminococcus, Rhodococcus, Salmonella, Sarcina, Serratia, Shigella, Spirillum, Staphylococcus Streptobacillus, Streptococcus, Treponema, Vibrio* and *Yersinia*.

In one embodiment the bacteria carry a helper phage or a satellite phage derivative that expresses all the components required for the payload packaging.

In certain embodiments, the bacterial host cells are *E. coli*.

The kit may further comprise one or more of wash buffers and/or reagents, hybridization buffers and/or reagents, labelling buffers and/or reagents, and detection means. The buffers and/or reagents are usually optimized for the particular utilization for which the kit is intended. Protocols for using these buffers and reagents for performing different steps of the procedure may also be included in the kit. Further optional components of the kits may include expression media with different supply (antibiotics or nutriment) for bacteria growth and/or selection of bacteria containing the payload of the invention.

Pharmaceutical or Veterinary Composition

The present invention relates to a pharmaceutical or veterinary composition comprising the payload as described hereabove packaged into a bacterial delivery vehicle. More particularly, the present invention relates to a pharmaceutical or veterinary composition comprising the payload described hereabove packaged into at least two different bacterial delivery vehicles.

Accordingly, the present invention relates to a pharmaceutical or veterinary composition comprising at least two different bacterial virus particles with the same payload as described hereabove packaged into them. The at least two different bacterial virus particles can be prepared from any of the above described bacteriophages.

In one embodiment, the pharmaceutical composition comprising at least two bacterial virus particles capable of targeting at least two different bacteria and of introducing the payload into the bacteria. Alternatively, the pharmaceutical composition comprising at least two bacterial virus particles capable of targeting the same bacterium and of introducing the payload into this bacterium.

In some embodiment, the pharmaceutical composition comprises several bacterial delivery vehicles with the same payload according to the present invention and/or bacterial delivery vehicles with different payload inside.

For pharmaceutical composition comprising different bacterial delivery vehicles with the same payload inside, it can be also really advantageous to be able to identify and quantify in the composition, each of the bacterial delivery vehicles individually. Even if the composition comprises bacterial delivery vehicles or bacterial virus particles which are different, they may share common conserved regions, which makes it difficult to develop protein detection and quantification assays (ELISA, Western Blot) specific enough to reliably detect and quantify each delivery vehicle or virus particle individually from the composition. To overcome this hurdle which can be of importance from the regulatory standpoint, a cocktail or mixture of bacterial delivery vehicles can be developed that contain identical DNA payloads with the exception of a unique "tracer" sequence designed in such a way that all the payloads packaged in a same delivery vehicles have the same "tracer" sequence and payloads packaged in different delivery vehicles have different "tracer" sequences. In this way, both the presence and the relative abundance of each delivery vehicle in a mixture can be confirmed by PCR, qPCR, ddPCR, or NGS using primers specific for the "tracer" sequences. In a preferred aspect, the tracer is composed of two nucleic acid constant regions flanking one nucleic acid variable region. Each region of the tracer can be of any length, and more preferably between 25 and 50 nucleotides each.

Alternatively, the mixture of delivery vehicles contains delivery vehicles comprising different DNA payloads, each DNA payload comprising different tracer or the same tracer, in order to allow detection of each delivery vehicles and determination of their relative abundance.

The pharmaceutical or veterinary composition according to the invention can be formulated for any conventional route of administration including a topical, enteral, oral, parenteral, intranasal, intravenous, intramuscular, subcutaneous or intraocular administration and the like, preferably enteral, oral, or inhalation routes.

Then, the pharmaceutical or veterinary composition according to the invention can be administered by any conventional route of administration including a topical, enteral, oral, parenteral, intranasal, intravenous, intramuscular, subcutaneous or intraocular administration and the like, preferably enteral, oral, intranasal or inhalation routes.

Preferably, the pharmaceutical or veterinary composition according to the invention may be administered by enteral or parenteral route of administration. When administered parenterally, the pharmaceutical or veterinary composition according to the invention is preferably administered by intravenous route of administration. When administered enterally, the pharmaceutical or veterinary composition according to the invention is preferably administered by oral route of administration.

For oral administration, the pharmaceutical or veterinary composition can be formulated into conventional oral dosage forms such as tablets, capsules, powders, granules and liquid preparations such as syrups, elixirs, and concentrated drops. Nontoxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials, are also necessary. For example, starch, gelatin, sugars such as lactose or dextrose, and natural or synthetic gums can be used as binders. Disintegrants are also necessary in the tablets to facilitate break-up of the tablet. Disintegrants include starches, clays, celluloses, algins, gums and cross-linked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

For transdermal administration, the pharmaceutical or veterinary composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compounds can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Pharmaceutical or veterinary compositions according to the invention may be formulated to release the active ingredients substantially immediately upon administration or at any predetermined time or time period after administration.

In a particular embodiment, the pharmaceutical or veterinary composition according to the invention further comprises another active ingredient. The additional active ingredient can be a prebiotic, a probiotic, an antibiotic, another antibacterial or antibiofilm agent and/or any agent enhancing the binding of the delivery particle on the bacteria and/or the delivery of the payload to the bacteria.

Prebiotics include, but are not limited to, amino acids, biotin, fructo-oligosaccharide, galacto-oligosaccharides, hemicelluloses (e.g., arabinoxylan, xylan, xyloglucan, and glucomannan), inulin, chitin, lactulose, mannan oligosaccharides, oligofructose-enriched inulin, gums (e.g., guar gum, gum arabic and carregenaan), oligofructose, oligodextrose, tagatose, resistant maltodextrins (e.g., resistant starch), trans-galactooligosaccharide, pectins (e.g., xylogalactouronan, citrus pectin, apple pectin, and rhamnogalacturonan-I), dietary fibers (e.g., soy fiber, sugarbeet fiber, pea fiber, corn bran, and oat fiber) and xylooligosaccharides.

Probiotics include, but are not limited to lactobacilli, bifidobacteria, streptococci, enterococci, propionibacteria, saccaromycetes, lactobacilli, bifidobacteria, or proteobacteria.

The antibiotic can be selected from the group consisting in penicillins such as penicillin G, penicillin K, penicillin N, penicillin O, penicillin V, methicillin, benzylpenicillin, nafcillin, oxacillin, cloxacillin, dicloxacillin, ampicillin, amoxicillin, pivampicillin, hetacillin, bacampicillin, metampicillin, talampicillin, epicillin, carbenicillin, ticarcillin, temocillin, mezlocillin, and piperacillin; cephalosporins such as cefacetrile, cefadroxil, cephalexin, cefaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, loracarbef, cefbuperazone, cefminox, cefotetan, cefoxitin, cefotiam, cefcapene, cefdaloxime, cefdinir, cefditoren, cefetamet, cefixime, cefmenoxime, cefodizime, cefotaxime, cefovecin, cefpimizole, cefpodoxime, cefteram, ceftamere, ceftibuten, ceftiofur, ceftiolene, ceftizoxime, ceftriaxone, cefoperazone, ceftazidime, latamoxef, cefclidine, cefepime, cefluprenam, cefoselis, cefozopran, cefpirome, cefquinome, flomoxef, ceftobiprole, ceftaroline, ceftolozane, cefaloram, cefaparole, cefcanel, cefedrolor, cefempidone, cefetrizole, cefivitril, cefmatilen, cefmepidium, cefoxazole, cefrotil, cefsumide, ceftioxide, cefuracetime, and nitrocefin; polymyxins such as polysporin, neosporin, polymyxin B, and polymyxin E, rifampicins such as rifampicin, rifapentine, and rifaximin; Fidaxomicin; quinolones such as cinoxacin, nalidixic acid, oxolinic acid, piromidic acid, pipemidic acid, rosoxacin, ciprofloxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, temafloxacin, tosufloxacin, clinafloxacin, gatifloxacin, gemifloxacin, moxifloxacin, sitafloxacin, trovafloxacin, prulifloxacin, delafloxacin, nemonoxacin, and zabofloxacin; sulfonamides such as sulfafurazole, sulfacetamide, sulfadiazine, sulfadimidine, sulfafurazole, sulfisomidine, sulfadoxine, sulfamethoxazole, sulfamoxole, sulfanitran, sulfadimethoxine, sulfametho-xypyridazine, sulfametoxydiazine, sulfadoxine, sulfametopyrazine, and terephtyl; macrolides such as azithromycin, clarithromycin, erythromycin, fidaxomicin, telithromycin, carbomycin A, josamycin, kitasamycin, midecamycin, oleandomycin, solithromycin, spiramycin, troleandomycin, tylosin, and roxithromycin; ketolides such as telithromycin, and cethromycin; lluoroketolides such as solithromycin; lincosamides such as lincomycin, clindamycin, and pirlimycin; tetracyclines such as demeclocycline, doxycycline, minocycline, oxytetracycline, and tetracycline; aminoglycosides such as amikacin, dibekacin, gentamicin, kanamycin, neomycin, netilmicin, sisomicin, tobramycin, paromomycin, and streptomycin; ansamycins such as geldanamycin, herbimycin, and rifaximin; carbacephems such as loracarbef; carbapenems such as ertapenem, doripenem, imipenem (or cilastatin), and meropenem; glycopeptides such as teicoplanin, vancomycin, telavancin, dalbavancin, and oritavancin; lincosamides such as clindamycin and lincomycin; lipopeptides such as daptomycin; monobactams such as aztreonam; nitrofurans such as furazolidone, and nitrofurantoin; oxazolidinones such as linezolid, posizolid, radezolid, and torezolid; teixobactin, clofazimine, dapsone, capreomycin, cycloserine, ethambutol, ethionamide, isoniazid, pyrazinamide, rifabutin, arsphenamine, chloramphenicol, fosfomycin, fusidic acid, metronidazole, mupirocin, platensimycin, quinupristin (or dalfopristin), thiamphenicol, tigecycline, tinidazole, trimethoprim, alatrofloxacin, fidaxomicin, nalidixice acide, rifampin, derivatives and combination thereof.

The pharmaceutical or veterinary composition according to the invention may further comprise a pharmaceutically acceptable vehicle. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. Suitable solid vehicles include, for example calcium phosphate, magnesium stearate, talc, sugars, lactose, dextrin, starch, gelatin, cellulose, polyvinylpyrrolidine, low melting waxes and ion exchange resins.

The pharmaceutical or veterinary composition may be prepared as a sterile solid composition that may be suspended at the time of administration using sterile water, saline, or other appropriate sterile injectable medium. The pharmaceutical or veterinary compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 8o (oleate esters of sorbitol and its anhydrides copolymerized with ethylene oxide) and the like. The particles according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for enteral administration include sterile solutions, emulsions, and suspensions.

The bacterial virus particles according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and enteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for enteral administration. The liquid vehicle for pressurized compositions can be a halogenated hydrocarbon or other pharmaceutically acceptable propellant.

For transdermal administration, the pharmaceutical or veterinary composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compounds can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

The pharmaceutical or veterinary composition, the bacterial virus particles as disclosed above and the combination of at least two different bacterial virus particles having the same payload can be used as a medicament.

The present invention relates to the pharmaceutical or veterinary composition, the bacterial virus particles as disclosed above and the combination of at least two different bacterial virus particles having the same payload for use in the treatment of a disorder or a disease caused by a bacterium, to the use of the pharmaceutical or veterinary composition, the bacterial virus particles as disclosed above and the combination of at least two different bacterial virus particles having the same payload for the manufacture of a medicament useful in the treatment of a disorder or a disease caused by a bacterium; and to a method for treating a disorder or a disease caused by a bacterium comprising the administration of a therapeutically effective amount of the pharmaceutical or veterinary composition, the bacterial virus particles as disclosed above and the combination of at least two different bacterial virus particles having the same payload. Such diseases or disorders include an infection, preferably a bacterial infection, inflammatory diseases, auto-immune diseases, cancers, metabolic disorders and brain disorders.

In a particular embodiment, the bacterial virus particles only target the bacterial strain responsible of the disease or disorder and thus allow the subject to be treated to conserve a healthy microbiome.

The diseases or disorders caused by bacteria may be selected from the group consisting of abdominal cramps, acne vulgaris, acute epiglottitis, arthritis, bacteraemia, bloody diarrhea, botulism, Brucellosis, brain abscess, chancroid venereal disease, *Chlamydia*, Crohn's disease, conjunctivitis, cholecystitis, colorectal cancer, polyposis, dysbiosis, Lyme disease, diarrhea, diphtheria, duodenal ulcers, endocarditis, erysipelothricosis, enteric fever, fever, glomerulonephritis, gastroenteritis, gastric ulcers, Guillain-Barre syndrome tetanus, gonorrhoea, gingivitis, inflammatory bowel diseases, irritable bowel syndrome, leptospirosis, leprosy, listeriosis, tuberculosis, Lady Widermere syndrome, Legionaire's disease, meningitis, mucopurulent conjunctivitis, multi-drug resistant bacterial infections, multi-drug resistant bacterial carriage, myonecrosis-gas gangrene, *Mycobacterium avium* complex, neonatal necrotizing enterocolitis, nocardiosis, nosocomial infection, otitis, periodontitis, phalyngitis, pneumonia, peritonitis, purpuric fever, Rocky Mountain spotted fever, shigellosis, syphilis, sinusitis, sigmoiditis, septicaemia, subcutaneous abscesses, tularaemia, tracheobronchitis, tonsillitis, typhoid fever, ulcerative colitis, urinary infection, whooping cough.

The infection caused by bacteria may be selected from the group consisting of skin infections such as acne, intestinal infections such as esophagitis, gastritis, enteritis, colitis, sigmoiditis, rectitis, and peritonitis, urinary tract infections, vaginal infections, female upper genital tract infections such as salpingitis, endometritis, oophoritis, myometritis, parametritis and infection in the pelvic peritoneum, respiratory tract infections such as pneumonia, intra-amniotic infections, odontogenic infections, endodontic infections, fibrosis, meningitis, bloodstream infections, nosocomial infection such as catheter-related infections, hospital acquired pneumonia, post-partum infection, hospital acquired gastroenteritis, hospital acquired urinary tract infections, or a combination thereof. Preferably, the infection according to the invention is caused by a bacterium presenting an antibiotic resistance. In a particular embodiment, the infection is caused by a bacterium as listed above in the targeted bacteria.

The metabolic disorder includes obesity and diabetes.

In a particular embodiment, the invention concerns a pharmaceutical or veterinary composition for use in the treatment of pathologies involving bacteria of the human microbiome, such as inflammatory and auto-immune diseases, cancers, infections or brain disorders. Indeed, some bacteria of the microbiome, without triggering any infection, can secrete molecules that will induce and/or enhance inflammatory or auto-immune diseases or cancer development. More specifically, the present invention relates also to modulating microbiome composition to improve the efficacy of immunotherapies based, for example, on CAR-T (Chimeric Antigen Receptor T) cells, TIL (Tumor Infiltrating Lymphocytes) and Tregs (Regulatory T cells) also known as suppressor T cells. Modulation of the microbiome composition to improve the efficacy of immunotherapies may also include the use of immune checkpoint inhibitors well known in the art such as, without limitation, PD-1 (programmed cell death protein 1) inhibitor, PD-L1 (programmed death ligand 1) inhibitor and CTLA-4 (cytotoxic T lymphocyte associated protein 4).

Some bacteria of the microbiome can also secrete molecules that will affect the brain.

Therefore, a further object of the invention is a method for controlling the microbiome of a subject, comprising administering an effective amount of the pharmaceutical composition as disclosed herein in said subject.

In a particular embodiment, the invention also relates to a method for personalized treatment for an individual in need of treatment for a bacterial infection comprising: i) obtaining a biological sample from the individual and determining a group of bacterial DNA sequences from the sample; ii) based on the determining of the sequences, identifying one or more pathogenic bacterial strains or species that were in the sample; and iii) administering to the individual a pharmaceutical composition according to the invention comprising a combination of at least two bacterial virus particles capable of recognizing each pathogenic bacterial strain or species identified in the sample and to deliver the packaged payload.

Preferably, the biological sample comprises pathological and non-pathological bacterial species, and subsequent to administering the pharmaceutical or veterinary composition according to the invention to the individual, the amount of pathogenic bacteria on or in the individual are reduced, but the amount of non-pathogenic bacteria is not reduced.

In another particular embodiment, the invention concerns a pharmaceutical or veterinary composition according to the invention for use in order to improve the effectiveness of drugs. Indeed, some bacteria of the microbiome, without being pathogenic by themselves, are known to be able to metabolize drugs and to modify them in ineffective or harmful molecules.

In another particular embodiment, the invention concerns the in-situ bacterial production of any compound of interest, including therapeutic compound such as prophylactic and therapeutic vaccine for mammals. The compound of interest can be produced inside the targeted bacteria, secreted from the targeted bacteria or expressed on the surface of the targeted bacteria. In a more particular embodiment, an antigen is expressed on the surface of the targeted bacteria for prophylactic and/or therapeutic vaccination.

The present invention also relates to a non-therapeutic use of the bacterial virus particles as disclosed above and the combination of at least two different bacterial virus particles having the same payload according to the invention. For instance, the non-therapeutic use can be a cosmetic use or a use for improving the well-being of a subject, in particular a subject who does not suffer from a disease. Accordingly, the present invention also relates to a cosmetic composition or a non-therapeutic composition comprising the bacterial virus particles as disclosed above and the combination of at least two different bacterial virus particles having the same payload according to the invention.

Subject, Regimen and Administration

The subject according to the invention is an animal, preferably a mammal, even more preferably a human. However, the term "subject" can also refer to non-human animals, in particular mammals such as dogs, cats, horses, cows, pigs, sheep, donkeys, rabbits, ferrets, gerbils, hamsters, chinchillas, rats, mice, guinea pigs and non-human primates, among others, or non-mammals such as poultry, that are in need of treatment.

The human subject according to the invention may be a human at the prenatal stage, a new-born, a child, an infant, an adolescent or an adult at any age.

In a preferred embodiment, the subject has been diagnosed with, or is at risk of developing an infection, a disorder and/or a disease preferably due to a bacterium. Diagnostic method of such infection, disorder and/or disease are well known by the man skilled in the art.

In a particular embodiment, the infection, disorder and/or disease presents a resistance to treatment, preferably the infection, disorder or disease presents an antibiotic resistance.

In a particular embodiment, the subject has never received any treatment prior to the administration of the delivery vehicles according to the invention, preferably a payload according to the invention, particularly a payload packaged into a delivery vehicle according to the invention, preferably a packaged plasmid or phagemid into a bacterial virus particle according to the invention, or of a pharmaceutical or veterinary composition according to the invention.

In a particular embodiment, the subject has already received at least one line of treatment, preferably several lines of treatment, prior to the administration of the delivery vehicles according to the invention, preferably a payload according to the invention, particularly a payload packaged into a delivery vehicle according to the invention, preferably a packaged plasmid or phagemid into a bacterial virus particle according to the invention, or of a pharmaceutical or veterinary composition according to the invention.

Preferably, the treatment is administered regularly, preferably between every day and every month, more preferably between every day and every two weeks, more preferably between every day and every week, even more preferably the treatment is administered every day. In a particular embodiment, the treatment is administered several times a day, preferably 2 or 3 times a day, even more preferably 3 times a day.

The duration of treatment with delivery vehicles according to the invention, preferably a payload according to the invention, particularly a payload packaged into a delivery vehicle according to the invention, preferably a packaged plasmid or phagemid into a bacterial virus particle according to the invention, or with a pharmaceutical or veterinary composition according to the invention, is preferably comprised between 1 day and 20 weeks, more preferably between 1 day and 10 weeks, still more preferably between 1 day and 4 weeks, even more preferably between 1 day and 2 weeks. In a particular embodiment, the duration of the treatment is of about 1 week. Alternatively, the treatment may last as long as the infection, disorder and/or disease persists.

The form of the pharmaceutical or veterinary compositions, the route of administration and the dose of administration of delivery vehicles according to the invention, preferably of a payload according to the invention, particularly of a payload packaged into a delivery vehicle according to the invention, preferably of a packaged plasmid or phagemid into a bacterial virus particle according to the invention, or of a pharmaceutical or veterinary composition according to the invention can be adjusted by the man skilled in the art according to the type and severity of the infection (e.g. depending on the bacteria species involved in the disease, disorder and/or infection and its localization in the patient's or subject's body), and to the patient or subject, in particular its age, weight, sex, and general physical condition.

Particularly, the amount of delivery vehicles according to the invention, preferably a payload according to the invention, particularly a payload packaged into a delivery vehicle according to the invention, preferably a packaged plasmid or phagemid into a bacterial virus particle according to the invention, or of a pharmaceutical or veterinary composition according to the invention, to be administered has to be determined by standard procedure well known by those of ordinary skills in the art. Physiological data of the patient or subject (e.g. age, size, and weight) and the routes of administration have to be taken into account to determine the appropriate dosage, so as a therapeutically effective amount will be administered to the patient or subject.

For example, the total amount of delivery vehicles, particularly a payload packaged into a delivery vehicle according to the invention, preferably a plasmid or phagemid packaged into a bacterial virus particle according to the invention, for each administration is comprised between $10^4$ and $10^{15}$ delivery vehicles.

EXAMPLES—RESULTS

The inventors have shown single payload encapsidation in three different capsids from three different phage families: P1-like (P1), P2-like (186) and lambdoid (lambda). P1 relies on a headfull packaging system whereas both P2-like and Lambdoid rely on cohesive end packaging. Even if they use the same phage termini type (cohesive ends) lambdoid and P2-like use a different DNA substrate for the packaging. Indeed, lambdoid phages undergo rolling circle replication to generate a concatemer of the phage genome (head to tail repeat of the DNA), then the terminase bind on the packaging recognition site called cos, generate a double strand cleavage, get recruited on the procapsid and start to fulfill it in a unidirectional process until the next cos. For P2, the preferred DNA substrate is a circular monomer, which is recognized by the terminase at the cos level and then cleaved and packaged. Consequently, a monomeric circular DNA molecule that is suitable for P2 packaging and can also get concatemerized for lambda packaging was used. For phages relying on headful packaging such as P1, chromosomes are circularly permuted and contain terminally redundancy that allow recirculization of DNA upon injection. Then the packaging site called pac is recognized by the terminase (or pacase) that attaches to a procapsid and fulfill more than 100% of the genome and cut.

Construction and Test

To test the packaging of a single payload into 3 different phage capsids, a lambda cos site, a cos site recognized by 186 terminase and a P1 pac site were cloned into a single plasmid and transformed into 3 different *E. coli* production strains:

CY2120b (Cronan et al, 2013, Plasmid 69: 81-89) a lysogen of lambda lacking the wild-type lambda cos site C600(186)Δcos a C600 lysogen of 186 lacking the wild-type 186 cos site KL739 a C600 lysogen of P1

Along with the 3 different packaging sites, the plasmid includes a chloramphenicol resistance gene that allows scoring for transductant, a colE1 origin of replication, the Coi gene under the control of pBad that allows induction of the lytic cycle of P1, a cis element inside the cin gene of P1 and the P1 replication origin inside repL.

The three different lysogene cell lines containing the payload were induced to produce phagemids particles. For the production cell line CY2120b and C600(186)Δcos only phagemids particles and no phages were produced due to the deletion of the cos site from the prophages. For the strain KL739, a mix of a phage and phagemid particles were produced.

Titrations of the pure phagemids particles were done on strain *E. coli* K-12 MG1655 whereas titration of the phagemid particles mixed with phages where done on the lysogene itself (KL739) allowing titration of phagemids particles without killing the bacteria. Count of transductant on chloramphenicol was performed the day after.

The entire test, i.e. induction and titration, was performed in triplicate. The graphs of FIG. 1 represent the mean of the phagemid particle concentration per μL obtained for each phagemids particles in 3 independent experiments as detailed in FIG. 2.

The results show that a single plasmid is able to get packaged and gives viable phagemids particles for all the three different capsids. The number of particles varies from $2.53 \cdot 10^7$ for lambda, $7.77 \cdot 10^5$ for 186 to $7.9 \cdot 10^4$ for P1. Such differences can be explained by the competition between the P1 phage still containing the pac site and the plasmid for the packaging.

In conclusion, it has been demonstrated that adding several packaging signals (pac, cos) from phages having different packaging mechanisms allows for the production of phagemids particles with the same DNA plasmid but different capsids.

MATERIAL AND METHODS

Production of Phagemids Particles

The three different cell lines containing the payload were grown separately overnight in LB+chloramphenicol 25 μg/mL. The following day, cells were diluted 1/100 in 10 mL of LB and incubated at 30° C. with shaking. For strain CY2120b and C600(186)Δcos the culture, at OD600 nm around 0.6, were shifted to 42° C. for 30 minutes to induce the entry into lytic cycle. After that, cells were shifted back to 37° C. for 2 hours (C600(186)Δcos) or 3 hours (CY2120b) to allow virion assembly and packaging in either of the two capsids. Chlorophorm was added in the case of CY2120b to burst the cell. Cell lysate was filtered with 0.2 μm syringe filter.

For the KL739 production, the induction of the lytic cycle was performed by adding arabinose 0.2%. After 2 hours cell lysate was filtered with 0.2 μm syringe filter.

Titration of Phagemids Particles

*E. coli* KL739 and *E. coli* K-12 MG1655 overnight culture in LB was diluted 1/100. At OD600 nm between 0.6 and 0.8, 90 μl of cells were incubated at 37° C. for 30 min with 10 μL of each phagemids diluted 1/100. After incubation serial dilution of the samples were performed in PBS 1× and all dilution were plated on LB supplemented with chloramphenicol 25 μg/mL. Plate were incubated at 37° C. overnight and the CFU counts done the day after.

REFERENCES

Abudayyeh, O., et al. (2017). RNA targeting with CRISPR-Cas13. Nature 550, 280.

Cronan, J. Improved plasmid-based system for fully regulated off-to-on gene expression in *Escherichia coli*: Application to production of toxic proteins. Plasmid 69, 81-89 (2013).

Fonfara, I., et al. (2014). Phylogeny of Cas9 determines functional exchangeability of dual-RNA and Cas9 among orthologous type II CRISPR-Cas systems. Nucleic Acids Research 42, 2577-2590.

Koonin, E., et al. (2017). Diversity, classification and evolution of CRISPR-Cas systems. Curr Opin Microbiol 37, 67-78.

Krom, R., Bhargava, P., Lobritz, M. & Collins, J. Engineered Phagemids for Nonlytic, Targeted Antibacterial Therapies. *Nano Letters* 15, 4808-4813 (2015).

Yan, W., et al. (2018). Cas13d Is a Compact RNA-Targeting Type VI CRISPR Effector Positively Modulated by a WYL-Domain-Containing Accessory Protein. Mol Cell.

Krupovic, M., et al. (2015). Taxonomy of prokaryotic viruses: update from the ICTV bacterial and archaeal viruses subcommittee. Arch Virol 161, 1095-1099.

B Hohn and K Murray (1977). Packaging recombinant DNA molecules into bacteriophage particles in vitro. PNAS 74(8): 3259-3263.

John Collins and Barbara Hohn (1978). Cosmids: A type of plasmid gene-cloning vector that is packageable in vitro in bacteriophage λ heads. PNAS 75(9): 4242-4246.

E J Gunther, et al. (1993). High efficiency, restriction-deficient in vitro packaging extracts for bacteriophage lambda DNA using a new *E. coli* lysogen. NAR 21(16): 3903-3904.

What is claimed is:

1. A pharmaceutical composition comprising at least two different bacterial delivery vehicles into which the same payload is packaged, wherein the payload comprises: a nucleic acid sequence of interest encoding a therapeutic molecule of interest, under the control of a promoter; and at least two orthogonal bacterial virus packaging sites that allow packaging of said payload into said at least two different bacterial delivery vehicles and a pharmaceutical acceptable carrier,
wherein the nucleic acid sequence of interest encodes one or more components of a Cas9 system for the reduction of gene expression or inactivation of a gene, wherein said gene is selected from the group consisting of an antibiotic resistance gene, a virulence factor or virulence protein gene, a toxin factor or toxin protein gene, a bacterial receptor gene, a membrane protein gene, a structural protein gene, a secreted protein gene, and a drug resistance gene, or any combination thereof.

2. The pharmaceutical composition according to claim 1, wherein the at least two orthogonal bacterial virus packaging sites are selected from the group consisting of:
(i) at least two different cos sites; (ii) at least two different pac sites; (iii) at least two different concatemer junction sites; (iv) at least one cos site and at least one pac site; (v) at least one cos site and at least one concatemer junction site; (vi) at least one pac site and at least one concatemer junction site; and (vii) at least one cos site, at least one pac site and at least one concatemer junction site.

3. The pharmaceutical composition according to claim 1, wherein the at least two orthogonal bacterial virus packaging sites are selected from the group consisting of: a λ cos site, a P4 cos site, a SPP1 pac site, a P1 pac site, a T1 pac site, a mu pac site, a P22 pac site, a φ8 pac site, a Sf6 pac site, a 149 pac site, a T7 concatemer junction, and an μl 122-concatemer junction.

4. The pharmaceutical composition according to claim 3, wherein the at least two orthogonal bacterial virus packaging sites comprise: (i) λ cos site and P4 cos site; (ii) a λ cos site, P4 cos site and P1 pac site; (iii) a λ cos site, P4 cos site and T7 concatemer junction; or (iv) a λ cos site, P4 cos site, P1 pac site and T7 concatemer junction.

5. The pharmaceutical composition according to claim 1, wherein the bacterial delivery vehicles are bacterial viruses.

6. The pharmaceutical composition according to claim 5, wherein the bacterial viruses are selected from the group consisting of BW73, B278, D6, D108, E, E1, E24, E41, FI-2, FI-4, FI-5, HI8A, Ffl8B, i, MM, Mu, 025, PhI-5, Pk, PSP3, P1, P1D, P2, P4, S1, Wφ, φK13, φ1, φ2, φ7, φ92, 7 A, 8φ, 9φ, 18, 28-1, 186, 299, HH-*Escherichia* (2), AB48, CM, C4, C16, DD-VI, E4, E7, E28, FI1, FI3, H, H1, H3, H8, K3, M, N, ND-2, ND-3, ND4, ND-5, ND6, ND-7, Ox-I, Ox-2, Ox-3, Ox-4, Ox-5, Ox-6, PhI-I, RB42, RB43, RB49, RB69, S, SaI-I, Sal-2, Sal-3, Sal-4, Sal-5, Sal-6, TC23, TC45, TuII*-6, TuIP-24, TuII*46, TuIP-60, T2, T4, T6, T35, αl, 1, IA, 3, 3A, 3T+, 5φ, 9266Q, CFO103, HK620, J, K, K1F, m59, no. A, no. E, no. 3, no. 9, N4, sd, T3, T7, WPK, W31, AH, φC3888, φK3, φK7, φK12, φV-1, Φ04-CF, Φ05, Φ06, Φ07, φ1, φ1.2, φ20, φ95, φ263, φ1O92, φ1, φ11, Ω28, 1, 3, 7, 8, 26, 27, 28-2, 29, 30, 31, 32, 38, 39, 42, 933W, NN-*Escherichia* (1), Esc-7-11, AC30, CVX-5, Cl, DDUP, EC1, EC2, E21, E29, F1, F26S, F27S, Hi, HK022, HK97, HK139, HK253, HK256, K7, ND-I, PA-2, q, S2, T1, T3C, T5, UC-I, w, β4, γ2, λ, ΦD326, φγ, Φ06, Φ7, Φ10, φ80, χ, 2, 4, 4A, 6, 8A, 102, 150, 168, 174, 3000, AC6, AC7, AC28, AC43, AC50, AC57, AC81, AC95, HK243, K1O, ZG/3A, 5, 5A, 21EL, H19-J and 933H.

7. The pharmaceutical composition according to claim 1, wherein the bacterial delivery vehicles are capable of targeting at least two different bacteria and of introducing the payload into the at least two different bacteria.

8. The pharmaceutical composition according to claim 1, wherein the bacterial delivery vehicles are capable of targeting the same bacteria and of introducing the payload into the same bacteria.

9. The pharmaceutical composition according to claim 1, wherein the pharmaceutical composition further comprises at least one additional active ingredient.

10. The pharmaceutical composition according to claim 9 wherein the additional active ingredient is selected from the group consisting of a prebiotic, a probiotic, an antibiotic, an antibacterial agent, an antibiofilm agent, an agent that enhances the targeting of the bacterial delivery vehicles to a bacteria and, an agent that enhances the delivery of the payload into the bacteria, or any combination thereof.

11. A pharmaceutical composition comprising at least two different bacterial delivery vehicles into which the same payload is packaged, wherein the payload comprises: a nucleic acid sequence of interest encoding a therapeutic molecule of interest, under the control of a promoter; and at least two orthogonal bacterial virus packaging sites that allow packaging of said payload into said at least two different bacterial delivery vehicles and a pharmaceutical acceptable carrier,
wherein the at least two orthogonal bacterial virus packaging sites comprise: (i) a λ cos site and P4 cos site; (ii) a λ cos site, P4 cos site and P1 pac site; (iii) a λ cos site, P4 cos site and T7 concatemer junction; or (iv) a λ cos site, P4 cos site, P1 pac site and T7 concatemer junction; and wherein the nucleic acid sequence of interest is selected from the group consisting of a nucleic acid sequence encoding a kinase, a nuclease, a Cas nuclease, a Cas9 nuclease, a guide RNA, a CRISPR locus, a toxin, a TALEN, a ZFN, a meganuclease, a recombinase, a bacterial receptor, a membrane protein, a structural protein, a secreted protein, a gene product conferring resistance to an antibiotic or to a drug, a toxic protein or a toxic factor, a virulence protein and a virulence factor, or any combination thereof.

12. The pharmaceutical composition according to claim 11, wherein the bacterial delivery vehicles are bacterial viruses.

13. The pharmaceutical composition according to claim 12, wherein the bacterial viruses are selected from the group consisting of BW73, B278, D6, D108, E, E1, E24, E41, FI-2, FI-4, FI-5, HI8A, Ffl8B, i, MM, Mu, 025, PhI-5, Pk, PSP3, P1, P1D, P2, P4, S1, Wφ, φK13, φ1, φ2, φ7, φ92, 7 A, 8φ, 9φ, 18, 28-1, 186, 299, HH-*Escherichia* (2), AB48, CM, C4, C16, DD-VI, E4, E7, E28, FI1, FI3, H, H1, H3, H8, K3, M, N, ND-2, ND-3, ND4, ND-5, ND6, ND-7, Ox-I, Ox-2, Ox-3, Ox-4, Ox-5, Ox-6, PhI-I, RB42, RB43, RB49, RB69, S, Sal-I, Sal-2, Sal-3, Sal-4, Sal-5, Sal-6, TC23, TC45, TuII*-6, TuIP-24, TuII*46, TuIP-60, T2, T4, T6, T35, α1, 1, IA, 3, 3A, 3T+, 5φ, 9266Q, CFO103, HK620, J, K, K1F, m59, no. A, no. E, no. 3, no. 9, N4, sd, T3, T7, WPK, W31, ΔH, φC3888, φK3, φK7, φK12, φV-1, Φ04-CF, Φ05, Φ06, Φ07, φ1, φ1.2, φ20, φ95, φ263, φ1O92, φ1, φ11, Ω8, 1, 3, 7, 8, 26, 27, 28-2, 29, 30, 31, 32, 38, 39, 42, 933W, NN-*Escherichia* (1), Esc-7-11, AC30, CVX-5, C1, DDUP, EC1, EC2, E21, E29, F1, F26S, F27S, Hi, HK022, HK97, HK139, HK253, HK256, K7, ND-I, PA-2, q, S2, T1, T3C, T5, UC-I, w, (β4, γ2, λ, ΦD326, φγ, Φ06, Φ7, Φ10, Φ80, χ, 2, 4, 4A, 6, 8A, 102, 150, 168, 174, 3000, AC6, AC7, AC28, AC43, AC50, AC57, AC81, AC95, HK243, K1O, ZG/3A, 5, 5A, 21EL, H19-J and 933H.

14. The pharmaceutical composition according to claim 11, wherein the bacterial delivery vehicles are capable of targeting at least two different bacteria and of introducing the payload into the at least two different bacteria.

15. The pharmaceutical composition according to claim 11, wherein the bacterial delivery vehicles are capable of targeting the same bacteria and of introducing the payload into the same bacteria.

16. The pharmaceutical composition according to claim 11, wherein the pharmaceutical composition further comprises at least one additional active ingredient.

17. The pharmaceutical composition according to claim 16 wherein the additional active ingredient is selected from the group consisting of a prebiotic, a probiotic, an antibiotic, an antibacterial agent, an antibiofilm agent, an agent that enhances the targeting of the bacterial delivery vehicles to a bacteria and, an agent that enhances the delivery of the payload into the bacteria, or any combination thereof.

* * * * *

UNITED STATES PATENT AND TRADEMARK OFFICE
CERTIFICATE OF CORRECTION

PATENT NO. : 11,124,776 B2  
APPLICATION NO. : 16/444576  
DATED : September 21, 2021  
INVENTOR(S) : Antoine Decrulle, Xavier Duportet and Igor Stzepourginski Page 1 of 1

It is certified that error appears in the above-identified patent and that said Letters Patent is hereby corrected as shown below:

On the Title Page

Item (71) should read:  
--Eligo Bioscience, Paris (FR)--

Item (73) should read:  
--Eligo Bioscience--

Signed and Sealed this  
Fifteenth Day of February, 2022

Drew Hirshfeld  
*Performing the Functions and Duties of the*  
*Under Secretary of Commerce for Intellectual Property and*  
*Director of the United States Patent and Trademark Office*